United States Patent
Block et al.

(10) Patent No.: US 11,155,574 B2
(45) Date of Patent: Oct. 26, 2021

(54) MANUFACTURING OPTIMIZATION OF GL-2045, A MULTIMERIZING STRADOMER

(71) Applicant: Gliknik Inc., Baltimore, MD (US)

(72) Inventors: David S. Block, Baltimore, MD (US); Emmanuel Y. Mérigeon, Baltimore, MD (US); Henrik Olsen, Baltimore, MD (US)

(73) Assignee: GLIKNIK INC., Baltimore, MD (US)

( * ) Notice: Subject to any disclaimer, the term of this patent is extended or adjusted under 35 U.S.C. 154(b) by 75 days.

(21) Appl. No.: 16/467,868

(22) PCT Filed: Dec. 8, 2017

(86) PCT No.: PCT/US2017/065397
§ 371 (c)(1),
(2) Date: Jun. 7, 2019

(87) PCT Pub. No.: WO2018/107079
PCT Pub. Date: Jun. 14, 2018

(65) Prior Publication Data
US 2020/0239518 A1    Jul. 30, 2020

Related U.S. Application Data

(60) Provisional application No. 62/432,402, filed on Dec. 9, 2016.

(51) Int. Cl.
| C07K 14/435 | (2006.01) |
| C07K 14/47  | (2006.01) |
| A61K 38/00  | (2006.01) |
| C07K 16/00  | (2006.01) |
| A61K 39/00  | (2006.01) |
| C07K 1/22   | (2006.01) |
| C07K 1/18   | (2006.01) |
| C07K 16/18  | (2006.01) |

(52) U.S. Cl.
CPC .................. *C07K 1/22* (2013.01); *C07K 1/18* (2013.01); *C07K 16/18* (2013.01); *C07K 2317/734* (2013.01)

(58) Field of Classification Search
CPC ......... A61K 38/00; C07K 14/47; A61P 43/00; A61P 35/00; A61P 29/00
See application file for complete search history.

(56) References Cited

U.S. PATENT DOCUMENTS

| 5,629,001 | A  | 5/1997  | Michael et al. |
| 7,148,321 | B2 | 12/2006 | Gillies et al. |
| 7,511,121 | B2 | 3/2009  | Arnason et al. |
| 8,680,237 | B2 | 3/2014  | Strome et al. |
| 9,512,208 | B2 | 12/2016 | Strome et al. |
| 9,512,210 | B2 | 12/2016 | Strome et al. |
| 9,926,362 | B2 | 3/2018  | Strome et al. |
| 10,208,105 | B2 | 2/2019 | Strome et al. |
| 10,851,154 | B2 | 12/2020 | Strome et al. |
| 10,941,191 | B2 | 3/2021  | Strome et al. |
| 2002/0115157 | A1 | 8/2002 | Davis et al. |
| 2002/0142374 | A1 | 10/2002 | Gallo et al. |
| 2002/0147326 | A1 | 10/2002 | Chaikin et al. |
| 2003/0044423 | A1 | 3/2003 | Gillies et al. |
| 2003/0118592 | A1 | 6/2003 | Ledbetter et al. |
| 2003/0216546 | A1 | 11/2003 | Tykocinski et al. |
| 2004/0110226 | A1 | 6/2004 | Lazar et al. |
| 2004/0147731 | A1 | 7/2004 | Parkos |
| 2004/0151725 | A1 | 8/2004 | Gray et al. |
| 2005/0033029 | A1 | 2/2005 | Lu |
| 2006/0263856 | A1 | 11/2006 | Gillies et al. |
| 2008/0260738 | A1 | 10/2008 | Moore et al. |
| 2008/0267980 | A1 | 10/2008 | Tomlinson et al. |
| 2009/0117133 | A1 | 5/2009 | Arnason et al. |
| 2009/0136485 | A1 | 5/2009 | Chu et al. |
| 2009/0217401 | A1 | 8/2009 | Korman et al. |
| 2009/0304715 | A1 | 12/2009 | Masuho et al. |
| 2010/0048877 | A1 | 2/2010 | Ruker et al. |
| 2010/0093979 | A1 | 4/2010 | Lazar |
| 2010/0135987 | A1 | 6/2010 | Hickman et al. |
| 2010/0227805 | A1 | 9/2010 | Karin et al. |
| 2010/0239633 | A1 | 9/2010 | Strome et al. |
| 2010/0311116 | A1 | 12/2010 | Wurm et al. |
| 2011/0243966 | A1 | 10/2011 | Farrington et al. |
| 2011/0305697 | A1 | 12/2011 | Walczak |
| 2012/0283417 | A1 | 11/2012 | Mosser et al. |
| 2012/0309941 | A1 | 12/2012 | Strome et al. |
| 2013/0156765 | A1* | 6/2013 | Block ..................... A61P 37/00 424/134.1 |
| 2014/0072582 | A1 | 3/2014 | Block et al. |
| 2014/0105913 | A1 | 4/2014 | Strome et al. |
| 2014/0335075 | A1 | 11/2014 | Strome et al. |
| 2015/0056185 | A1 | 2/2015 | Strome et al. |
| 2015/0152406 | A1 | 6/2015 | Grawunder |
| 2015/0218236 | A1 | 8/2015 | Pleass |
| 2016/0280768 | A1 | 9/2016 | Strome et al. |
| 2016/0355570 | A1 | 12/2016 | Strome et al. |
| 2018/0002388 | A1 | 1/2018 | Block et al. |
| 2018/0186862 | A1 | 7/2018 | Strome et al. |
| 2018/0244772 | A1 | 8/2018 | Block et al. |
| 2019/0218275 | A1 | 7/2019 | Strome et al. |
| 2019/0389941 | A1 | 12/2019 | Block et al. |

FOREIGN PATENT DOCUMENTS

| AU | 2015200330 B2 | 2/2015 |
| WO | WO 1994/015640 A1 | 7/1994 |

(Continued)

OTHER PUBLICATIONS

De Taeye, et al., "The Ligands for Human IgG and Their Effector Functions". Antibodies (2019); 8(2): 30, 18 pages.

(Continued)

*Primary Examiner* — Barry A Chestnut
(74) *Attorney, Agent, or Firm* — Cooley LLP

(57) ABSTRACT

The present disclosure involves optimized methods for production of biologically active proteins termed optimally manufactured stradomers. The present disclosure further provides compositions and methods useful in the treatment of diseases and conditions including autoimmune diseases, inflammatory diseases, or infectious diseases.

28 Claims, 37 Drawing Sheets
Specification includes a Sequence Listing.

(56) References Cited

FOREIGN PATENT DOCUMENTS

| | | |
|---|---|---|
| WO | WO 2000/009560 A2 | 2/2000 |
| WO | WO 2002/056910 A1 | 7/2002 |
| WO | WO 2002/072605 A2 | 9/2002 |
| WO | WO 2002/072608 A2 | 9/2002 |
| WO | WO 2003/010202 A1 | 2/2003 |
| WO | WO 2003/105898 A1 | 12/2003 |
| WO | WO 2005/007809 A2 | 1/2005 |
| WO | WO 2005/077981 A2 | 8/2005 |
| WO | WO 2005/089503 A2 | 9/2005 |
| WO | WO 2006/008739 A2 | 1/2006 |
| WO | WO 2006/061650 A2 | 6/2006 |
| WO | WO 2006/071206 A2 | 7/2006 |
| WO | WO 2006/074199 A1 | 7/2006 |
| WO | WO 2007/021129 A1 | 2/2007 |
| WO | WO 2008/151088 A2 | 12/2008 |
| WO | WO 2010/065578 A2 | 6/2010 |
| WO | WO 2010/094722 A2 | 8/2010 |
| WO | WO 2011/073692 A1 | 6/2011 |
| WO | WO 2012/016073 A2 | 2/2012 |
| WO | WO 2014/143185 A1 | 9/2014 |
| WO | WO 2015/017822 A1 | 2/2015 |
| WO | WO 2015/132364 A1 | 9/2015 |
| WO | WO 2015/168643 A2 | 11/2015 |
| WO | WO 2016/073917 A1 | 5/2016 |
| WO | WO2016073917 * | 5/2016 |
| WO | WO 2016/179472 A2 | 11/2016 |
| WO | WO 2017/019565 A1 | 2/2017 |
| WO | WO 2017/214321 A1 | 12/2017 |
| WO | WO 2018/018047 A2 | 1/2018 |
| WO | WO 2018/107079 A1 | 6/2018 |

OTHER PUBLICATIONS

Partial European Search Report, EP appl. No. 17877603.5, dated Jul. 6, 2020, 15 pages.
Reinhart, et al., "Influence of cell culture media and feed supplements on cell metabolism and quality of IgG produced in CHO-K1, CHO-S, and CHO-DG44". XP002799514, BMC Proc. (2015); 9(Suppl 9): vol. 9, No. P36, Published online Dec. 14, 2015.
Solodushko, et al., "Minimal piggyBac vectors for chromatin integration". Gene Therapy (2014); vol. 21, pp. 1-9. Published: Oct. 17, 2013.
[Author Unknown] "ActiCHO Media System. The All-Inclusive CHO Media Kit for Active Cells." Product datasheet [online], GE Healthcare Life Sciences (Mar. 2012) (retrieved on Jan. 25, 2018]. Retrieved from the Internet: <URL: http://www.ebiotrade.com/custom/GE/120725tw/images/A6.pdf>, 4 pages.
Alegre and Fallarino, "Mechanisms of CTLA-4-Ig in tolerane induction." Curr. Pharmaceutical Design (2006); 12 (2): 149-160.
Barrionuevo, et al.,"Immune complex-FcγR interaction modulates monocyte/macrophage molecules involved in inflammation and immune response." Clin. Exp. Immunol. (2003); 133 (2): 200-207.
Bazin, et al., "Tetramolecular immune complexes are more efficient than IVIg to prevent antibody-dependent in vitro and in vivo and in in vivo phagocytosis of blood cells." British J. Haematol. (2004); 127 (1): 90-96.
Boulet-Audet, et al., "In-column ATR-FTIR spectroscopy to monitor affinity chromatography purification of monoclonal antibodies." Scientific Reports (2016); 6 (Article No. 30526): 1-13.
Boyle, J.J., et al., "Solid-Phase Immunoglobulins IgG and IgM Activate Macrophages with Solid-Phase IgM Acting via a Novel Scavenger Receptor A Pathway." The American Journal of Pathology (2012); 181(1): 347-361.
Braathen, R., et al., "The Carboxyl-terminal Domains of IgA and IgM Direct Isotype-specific Polymerization and Interaction with the Polymeric Immunoglobulin Receptor." The Journal of Biological Chemistry (2002); 277 (45): 42755-42762.
Brønsted, et al., "Crosslinked dextran—a new capsule material for colon targeting of drugs." Journal of Controlled Release (Apr. 30, 1998); 53(1-3): 7-13.

Caron, et al., "Engineered Humanized Dimeric Forms of IgG are More Effective Antibodies." J. Exp. Med. (1992); 176: 1191-1195.
Chappel, et al., "Identification of the Fcγ receptor class I binding site in human IgG through the use of recombinant IgG1/IgG2 hybrid and point-mutated antibodies." Proc. Natl. Acad. Sci. USA (1991); 88: 9036-9040.
Czajkowsky, D.M., et al., Fc-fusion proteins: new developments and future perspectives. EMBO Molecular Medicine (Oct. 2012); 4(10): 1015-1028. Epub Jul. 26, 2012.
Dalakas, et al., "A Controlled Trial of High-Dose Intravenous Immune Globulin Infusions as Treatment for Dermatomyositis." The New England Journal of Medicine (Dec. 30, 1993); 329(27): 1993-2000.
Davis, et al., "Intermolecular disulfide bonding in IgM: effects of replacing cysteine residues in the μ heavy chain." EMBO J. (1989); 8 (9): 2519-2526.
Extended European Search Report for European Patent Application No. 18166541.5, dated Oct. 18, 2018, 9 pages.
Flanagan, et al., "Soluble Fc Fusion Proteins for Biomedical Research." Meth. Mol. Biol. (2007); 378: 33-52.
Gajdos, et al., "High-Dose Intravenous Gammaglobulin for Myasthenia Gravis." The Lancet (1984); 323 (8373): 406-407.
Ghumra, et al., "Structural requirements for the interaction of human IgM and IgA with the human Fcα/μ receptor." Eur. J. Immunol. (2009); 39 (4): 1147-1156.
Gliknik website. www.gliknik.com/research/stradomer.php, 2012.
Goldenberg, "Multiple Sclerosis Review." P&T (2012); 37(3): 175-184.
Greenwood et al., "Engineering multiple domains forms of the therapeutic antibody CAMPATH-1H: Effect on complement Lysis," Ther. Immunol. (1994); 1(5):247-255.
Hart, Samantha K., "Elution of Antibiotics from a Novel Crosslinked Dextran Gel: In vivo Quantification." Masters Thesis [18742], / ETDs: Virginia Tech Electronic Theses and Dissertations, Jun. 8, 2009, 65 pages.
Heller, et al., "Cutting Edge: Fc Receptor Type I for IgG on Macrophages and Complement Mediate the Inflammatory Response in Immune Complex Peritonitis." The Journal of Immunology (May 1999); 162 (10): 5657-5661.
Huang, et al., "In vitro study of combination of rhOPG-Fc and alendronate on inhibition osteoclast." Zhonghua Wai Ke Za Zhi (2005); 43(12):812-816. (Abstract Only, Article in Chinese).
Infante, A.J., "Uses (and abuses) of IVIG in immunology, hematology, and rheumatology." Presentation, University of Texas Health Science, Pediatrics Grand Rounds, San Antonio, TX, Feb. 19, 2010, 12 pages.
International Preliminary Report on Patentability, PCT appln. No. PCT/US2008/065428, 8 pages, dated Dec. 1, 2009.
International Search Report for PCT/US2008/065428, 5 pages, dated Feb. 10, 2009.
International Preliminary Report on Patentability for International Application No. PCT/US2017/065397, dated Jun. 11, 2019, 14 pages.
International Search Report and Written Opinion for International Application No. PCT/US2017/065397, dated Mar. 15, 2018, 5 pages.
Jain, et al., "Fully recombinant IgG2a Fc multimers (stradomers) effectively treat collagen-induced arthritis and prevent idiopathic thrombocytopenic purpura in mice." Arthritis Res. Ther. (2012); 14 (4): R192, 12 pages.
Jayne, et al., "Treatment of systemic vasculitis with pooled intravenous immunoglobulin." The Lancet (May 11, 1991); 337(8750): 1137-1139.
Jefferis, et al., "Interaction sites on human IgG-Fc for FcγR: current models." Immunol. Lett. (2002); 82(1-2): 57-65.
Jin and Balthasar, "Mechanisms of Intravenous Immunoglobulin Action in Immune Thrombocytopenic Purpura." Human Immunology (Apr. 2005); 66(4): 403-410.
Jin, et al., "Enzymatically crosslinked dextran-tyramine hydrogels as injectable scaffolds for cartilage tissue engineering." Tissue Eng Part A. (Aug. 2010); 16(8): 2429-2440.

(56) References Cited

OTHER PUBLICATIONS

Jukes, et al., "A Newly Developed Chemically Crosslinked Dextran-Poly(Ethylene Glycol) Hydrogel for Cartilage Tissue Engineering." Tissue Engineering Part A (2010); 16(2): 565-573.

Kacskovics, et al., "Fc receptors in livestock species." Vet. Immunol. Immunopathol. (2004); 102: 351-362.

Landschulz, et al., "The Leucine Zipper: A Hypothetical Structure Common to a New Class of DNA Binding Proteins." Science (1988); 240: 1759-1764.

LeHoang, et al., "Intravenous immunoglobulin (IVIg) for the treatment of birdshot retin ochoroidopathy." Journal Ocular Immunology and Inflammation (Mar. 2000); 8(1): 49-57.

Lund, et al., "Multiple Interactions of IgG with Its Core Oligosaccharide Can Modulate Recognition by Complement and Human Fcγ Receptor I and Influence the Synthesis of Its Oligosaccharide Chains." J. Immunol. (1996); 157: 4963-4969.

Mason, et al., "Reduced Culture Temperature Differentially Affects Expression and Biophysical Properties of Monoclonal Antibody Variants." Antibodies (2014); 3: 253-271.

Masterson and Smales, "The impact of process temperature on mammalian cell lines and the implications for the production of recombinant proteins in CHO cells." Pharmaceutical Bioprocessing (2014); 2(1): 49-61.

Matasci, et al., "The PiggyBac transposon enhances the frequency of CHO stable cell line generation and yields recombinant lines with superior productivity and stability." Biotechnol Bioeng. Sep. 2011;108(9):2141-50. doi: 10.1002/bit.23167. Epub Apr. 25, 2011.

Mekhaiel, et al., "Polymeric human Fc-fusion proteins with modified effector functions." Scientific Reports (2011); 1: 124, pp. 1-11.

Nimmerjahn and Ravetch, "Fcγ receptors as regulators of immune responses." Nature Reviews Immunology (2008); 8: 34-47.

Ong, et al., "How to accelerate the endothelialization of stents." Archives de maladies du coeur et des vaisseaux (2005); 98 (2): 123-126.

Opposition Proceedings No. 2012392760, Notice of Opposition filed by Gliknik, Inc. on Oct. 2, 2018, in Australian Patent Application No. 2012392760 in the name of Liverpool School of Tropical Medicine, 2 pages.

Opposition Proceedings No. 2012392760, Statement of Grounds and Particulars of Opposition filed by Gliknik, Inc. on Jan. 2, 2019, in Australian Patent Application No. 2012392760 in the name of Liverpool School of Tropical Medicine, 11 pages.

Opposition Proceedings No. 2012392760 (Australian Patent Application No. 2012392760 in the name of Liverpool School of Tropical Medicine) filed by Gliknik, Inc. on Jan. 2, 2019, Evidence in Answer in Opposition, Declaration of Anthony Lawrence Shaw (and exhibits ALS-18 and ALS-19 and exhibits ALS-18 and ALS-19) dated and filed Sep. 4, 2019, 14 pages.

Opposition Proceedings No. 2012392760 (Australian Patent Application No. 2012392760 in the name of Liverpool School of Tropical Medicine) filed by Gliknik, Inc. on Jan. 2, 2019, Applicant's Evidence in Answer, Declaration of Sarah Cox (and Exhibit SC1), dated Jul. 2, 2019, and filed Jul. 3, 2019, 36 pages.

Opposition Proceedings No. 2012392760 (Australian Patent Application No. 2012392760 in the name of Liverpool School of Tropical Medicine) filed by Gliknik, Inc. on Jan. 2, 2019, Applicant's Evidence in Answer, Declaration of Dr Beate Peter (and Exhibits BP1-BP9) dated Jul. 2, 2019, and filed Jul. 3, 2019, 147 pages.

Oguchi, et al., "pH Condition in temperature shift cultivation enhances cell longevity and specific hMab productivity in CHO culture." Cytotechnology (Nov. 2006); 52(3): 199-207. Epub Mar. 8, 2007.

Partial European Search Report, EP appl. No. 13169230.3, dated Jul. 31, 2013, 8 pages.

Proceedings of the 126th Annual Meeting of the Pharmaceutical Society of Japan, No. 126 2006, p. 107 (P28[S]am-551) (and Machine translation of pertinent portions), 4 pages.

Reeck, et al., ""Homology" in proteins and nucleic acids: a terminology muddle and a way out of it." Cell (Aug. 1987); 50(5): 667.

Reff and Heard, "A review of modifications to recombinant antibodies: attempt to increase efficacy in oncology applications." Crit. Rev. Oncol./Hematol. (2001); 40: 25-35.

Rowley, et al., "Engineered hexavalent Fc proteins with enhanced Fc-gamma receptor avidity provide insights into immune-complex interactions." Communications Biology (2018); 1: 146, pp. 1-12.

Rudnick and Adams, "Affinity and Avidity in Antibody-Based Tumor Targeting." Cancer Biotherapy and Radiopharmaceuticals (2009); 24 (2): 155-161.

Rütter and Luger, J Am Acad Dermatol. (Jun. 2001); 44(6): 1010-1024.

Salfeld, "Isotype selection in antibody engineering." Nat. Biotechnol. (2007); 25: 1369-1372.

Samuelsson, A., et al., "Anti-inflammatory Activity of IVIG Mediated Through the Inhibitory Fc Receptor." Science (Jan. 2001); 291(5503): 484-486.

Schuurman, et al., "The inter-heavy chain disulfide bonds of IgG4 are in equilibrium with intra-chain disulfide bonds." Mol. Immunol. (2001); 38: 1-8.

Shields, et al., "High Resolution Mapping of the Binding Site on Human IgG1 for FcγRI, FCγRII, FCγRIII, and FcRn and Design of IgG1 Variants with Improved Binding to the FcγR*," J. Biol. Chem. (2001); 276: 6591-6604.

Siragam, et al., "Intravenous immunoglobulin ameliorates ITP via activating Fcγ receptors on dendritc cells." Nature Med. (2006); 12(6):668-692.

Smith, et al., "Addition of a μ-tailpiece to IgG results in polymeric antibodies with enhanced effector functions including complement-mediated cytolysis by IgG4." J. Immunol. (1995); 154: 2226-2236.

Sørensen, et al., "Effect of the IgM and IgA secretory tailpieces on polymerization and secretion of IgM and IgG." The Journal of Immunology (Apr. 1996); 156(8): 2858-2865.

Stegall, et al., "Terminal Complement Inhibition Decreases Antibody-Mediated Rejection in Sensitized Renal Transplant Recipients." American Journal of Transplantation (2011); 11 (11): 2405-2413.

Steger, K., et al., et al., "CHO-S Antibody Titers >1 Gram/Liter Using Flow Electroporation-Mediated Transient Gene Expression followed by Rapid Migration to High-Yield Stable Cell Lines." Journal of Biomolecular Screening (Apr. 2015); 11 (20): 545-551. Epub Dec. 17, 2014.

Stewart, R., et al., "The role of Fc gamma receptors in the activity of immunomodulatory antibodies for cancer." Journal for ImmunoTherapy of Cancer (2014); 2: 29, 10 pages.

Sultan, et al., "Anti-idiotypic suppression of autoantibodies to factor VIII (antihaemophilic factor) by high-dose intravenous gammaglobulin." The Lancet (Oct. 6, 1984); 2(8406): 765-768.

Sun, et al., "Recombinant human IgG1 based Fc multimers, with limited FcR binding capacity, can effectively inhibit complement-mediated disease." Journal of Autoimmunity (Nov. 2017); 84: 97-108. Epub Aug. 19, 2017.

Supplemental European Search Report for European Application No. 08769936.9, dated May 26, 2010, 9 pages.

Thiruppathi, et al., "Recombinant IgG2a Fc (M045) multimers effectively suppress experimental autoimmune myasthenia gravis." J. Autoimmunity (2014); 52 (2): 64-73.

Van Der Meché, et al., "A Randomized Trial Comparing Intravenous Immune Globulin and Plasma Exchange in Guillain-Barré Syndrome." The New England Journal of Medicine (Apr. 23, 1992); 326(17): 1123-119.

Van Noort and Amor, "Cell Biology of Autoimmune Diseases." International Review of Cytology (1998); 178: 127-205.

Vidarsson, et al., "IgG subclasses and allotypes: from structure to effector functions." Frontiers in Immunology (2014); 5 (1): 1-17.

Wei, Xiaoshan et al., "Proteomics studies of autoimmune diseases of the nervous system." Journal of Apoplexy and Nervous Diseases (2009); vol. 26, No. 5, pp. 630-632, and English summary / abstract, 4 pages.

White, D.M., et al., "Design and expression of polymeric immunoglobulin fusion proteins: a strategy for targeting low-affinity Fc gamma receptors." Protein Expression and Purification (Apr. 2001); 21(3): 446-455.

Written Opinion of the International Searching Authority, PCT appln. No. PCT/US2008/065428, 7 pages, dated Feb. 11, 2009.

(56) References Cited

OTHER PUBLICATIONS

Xie, et al., "MicroRNA-127 Inhibits Lung Inflammation by Targeting IgG Fcγ Receptor I." The Journal of Immunology (Mar. 1, 2012); 188(5): 2437-2444. Epub Jan. 27, 2012.

Yoo, et al. "Human IgG2 can form covalent dimers." The Journal of Immunology (2003); 170 (6): 3134-3138.

Zafranskaya, et al., "Interferon-β therapy reduces CD4+ and CD8+ T-cell reactivity in multiple sclerosis." Immunology (May 2007); 121(1): 29-39. Epub Dec. 18, 2006.

European examination report dated May 18, 2011 in co-pending European application No. 08769936.9, 7 pages.

International Preliminary Report on Patentability, dated Jan. 29, 2013 in International application No. PCT/US2011/045768, 10 pages.

International Search Report and Written Opinion for International Application No. PCT/US2011/045768, 15 pages, dated Mar. 8, 2012.

Supplemental European Search Report for European Application No. 11813204.2, dated Jul. 3, 2015, 6 pages.

Bazin, et al., "Reversal of immune thrombocytopenia in mice by cross-linking human immunoglobulin G with a high-affinity monoclonal antibody". Br J Haematol. (Oct. 2006); 135(1): 97-100. Epub Aug. 22, 2006.

Bleeker, et al., "Vasoactive side effects of intravenous immunoglobulin preparations in a rat model and their treatment with recombinant platelet-activating factor acetylhydrolase". Blood (Mar. 1, 2000);95(5): 1856-1861.

Clynes, Raphael, "Immune complexes as therapy for autoimmunity". J. Clin. Invest. (2005); 115(1): 25-27.

Extended European Search Report for European Patent Application No. 17877603.5 dated Dec. 15, 2020, 14 pages.

Siragam, et al., "Can antibodies with specificity for soluble antigens mimic the therapeutic effects of intravenous IgG in the treatment of autoimmune disease?" The Journal of Clinical Investigation (2005); 115 (1): 155-160.

\* cited by examiner

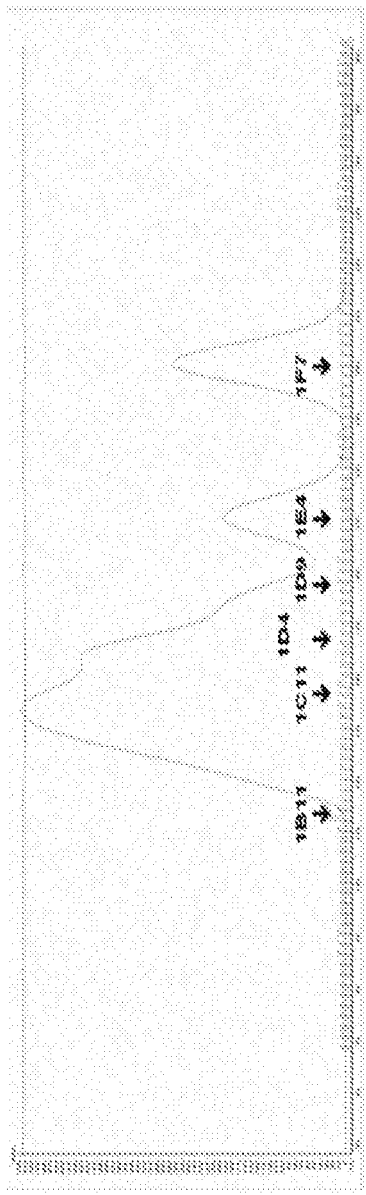
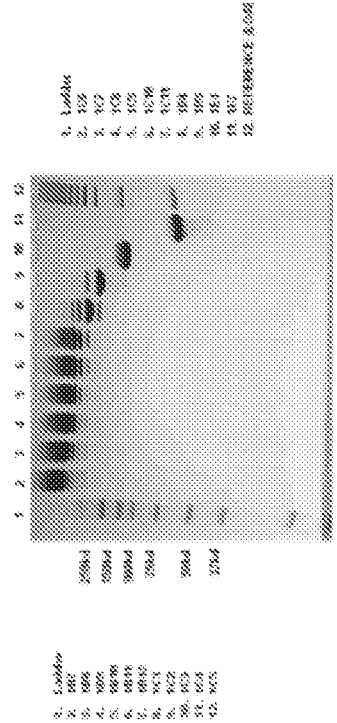
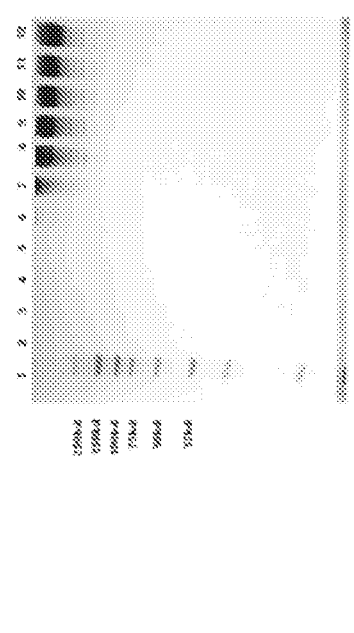
FIG. 5A
FIG. 5B
FIG. 5C

FIG. 13A

PowerCHO3 CD Lonza

| Culture day | Addition order | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| Power Feed A | 1 | | 20 % | | 20 % | | | | | | | | | | | |
| L-Glutamine | 2 | 2mM | | | 2mM | | | | | | | | | | | |
| L-Glutamine | | 1.8g/L | | | 1.7g/L | | | | | | | | | | | |

ADCF-Mab Hyclone

| Culture day | Addition order | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| Hyclone Cell Boost 4 (PS307) | 1 | | | | 5 % | | 5 | | 5 | 5 | | 5 | | 5 | | |
| | | | | | 6.0g/L | | 6.0g/L | | 6.0g/L | 6.0g/L | | 6.0g/L | | 6.0g/L | | |

ActiCHO P media

| Culture day | Addition order | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| Power Feed A | 1 | | | | 4 % | 4 | 4 | 4 | 4 | 4 | 4 | 4 | 4 | | | |
| Power Feed B | 2 | | | | 0.4 % | 0.4 | 0.4 | 0.4 | 0.4 | 0.4 | 0.4 | 0.4 | 0.4 | | | |
| Glucose | 3 | | | | \multicolumn{12}{l|}{Monitor daily and bring the glucose level at 4g/L when below 2g/L} |

FIG. 13B

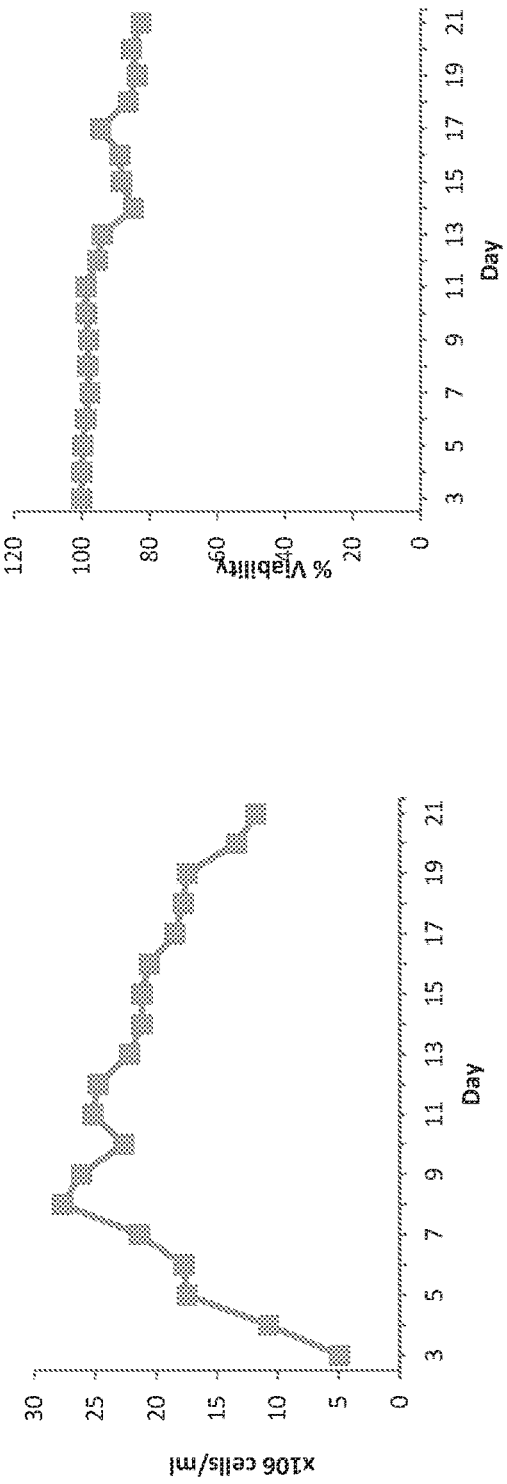
FIG. 21B
FIG. 21A
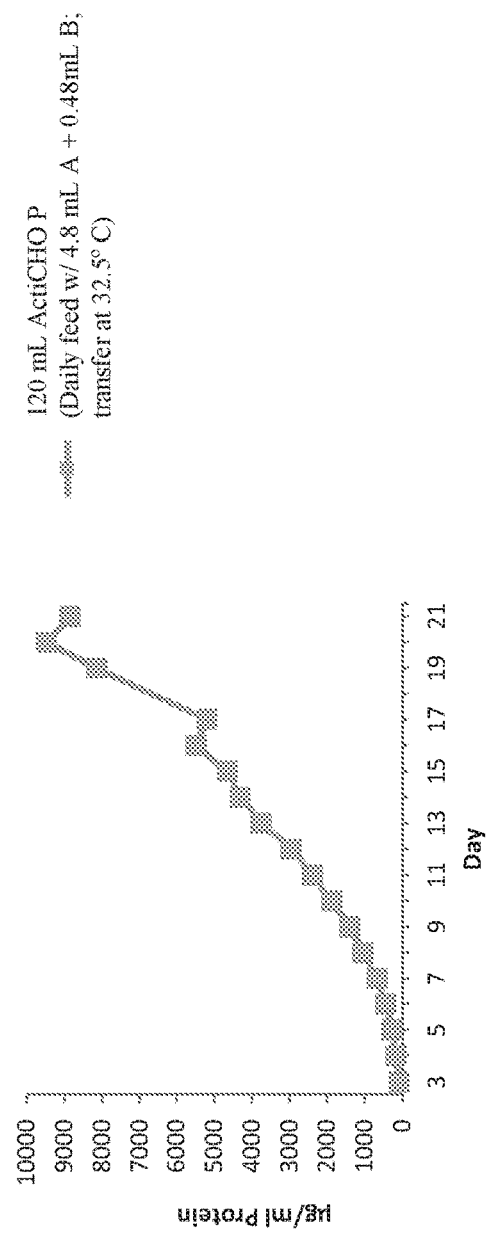
FIG. 21C
120 mL ActiCHO P
(Daily feed w/ 4.8 mL A + 0.48mL B; transfer at 32.5°C)

US 11,155,574 B2

MANUFACTURING OPTIMIZATION OF GL-2045, A MULTIMERIZING STRADOMER

REFERENCE TO RELATED APPLICATIONS

This application is the U.S. national stage application to International Patent Application No.: PCT/US2017/065397, filed Dec. 8, 2017, which claims the benefit of priority to U.S. Provisional Application No. 62/432,402, filed Dec. 9, 2016, the contents of which are incorporated herein by reference its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: GLIK_017_01US_ST25.txt; date recorded: Apr. 15, 2019; file size, 15 kb).

FIELD OF THE INVENTION

This invention relates generally to the fields of immunology, autoimmunity, inflammation, and tumor immunology. More specifically, the present invention relates to optimized methods of manufacturing GL-2045. The invention also relates to novel compositions comprising such optimally manufactured GL-2045, as well as methods of using the GL-2045 compositions. The invention further relates to treating or preventing pathological conditions such as autoimmune diseases and inflammatory diseases.

BACKGROUND OF THE INVENTION

Pooled human intravenous immunoglobulin (IVIG) has been used since the early 1950's to treat immune deficiency disorders and, in more recent decades, autoimmune and inflammatory diseases. IVIG mediates tolerogenic immune effects via several mechanisms including binding of IVIG aggregates to complement C1q and Fc gamma receptors (FcγRs) and cross-linking of these receptors on immune cells such as NK cells (e.g. FcγRIIIa), macrophages (e.g. FcγRIIa), B cells (e.g. FcγRIIb), monocytes, and monocyte-derived cells including dendritic cells. IVIG is a formulation of sterile, purified immunoglobulin G (IgG) products manufactured from pooled human plasma that typically contains more than 90% unmodified IgG, with small and variable amounts of the multimeric immunoglobulins, IgA or IgM (Rutter A et al., J Am Acad Dermatol, 2001, June; 44(6): 1010-1024).

Substantial published data suggest that the small, aggregated IgG fraction of hIVIG, specifically the Fc portion of those aggregates, is disproportionately effective in the treatment of certain diseases mediated by pathologic immune complexes. It has been observed that traces (1-5%) of IgG are present as multimeric forms within IVIG, and IgG dimers can make up 5-15% of hIVIG. Alternatives to IVIG therapy using recombinantly-produced Fc multimers that avidly bind Fc Receptors and complement component C1q, similar to IVIG aggregates, have been described (See US Patent Application Publication Nos. 2010/0239633, US 2013/0156765, US 2015/0218236, and PCT Publication No. WO 2015/132364).

One such Fc multimer, GL-2045, has been previously disclosed (US Patent Application Publication No. 2013/0156765). GL-2045 is a multimerizing general stradomer that is a recombinant mimetic of IVIG. GL-2045 binds most or all of the ligands to which immunoglobulin IgG1 Fc binds. Further, GL-2045 binds with high affinity and avidity to all canonical receptors and to complement C1 q, and has a 10-1,000 fold greater in vitro efficacy compared to IVIG. Additionally, GL-2045, or its murine equivalent, is effective in numerous animal models of autoimmune disease including collagen-induced arthritis, experimental autoimmune neuropathy, idiopathic thrombocytopenic purpura, and experimental autoimmune myasthenia gravis. As such, GL-2045 also has potential clinical utility in treating a wide range of autoimmune diseases, including but not limited to idiopathic thrombocytopenic purpura, chronic inflammatory polyneuropathy, multifocal motor neuropathy, myasthenia gravis, organ transplantation, and rheumatoid arthritis.

In addition to the advantage of GL-2045 over IVIG in potency and efficacy, GL-2045 demonstrates several advantages in the manufacturing process. IVIG is pooled human blood product, meaning that it is derived from the blood of tens of thousands of donors whose serum is then mixed together and subsequently purified to remove viruses and other infectious agents, as well as aggregated IgG. As such, access and supply are limited and production costs are high. Additionally, there is a significant degree of variability between lots of IVIG. Conversely, GL-2045 is recombinantly produced and therefore obviates the difficulties of supply and production costs while providing greater control over the manufacturing process.

The GL-2045 homodimer binds with affinity and without substantial avidity to Fc ligands including Fc gamma receptors and complement C1q. It also naturally forms higher order multimers capable of binding to canonical receptors with avidity. It is these higher-order multimers of GL-2045 that mimic the enhanced efficacy of the multimeric fractions of IVIG. Standard cell culture conditions, however, produce varying levels of cell viability, degrees of multimerized proteins, and protein titers. Therefore, there is a need in the art for methods of manufacturing GL-2045 that results in a defined multimer pattern, and particularly one that results in an increased percentage of higher-order multimers while optimizing cell viability and protein titer.

SUMMARY OF THE INVENTION

The present invention provides for all three of improved cell viability, improved high protein titer, and a surprising and substantial increase in the percentage of higher-order multimers relative to standard manufacturing techniques. This optimized manufacturing method therefore, provides for optimally manufactured GL-2045 compositions with enhanced efficacy for treating inflammatory diseases as compared with non-optimally manufactured GL-2045 compositions. Optimized manufacturing of GL-2045 includes optimized upstream manufacturing methods and, in some embodiments optimized downstream methods. Optimized upstream manufacturing methods a) generate high protein titers, b) maintain high cell viability to minimize cell debris, and c) retain both the highly ordered multimers of the homodimer that are essential for the functioning of GL-2045 and, if desired, the homodimer. Optimized downstream manufacturing methods include various purification techniques that are employed specifically to maintain a selected multimer profile of GL-2045. Thus, in some embodiments, provided herein are GL-2045 compositions with a defined multimer profile.

In some embodiments, a method for producing GL-2045 is provided comprising culturing Chinese Hamster Ovary (CHO) cells that have been stably transfected with an expression vector encoding GL-2045 at 37° C.±1° C. until the CHO cells reach a cell density of about 5 to about 30 million cells/mL; shifting the growth temperature from 37° C.±1° C. to 32.5° C.±P° C.; and harvesting GL-2045 from the culture media. In some embodiments, the cells are grown to a density of about 10 to about 25 million cells/mL prior to the shifting growth temperature. In some embodiments, the cells are grown to a density of about 10 to about 15 million cells/mL prior to the shifting growth temperature. In some embodiments, the cells are grown to a density of about 15 to about 20 million cells/mL prior to the shifting growth temperature. In some embodiments, a dual temperature shift is employed with a shift from 37° C.±1° C. to 34° C.±1° C. on about day 3 with a second temperature shift from 34° C.±1° C. to 31° C.±1° C. on about day 7 of bioreactor culture.

In some embodiments, the CHO cells are cultured in in ActiCHO P base culture media. In some embodiments, the CHO cells are fed during culture with ActiCHO feed A and ActiCHO feed B. In some embodiments, the CHO cells are fed every other day. In some embodiments, the expression vector encoding GL-2045 comprises the leader peptide of SEQ ID NO: 1. In some embodiments, the expression vector encoding GL-2045 further comprises a piggyBac transposase recognition sequence and is transfected with a vector encoding a piggyBac transposase. In some embodiments, the expression vector encoding GL-2045 results in fewer than 20 genomic insertions.

In some embodiments, a recombinantly produced GL-2045 made by the methods described herein is provided. In some embodiments, an expression vector is provided encoding GL-2045 comprising a GL-2045 expression cassette, wherein the GL-2045 expression cassette is flanked by piggyBac minimal inverted repeat elements.

In some embodiments, a method for producing GL-2045 is provided comprising transfecting CHO cells with an expression vector described herein, culturing the CHO cells in a bioreactor with ActiCHO P media at a growth temperature of 37° C.±10, feeding the cultures of CHO cells with Acti CHO Feed A and Acti CHO Feed B daily at a growth temperature of 37° C.±1° C. until the cultures reach a cell density of about 10 million to about 15 million cells/mL, shifting the growth temperature from 37° C.±P° C. to 32.5° C.±P° C., and harvesting GL-2045 from the culture media, wherein the methods result in a cell viability of >80% at Day 21, and a final protein titer of >9,000 mg/mL of which >70% of GL-2045 is present as a multimer, wherein >30% of the multimers are higher order multimers GL-2045. In some embodiments, the cell viability exceeds 95% at day 18 of culture. In some embodiments, the percent of multimers exceeds 80%.

In some embodiments, a method of purifying GL-2045 produced by the methods described herein is provided comprising purifying GL-2045 from the culture supernatant by affinity chromatography and polishing GL-2045 by one or more of cation exchange chromatography, anion exchange chromatography, and hydrophobic interaction chromatography.

In some embodiments, depth filtration is employed prior to affinity chromatography. In some embodiments, the depth filter is the X0HC (Millipore). In some embodiments, the depth filtration unit removes a high percentage of DNA from supernatant. In some embodiments that depth filtration unit is Emphaze™ AEX Hybrid Purifier (3M).

In some embodiments, the affinity chromatography uses a protein A column. In some embodiments, the protein A column comprises an NaOH-resistant resin. In some embodiments, the protein A resin is a MabSelect SuRe resin. In some embodiments, purification by affinity chromatography comprises utilizing one of three different wash buffers to optimize purification conditions. In some embodiments, purification by affinity chromatography comprises eluting GL-2045 from the affinity chromatography column. In some embodiments, eluting GL-2045 comprises elution with a pH gradient. In some embodiments, eluting GL-2045 comprises elution without a pH gradient. In one embodiment, elution is performed using a glycine buffer. In another embodiment, elution is performed using an acetic acid buffer. In some embodiments, the affinity chromatography column is regenerated to remove bound GL-2045. In some embodiments, the affinity chromatography column is regenerated more frequently than suggested by the manufacturer. In some embodiments, the affinity chromatography column is regenerated prior to each purification cycle. In some embodiments, the affinity chromatography column is regenerated with a 0.5 M NaOH buffer.

In some embodiments, polishing GL-2045 comprises anion exchange flow through chromatography. In some embodiments, anion exchange flow through chromatography comprises using a Q Sepharose Fast Flow column. In some embodiments, polishing GL-2045 comprises cation exchange chromatography. In some embodiments, cation exchange chromatography comprises using a POROS XS column. In some embodiments, cation exchange chromatography comprises using a sodium acetate elution buffer. In some embodiments, the elution buffer further comprises 36.5-39.0% of a 1 M NaCl buffer. In one embodiment, the elution method is step elution and in another embodiment the elution is gradient elution. In some embodiments, polishing GL-2045 comprises hydrophobic interaction chromatography. In some embodiments, hydrophobic interaction chromatography comprises using a Butyl FF resin. In some embodiments, hydrophobic interaction chromatography comprises using a Phenyl HP resin. In some embodiments, hydrophobic interaction chromatography ("HIC") comprises using a Phenyl Sepharose 6 Fast Flow High Sub resin. In one embodiment, the HIC method is in flow through mode and in another embodiment the HIC method is in binding mode. In some embodiments, the HIC resin results in isolation of the GL-2045 homodimer. In some embodiments, hydrophobic interaction chromatography comprises using an Octyl FF resin. In some embodiments, the column results in the removal of un-ordered aggregates of GL-2045.

In some embodiments, a method for purifying GL-2045 is provided comprising purifying GL-2045 from the culture supernatant by protein A affinity chromatography, wherein the protein A column uses an alkaline-resistant medium such as the MabSelect SuRe medium, wherein the purification is performed with at least two wash cycles, and wherein clean in place (CIP) procedures are performed after each purification run with a high NaOH regeneration step such as 0.5 M NaOH buffer.

In some embodiments, a method for purifying GL-2045 is provided comprising polishing GL-2045 by cation exchange chromatography, wherein the cation exchange column contains a high-capacity, high-resolution resin such as POROS XS and wherein the elution buffer is a sodium acetate buffer comprised of 36.5-39.0% of a 1 M NaCl buffer. In some embodiments, the method for purifying GL-2045 further comprises polishing GL-2045 by anion exchange chromatography, wherein the anion exchange column contains a strong anion exchange medium that has high chemical stability, allowed clean-in-place and sanitation protocols, such as the Q Sepharose Fast Flow medium. In some embodiments, the method for purifying GL-2045 further comprises polishing GL-2045 by hydrophobic interaction chromatography, wherein the hydrophobic interaction medium is a Butyl FF, a Phenyl HP, or an Octyl FF resin and is selected to isolate or remove a particular fraction of GL-2045 in addition to polishing. In some embodiments, the method for purifying and/or polishing GL-2045 results in a final protein titer of GL-2045>4 g/L after all filtration and chromatography steps (i.e. the final Drug Substance). In some embodiments, the final protein composition of GL-2045 comprises >70% multimers. In some embodiments, >28% of the multimers are higher order multimers as analyzed by analytical SEC-HPLC.

In some embodiments, a purified GL-2045 made by the methods described herein is provided. In some embodiments, the purified GL-2045 made by the methods described herein has a defined multimer pattern that minimizes the percentage of homodimers and/or dimers of the homodimers, or otherwise balances the percentage of homodimers, lower order multimers, higher order multimers, and highest order multimers. In some embodiments, a method of treating or preventing an inflammatory, autoimmune or infections disease or disorder in a subject in need thereof with the recombinantly produced, purified GL-2045 described herein is provided. In some embodiments, the disease or disorder is selected from idiopathic thrombocytopenic purpura, chronic inflammatory polyneuropathy, multifocal motor neuropathy, myasthenia gravis, organ transplantation, and rheumatoid arthritis. In some embodiments, the GL-2045 is administered intravenously, subcutaneously, orally, intraperitoneally, sublingually, bucally, transdermally, via subdermal implant or intramuscularly.

In some embodiments, a recombinantly produced GL-2045 composition is provided, wherein the homodimer fraction of the GL-2045 composition comprises less than about 20% of the total composition. In some embodiments, the homodimer fraction comprises 12-19% of the total composition. In other embodiments, the homodimer fraction comprises 14-19% of the total composition. In some embodiments, the homodimer fraction comprises 15.5-17.5% of the total composition. In another embodiments, the homodimer fraction comprises about 16.2% of the total composition.

In some embodiments, a recombinantly produced GL-2045 composition is provided wherein the dimer of the homodimer fraction of the GL-2045 composition comprises about 7% to about 12%/o of the total composition. In some embodiments, the dimer of the homodimer fraction comprises about 9% to about 11% of the total composition. In other embodiments, the dimer of the homodimer fraction comprises about 10% of the total composition.

In some embodiments, a recombinantly produced GL-2045 composition is provided, wherein the trimer of the homodimer fraction of the GL-2045 composition comprises about 5.5% to about 11% of the total composition. In some embodiments, the trimer of the homodimer fraction comprises about 6.5% to about 8% of the total composition. In other embodiments, the timer of the homodimer fraction comprises about 7% of the total composition.

In some embodiments, a recombinantly produced GL-2045 composition is provided, wherein the tetramer of the homodimer fraction of the GL-2045 composition comprises about 10% to about 16% of the total composition. In some embodiments, the tetramer of the homodimer fraction comprises about 13% to about 15% of the total composition. In other embodiments, the tetramer of the homodimer fraction comprises about 14% of the total composition.

In some embodiments, a recombinantly produced GL-2045 composition is provided wherein the pentamer of the homodimer fraction of the GL-2045 composition comprises about 6% to about 9% of the total composition. In some embodiments, the pentamer of the homodimer fraction comprises about 7% to about 8% of the total composition. In other embodiments, the pentamer of the homodimer fraction comprises about 7% of the total composition.

In some embodiments, a recombinantly produced GL-2045 composition is provided, wherein the hexamer of the homodimer fraction of the GL-2045 composition comprises about 10% to about 14% of the total composition. In some embodiments, the hexamer of the homodimer fraction comprises about 12% to about 13% of the total composition. In other embodiments, the hexamer of the homodimer fraction comprises about 12.7% of the total composition.

In some embodiments, a recombinantly produced GL-2045 composition is provided wherein the highest order multimers (i.e., those in the 7-mer of the homodimer and above fractions) comprise at least about 28% of the total composition. In some embodiments, the highest order multimers comprise no more than about 35% of the total composition. In some embodiments, the highest order multimer fractions comprise from about 300% to about 34% of the total composition. In other embodiments, the highest order multimer fractions comprise about 31.4% of the total composition.

In some embodiments, a recombinantly produced GL-2045 composition is provided wherein
(a) the homodimeric fraction comprises less than about 20% of the total composition;
(b) the highest order multimer fractions comprise at least about 28% of the total composition;
(c) the dimer of the homodimer fraction comprises from about 7% to about 12.5% of the total composition;
(d) the trimer of the homodimer fraction comprises from about 5.5% to about 11% of the total composition;
(e) the tetramer of the homodimer fraction comprises from about 10% to about 16% of the total composition;
(f) the pentamer of the homodimer fraction comprises from about 6% to about 10% of the total composition;
(g) the hexamer of the homodimer fraction comprises from about 10% to about 14% of the total fraction;
(h) the dimer of the homodimer through hexamer of the homodimer fraction comprises from about 40% to about 60% of the total composition;
(i) the trimer of the homodimer through the hexamer of the homodimer fractions comprise from about 32% to about 50% of the total composition;
(j) the tetramer of the homodimer through the hexamer of the homodimer fraction comprise from about 26% to about 39% of the total composition;
(k) the pentamer of the homodimer through the hexamer of the homodimer fraction comprise from about 18% to about 23% of the total composition; or
(l) any combination of (a)-(k).

In some embodiments, a recombinantly produced GL-2045 composition is provided, wherein approximately 80% of the total composition comprises higher order multimers, meaning the dimer of the homodimer and above (i.e., band 2 and above). In some embodiments, approximately 60-80% of the total recombinantly produced GL-2045 composition comprises the trimer of the homodimer and above (i.e., band 3 and above). In some embodiments, about 54-72% of the total of the recombinantly produced GL-2045 composition comprises the tetramer and above (i.e., band 4 and above). In some embodiments, a GL-2045 is provided wherein approximately 44-57% of the total composition comprises the pentamer and above (i.e., band 5 and above). In some embodiments, about 38-51% of the total of the recombinantly produced GL-2045 composition comprises the hexamer and above (i.e., band 6 and above).

In some embodiments, a recombinantly produced GL-2045 is provided wherein bands 2-6 of the composition (i.e., the dimer of the homodimer through the hexamer of the homodimer) comprise about 39-61% of the composition. In some embodiments, a recombinantly produced GL-2045 is provided, wherein bands 3-6 of the composition (i.e., the trimer of the homodimer through the hexamer of the homodimer) comprises about 32-50% of the composition. In some embodiments, a recombinantly produced GL-2045 is provided wherein bands 4-6 of the composition (i.e., the tetramer of the homodimer through the hexamer of the homodimer) comprises about 26-39% of the composition. In some embodiments, a recombinantly produced GL-2045 is provided wherein bands 5-6 of the composition (i.e., the pentamer of the homodimer through the hexamer of the homodimer) comprises about 16-23% of the composition.

BRIEF DESCRIPTION OF THE DRAWINGS

FIG. 5A-FIG. 5C illustrate an elution chromatogram (FIG. 5A) and SDS-Page analysis of GL-2045 for use in an FcγRIIIa binding assay (FIGS. 5B and 5C).

FIG. 13A-FIG. 13B illustrate feeding schedules for PowerCHO3 CD, ADCF-Mab Hyclone, and ActiCHO P media (FIG. 13A), and feeding schedules for Cellvento, BalanCD CHO Growth A, CD FortiCHO Life, and CD4MCHO Hyclone media (FIG. 13B).

FIG. 21A-FIG. 21C illustrate the effects of optimized shake flask conditions on cell density (FIG. 21A), cell viability (FIG. 21B), and GL-2045 protein titer (FIG. 21C).

DETAILED DESCRIPTION OF THE INVENTION

Figure 1A:
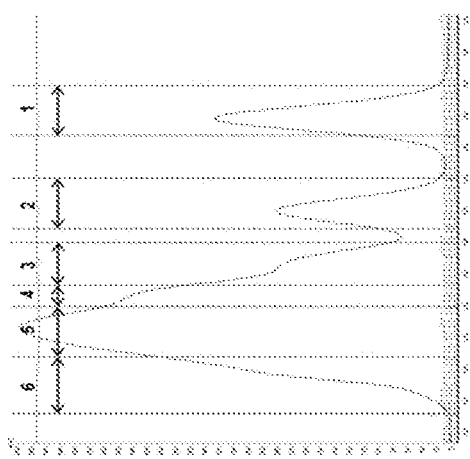
FIG. 1A-FIG. 1B illustrate GL-2045 fractionation by size exclusion chromatography (FIG. 1A) and analysis of the resulting fractions by non-reducing gels (FIG. 1B).

The approach to production of optimized recombinant GL-2045 described herein includes optimized upstream manufacturing methods that result in enhanced GL-2045 multimerization while optimizing cell viability and protein titer. In some embodiments, the optimized state is carried through to drug substance by optimized downstream manufacturing. Further, provided herein are compositions comprising GL-2045 with a defined multimer pattern. The compositions provided herein have utility for treating autoimmune disease, inflammatory disease, allergy, antibody-mediated disease, and complement-mediated disease.

As used herein, "drug substance" refers to the final dosage form of GL-2045 as sold by the manufacturer.

As used herein, the use of the word "a" or "an" when used in conjunction with the term "comprising" in the claims and/or the specification may mean "one," but it is also consistent with the meaning of "one or more," "at least one," and "one or more than one."

As used herein, the terms "biomimetic", "biomimetic molecule", "biomimetic compound", and related terms refer to a human made compound that imitates the function of another compound, such as pooled human Intravenous Immunoglobulin ("hIVIG"), a monoclonal antibody or the Fc fragment of an antibody. "Biologically active" biomimetics are compounds which possess biological activities that are the same as or similar to their naturally occurring counterparts. By "naturally occurring" is meant a molecule or portion thereof that is normally found in an organism. By naturally occurring is also meant substantially naturally occurring. "Immunologically active" biomimetics are biomimetics which exhibit immunological activity the same as or similar to naturally occurring immunologically active molecules, such as antibodies, cytokines, interleukins and other immunological molecules known in the art. In preferred embodiments, the biomimetics of the present invention are optimized multimerized stradomers, as defined herein (e.g. optimally manufactured GL-2045).

By "directly linked" is meant two sequences connected to each other without intervening or extraneous sequences, for example, amino acid sequences derived from insertion of restriction enzyme recognition sites in the DNA or cloning fragments. One of ordinary skill in the art will understand that "directly linked" encompasses the addition or removal of amino acids so long as the multimerization capacity is substantially unaffected.

By "homologous" is meant identity over the entire sequence of a given nucleic acid or amino acid sequence. For example, by "80% homologous" is meant that a given sequence shares about 80% identity with the claimed sequence and can include insertions, deletions, substitutions, and frame shifts. One of ordinary skill in the art will understand that sequence alignments can be done to take into account insertions and deletions to determine identity over the entire length of a sequence.

It has been described that hIVIG binds to and fully saturates the neonatal Fc receptor (FcRn) and that such competitive inhibition of FcRn may play an important role in the biological activity of hIVIG (e.g. F. Jin et al., Human Immunology, 2005, 66(4)403-410). Since immunoglobulins that bind strongly to Fcγ receptors also bind at least to some degree to FcRn, a skilled artisan will recognize that stradomers capable of binding to more than one Fcγ receptor will also bind to and may fully saturate the FcRn.

There are two human polymorphs of IgG1, termed DEL and EEM polymorphs. The DEL polymorph has a D at position 356 and an L at position 358; the EEM polymorph has an E at position 356 and an M at position 358 (Kabat numbering, SEQ ID NOs: 2 and 3, EEM and DEL polymorphs, respectively). The stradomers provided herein may comprise either the DEL or the EEM IgG1 polymorph. Thus, even if a sentence for a particular mutant is explicitly produced in the context of the DEL polymorphism, one of skill in the art will understand that the same mutations may be made to the EEM polymorph to yield the same results.

US 2010/0239633 discloses using linked immunoglobulin Fc domains to create orderly multimerized immunoglobulin Fc biomimetics of hIVIG (biologically active ordered multimers known as stradomers), which include short sequences including restriction sites and affinity tags between individual components of the stradomer, for the treatment of pathological conditions including autoimmune diseases and other inflammatory conditions. See US 2010/0239633, incorporated by reference in its entirety. US 2013/0156765 discloses stradomers wherein the individual components are directly linked, rather than separated by restriction sites or affinity tags. US 2013/0156765 also specifically discloses a multimerizing stradomer (GL-2045) comprising an IgG1Fc domain with an IgG2 hinge multimerization domain directly linked to its C-terminus, which exhibits enhanced multimerization and complement binding relative to the N-terminal linked construct (e.g., GL-2019, described in US 2010/0239633). See US 2013/0156765, incorporated by reference in its entirety. The structure of GL-2045 is: IgG1 Hinge—IgG1CH2 IgG1 CH3—IgG2 Hinge and GL-2045 is provided as SEQ ID NO: 4 and 5 (EEM and DEL polymorphs, respectively).

Stradomer Unit Monomer

As used herein, the term "stradomer unit monomer" refers to a single, contiguous peptide molecule that, when associated with at least a second stradomer unit monomer, forms a homodimeric "stradomer unit" comprising at least one Fc domain, and in the case of GL-2045 an IgG2 hinge multimerization domain. In preferred embodiments, stradomer units of GL-2045 are comprised of two associated stradomer unit monomers. However, a GL-2045 stradomer may also contain three or more stradomer unit monomers.

The optimally manufactured stradomer of the current invention (optimally manufactured GL-2045) contains a direct linkage between the N-terminus of the IgG1 Fc monomer and the C terminus of a leader peptide (SEQ ID NO: 1) and the C terminus of the IgG1 Fc and the N terminus of the multimerization domain IgG2 hinge (SEQ ID NO: 6).

As a clarifying example, the skilled artisan will understand that the optimally manufactured stradomer molecules of the present invention may be constructed by preparing a polynucleotide molecule that encodes an Fc domain monomer and a multimerizing region. Such a polynucleotide molecule may be inserted into an expression vector, which can be used to transform a population of bacteria or transfect a population of mammalian cells. Stradomer unit monomers can then be produced by culturing the transformed bacteria or transfected mammalian cells under appropriate culture conditions. For example, a clonal cell line continuing a pool of stably transfected cells can be achieved by selecting cells with genetecin/G418. Alternatively, cells can be transiently transfected with DNA encoding the optimally manufactured stradomer of the current invention (e.g. DNA encoding the stradomer according to SEQ ID NO: 4 or 5) under the control of the CMV promoter. The expressed stradomer unit monomers can then form functional stradomer units and stradomers upon either self-aggregation of the stradomer monomers or units or association of stradomer monomers using inter-stradomer monomer linkages. The expressed stradomers can then be purified from the cell culture media by downstream manufacturing methods described herein (e.g., affinity chromatography, ion-exchange chromatography, and/or hydrophobic interaction chromatography). One of skill in the art will understand that the leader peptide included in the nucleic acid construct is used only to facilitate production of the stradomer unit monomer peptides and is cleaved upon expression of the mature protein. Thus, the biologically active biomimetics of the present invention do not comprise a leader peptide.

Cluster Stradomer

In one embodiment, the optimally manufactured GL-2045 made in accordance with the present disclosure is a cluster stradomer. A "cluster stradomer" is a biomimetic that has a radial form with a central moiety "head" and two or more "legs", wherein each leg comprises one or more Fc domains that is capable of binding at least one Fc gamma receptor and/or complement. A cluster stradomer is also known as a "multimerizing stradomer" by virtue of the presence of a multimerization domain that results in multimerization of the stradomer. Thus, serial stradomers which contain multiple Fc domains on one stradomer monomer molecule may still be classified as a cluster stradomer or multimerizing stradomer so long as the molecule also contains at least one multimerization domain. Each cluster stradomer is comprised of more than one homodimeric protein, each called a "cluster stradomer unit." Each cluster stradomer unit is comprised of at least one region that multimerizes and a "leg" region that comprises at least one functional Fc domain. The multimerizing region creates a cluster stradomer "head" once multimerized with another cluster stradomer unit. The leg region may be capable of binding as many complement molecules as there are Fc domains in each leg region. For example, the leg region may bind as many C1q molecules as there are Fc domains in each leg region. Thus a cluster stradomer is a biomimetic compound capable of binding two or more C1 q molecules, thus preventing complement-mediated lysis also known as Complement Dependent Cytotoxicity (CDC).

The multimerizing region contained within the optimally manufactured stradomer of the current invention is the IgG2 hinge region. As is known in the art, the hinge region of human IgG2 can form covalent dimers (Yoo, E. M. et al. J. Immunol. 170, 3134-3138 (2003): Salfeld Nature Biotech. 25, 1369-1372 (2007)). The dimer formation of IgG2 is potentially mediated through the IgG2 hinge structure by C—C bonds (Yoo et al 2003), suggesting that the hinge structure alone can mediate dimer formation. The amount of IgG2 dimers found in human serum, however, is limited. It is estimated that the amount of IgG2 existing as a dimer of the homodimer is less than 10% of the total IgG2 (Yoo et al. 2003). Furthermore, there is no quantitative evidence of the multimerization of IgG2 beyond the dimer of the homodimer. (Yoo et al. 2003). That is, native IgG2 has not been found to form higher order multimers in human serum. The IgG2 hinge-containing stradomers (e.g., optimally manufactured GL-2045) are present as higher-order multimers and, unlike native IgG2 in human serum in which the IgG2 hinge interactions are variable and dynamic, GL-2045 has been demonstrated to form highly stable multimers evidenced on non-reducing SDS-PAGE gels, analytical ultracentrifugation, and 3-month stability studies at 100% humidity at 37° C. Furthermore, it is also surprising that the amount of multimers in the IgG2 hinge-containing stradomer preparations are significantly higher than the approximately 10% of dimers and no multimers observed for IgG2 in human serum. For example, the percent of stradomers that are multimers, including dimers, trimers, tetramers and higher order multimers of the homodimer exceeds 20% and may exceed 30%, 40%, 50%, 60%, 70%, 80%, or even 90%. In an especially preferred embodiment, the percent of GL-2045 present as a homodimer is between 10 and 20% and the corresponding percent of GL-2045 present as highly ordered multimers of the homodimer is greater than 70%.

The amino acid sequence GL-2045 is described in SEQ ID NO: 4 and 5.

The term "isolated" polypeptide or peptide as used herein refers to a polypeptide or a peptide which either has no naturally-occurring counterpart or has been separated or purified from components which naturally accompany it, e.g., in tissues such as pancreas, liver, spleen, ovary, testis, muscle, joint tissue, neural tissue, gastrointestinal tissue, or breast tissue or tumor tissue (e.g., breast cancer tissue), or body fluids such as blood, serum, or urine. Typically, the polypeptide or peptide is considered "isolated" when it is at least 70%, by dry weight, free from the proteins and other naturally-occurring organic molecules with which it is naturally associated. Preferably, a preparation of a polypeptide (or peptide) of the invention is at least 80%, more preferably at least 90%, and most preferably at least 99%, by dry weight, the polypeptide (peptide) of the invention. Since a polypeptide or peptide that is chemically synthesized is inherently separated from the components that naturally accompany it, the synthetic polypeptide or peptide is "isolated."

An isolated polypeptide (or peptide) of the invention can be obtained, for example, by expression of a recombinant nucleic acid encoding the polypeptide or peptide or by chemical synthesis. A polypeptide or peptide that is produced in a cellular system different from the source from which it naturally originates is "isolated" because it will necessarily be free of components which naturally accompany it. In a preferred embodiment, the isolated polypeptide of the current invention contains only the sequences corresponding to the IgG1 Fc monomer and the IgG2 hinge multimerization domain (SEQ ID NO: 6), and no further sequences that may aid in the cloning or purification of the protein (e.g., introduced restriction enzyme recognition sites or purification tags). The degree of isolation or purity can be measured by any appropriate method, e.g., column chromatography, polyacrylamide gel electrophoresis, or HPLC analysis.

Manufacturing Methods

GL-2045 forms ordered multimers of the homodimer and is active in the homodimer and all of the multimer fractions. It is critical to GL-2045 function that the manufacturing processes result in an optimized multimer profile. As used herein, "optimized multimer profile" or "optimized multimerization profile" refers to the combination of homodimers and highly ordered multimers of GL-2045 that results in the desired biological outcome for GL-2045 as an IVIG mimetic (e.g., enhanced binding to C1q with initial activation of the complement system, and/or subsequent inhibition of complement activation and prevention of CDC, for example without being limited by theory, at the level of C3/C3b). A skilled artisan will recognize that it may be advantageous to isolate various multimer fractions from the optimally manufactured GL-2045 as a separate product, either alone or combined with other elements, including for other therapeutic purposes. For example, as provide in the Examples, the larger multimer fractions of GL-2045 are more active than smaller multimer fractions in binding to C1q and modulating downstream complement-mediated effector function and at binding low affinity FcγRs. The methods of the present invention are thus directed to not only GL-2045 compositions comprising the optimized multimer profile, but also to GL-2045 compositions comprising only select multimers based on the desired effector function. In such embodiments, the optimized multimer profile of GL-2045 that results in one desired biological outcome may differ from the optimized multimer profile that results in another desired biological outcome.

Without being bound by theory, it is thought that the homodimer serves as a receptor and ligand buffer, similar to unaggregated IgG1. The higher order multimers bind with increasing avidity to low affinity Fcγ receptors and to complement factors (e.g. C1q, which is hexameric) and, as described herein, demonstrate enhanced biological efficacy compared to homodimers or lower order multimers (e.g., dimers, trimers, and/or tetramers of the GL-2045 homodimer). Therefore, the degree of multimerization is a critical upstream and downstream manufacturing consideration in the production of clinically efficacious GL-2045. As such, it is not only desirable to maintain optimal cell viability, high protein titer, and optimal multimerization profiles of GL-2045 through optimized upstream manufacturing methods, but also to maintain and/or enhance optimal multimerization profiles of GL-2045 through optimized downstream manufacturing methods.

In some embodiments, optimized manufacturing methods described herein result in a GL-2045 protein composition in which at least 70% or at least 80% of GL-2045 is present as non-homodimers (e.g., dimers of the homodimer, trimers of the homodimer, etc.). In some embodiments, greater than 70% or greater than 80% of GL-2045 is present as non-homodimers. For example, optimized manufacturing methods may result in a GL-2045 protein composition wherein 80%, 85%, 90%, 95%, or greater of the GL-2045 is present as non-homodimers. In some embodiments, the protein composition comprises at least 28% or at least 30% of GL-2045 present as the highest order multimers (i.e. 7-mers of the homodimer and above). In some embodiments, the protein composition comprises no more than 35% of GL-2045 present as the highest order multimers. In some embodiments, the protein composition comprises at least about 35% of GL-2045 present as tetramers, pentamers, hexamers, and 7-mers (i.e., at least 35% of the total GL-2045 composition is comprised of fractions 4-6). In some embodiments, at least about 35% of GL-2045 is present as trimers of the homodimer and above (i.e., at least 35% of the total GL-2045 composition is comprised of fraction 3 and above). In some embodiments, at least about 35% of GL-2045 is present as trimers, tetramers, pentamers, or hexamers of the homodimer (i.e., at least 35% of the total GL-2045 composition is comprised of fraction 3-6). In some embodiments, at least about 35% of GL-2045 is present as tetramers of the homodimer and above (i.e., at least 35% of the total GL-2045 composition is comprised of fraction 4 and above). In some embodiments, at least about 35% of GL-2045 is present as tetramers and pentamers of the homodimer (i.e., at least 35% of the total GL-2045 composition is comprised of fractions 4 and 5). In some embodiments, at least about 35% of GL-2045 is present as pentamers of the homodimer and above (i.e., at least 35% of the total GL-2045 composition is comprised of fraction 5 and above). In some embodiments, at least about 35% of GL-2045 is present as pentamers and hexamers of the homodimer (i.e., at least 35% of the total GL-2045 composition is comprised of fraction 5 and 6). In some embodiments, at least about 35% of GL-2045 is present as hexamers of the homodimer and above (i.e., at least 35% of the total GL-2045 composition is comprised of fraction 6 and above). In some embodiments, at least about 35% of GL-2045 is present as 7-mers of the homodimer and above (i.e., at least 35% of the total GL-2045 composition is comprised of fraction 7 and above). For example, the optimized manufacturing methods described herein may result in a GL-2045 protein composition wherein 40%, 45%, 50%, 55%, or greater of the GL-2045 is present as pentamers of the homodimer and above. Current manufacturing methods for Fc-containing therapeutics (e.g., monoclonal antibodies) have focused on increased protein titer and yield through the downstream filtration steps. These methods do not generally consider the effects of the manufacturing process on the multimerization of the Fc-containing protein and, in stark contrast to the methods described herein, seek to minimize protein aggregation and multimerization. Surprisingly, culture conditions that result in the highest protein yields of GL-2045 do not necessarily result in the highest percentage of GL-2045 present as multimers. As such, the data described herein demonstrates that manufacturing variables that affect total protein titer are, at least in part, independent from variables affecting multimerization profiles. Therefore, a person of skill in the art would not be able to predict which upstream manufacturing conditions would affect GL-2045 multimerization based on the current state of the art.

For example, established protocols for recombinant protein production with Chinese hamster ovary (CHO) cells provide for a temperature shift from 37° C. to 31° C. on a specific day of culture (Ouguchi et al, Cytotechnology, 52(3), pp. 199-207, (2006); Masterson and Smales, Pharmaceutical Bioprocessing, 2(1), pp. 49-61, (2014)). However, the present inventors found that, in contrast to what was described in Ouguchi, et al., a temperature shift from 37° C. to 32.5° C. resulted in maintenance of cell density and high cell viability while optimizing for protein titer. Further, the inventors found that shifting the temperature based on cell density, rather than on a given day of culture as previously described, resulted in enhanced GL-2045 protein titers of nearly 10 g/L.

Furthermore, the present inventors have discovered that maintenance of the optimized multimerization profile resulting from optimized upstream manufacturing methods relies in part on optimized downstream manufacturing methods (e.g., affinity chromatography and/or ion-exchange chromatography). Monoclonal antibody (mAb) and Fc fusion protein filtration and purification techniques are extensively described and commonly used. However, when applied to GL-2045, these techniques result in unpredictable modifications of the GL-2045 multimerization profile. For example, the present inventors have surprisingly discovered that most protein A columns are not suitable for purifying GL-2045, despite their routine use in purifying mAb and Fc fusion proteins, as demonstrated in Example 8. protein A is an extremely expensive reagent, costing millions of dollars for use in compliance with good manufacturing practices (GMP) purification of a single drug, and needing to be re-used as many as 100 or more times in order to be economically viable. Like mAbs and Fc fusion proteins, GL-2045 binds protein A; however, unlike mAbs and Fc fusion proteins, GL-2045 does not completely dissociate from protein A with normal elution steps due to the avid binding of GL-2045 to protein A. The present inventors have unexpectedly discovered that utilization of protein A columns for the purification of GL-2045, wherein the optimal multimerization profile is maintained, requires a more frequent column cleaning schedule.

The present inventors have further discovered that protein A column Clean-in-Place (CIP) procedures commonly used in the art unexpectedly result in a change in the GL-2045 multimerization profile. Normal CIP procedures entail column cleaning at the end of a purification run, which may involve numerous cycles of protein supernatant passing through the column. However, the present inventors have discovered that the high avidity of GL-2045 results in a lack of GL-2045 dissociation from protein A. Consequently, the binding sites of protein A remain occupied, preventing GL-2045 binding in subsequent cycles and resulting in a loss of the homodimer. Therefore, in contrast to protocols utilized with mAbs or Fc fusion protein, the present inventors have unexpectedly discovered that with GL-2045, CIP cleaning of Protein A columns must be done more frequently than is done with a monoclonal antibody or Fc fusion protein and with a highly stringent regeneration buffer, such as 0.5 M NaOH.

pH elution gradients are commonly used with protein A columns to optimize protein yield during purification. The present inventors have surprisingly discovered that pH elution gradients used in the art to optimize protein A column yields of monoclonal antibodies or Fc fusion proteins can cause an undesired loss of homodimer or higher order multimer components of GL-2045, thus changing the multimerization profile of GL-2045 (demonstrated in Example 10). As such, the present inventors have also determined a means of using the elution gradient technique to optimize the combination of yield and multimerization of GL-2045. Additionally, the present inventors have surprisingly discovered that pH elution gradient can be applied to protein A column for a novel purpose, namely to separate the largest, highly ordered GL-2045 multimers from homodimer aggregates (as demonstrated in Example 11).

The present inventors have also discovered that when using ion exchange columns commonly used in the art to purify monoclonal antibodies and Fc fusion proteins, such as anion exchange and cation exchange, changes in pH and/or salt can change the multimerization profile of GL-2045, as demonstrated in Example 12. This stands in stark contrast to a monoclonal antibody or Fc fusion protein where changes in salt or pH may result in the loss of a small amount of protein but no change to the composition of the drug. Additionally, the present inventors have surprisingly discovered that adjustments of salt and/or pH can be used for a novel purpose, to separate the largest, highly ordered GL-2045 multimers from aggregates of homodimer that may be of similar molecular mass. As demonstrated in Example 13, the inventors use a functional assay to prove that removal of disordered aggregates from the highest order multimer fractions is associated with higher potency and a more highly purified GL-2045 product.

Hydrophobic interaction (HIC) columns are commonly used in the art to purify monoclonal antibodies and Fc fusion proteins through a variety of mechanisms including high-yield capture, polishing monoclonal antibodies, removing truncated species from full-length forms, separating active from inactive forms, and clearing of viruses. However, when used in the context of GL-2045, the inventors have found that standard HIC columns are unpredictable. As demonstrated in Example 14, 7 HIC columns comprised of different matrices are associated with widely differing capture rates, ranging from 16% to 62%, despite the same supernatant and the same buffer being used with all columns.

Further, the present inventors predict that changes in buffer can change the multimerization profile of GL-2045. This stands in stark contrast to a monoclonal antibody or Fc fusion protein where changes in buffer would result in the loss of a small amount of protein or less perfect polishing but no change to the fundamental composition of the drug.

Furthermore, the present inventors have discovered that because the GL-2045 homodimer is comprised of IgG1 Fc and a multimerizing domain that causes highly ordered multimers to be formed, GL-2045 binds avidly to all or nearly all the many ligands and targets that bind without avidity to a native IgG1 Fc homodimer. This includes, not surprisingly, all the low affinity Fc receptors and complement C1q as well as protein A and protein G used commonly in purification columns. However, this avid binding also results in less desirable potential target binding, for example, endotoxin. For this reason, the present inventors have determined that a multiple step purification process is desirable, including purification of GL-2045 by protein A, and polishing of protein A-purified GL-2045 by at least one or more of cation exchange chromatography, anion exchange flow through, and hydrophobic interaction columns. In a preferred embodiment, a four-step purification process is desirable, including purification of GL-2045 by protein A, and polishing of protein A-purified GL-2045 by all three of cation exchange chromatography in binding mode, anion exchange in flow through mode, and hydrophobic interaction columns in either binding or flow through mode. This four-step purification process is outlined in Example 15. One of skill in the art will readily understand that additional filtration steps, including depth filtration and ultrafiltration steps may be added at any point, before, during, or after the process described in Example 15 to further purify the GL-2045 composition.

Upstream Manufacturing

Generally speaking, upstream manufacturing methods are methods in which biological materials are inoculated and grown in culture, under controlled conditions, to manufacture certain types of protein biological products (e.g. GL-2045). As used herein "upstream manufacturing methods" specifically refers to methods for recombinant production of a protein without reference to subsequent purification and filtration steps that are generally categorized as downstream manufacturing methods. Upstream manufacturing methods with alterations or changes aimed at optimization of a specific protein characteristic (e.g. multimerization efficiency) are referred to herein as "optimized upstream manufacturing methods," Several aspects of upstream protein manufacturing may be optimized (e.g., changed or altered to achieve a desired result) to result in a final protein product with specific characteristics. Aspects of upstream recombinant protein production that may be optimized can include, but are not limited to, composition of the expression vector encoding the protein, cell type, basal media, media additives including feeds, feed schedule, passage schedule, culture temperature, temperature shift, humidity, degree of aeration, pH, seeding cell density, $CO_2$ level, and/or oxygen level. In some embodiments, the optimized upstream manufacturing methods described herein result in the production of a high titer of GL-2045 with an increased percentage of higher order multimers compared to GL-2045 produced by non-optimized upstream manufacturing methods.

In some aspects of the invention, Chinese hamster ovary (CHO) cells are transfected with an expression vector encoding GL-2045. In some aspects, insertion of the GL-2045 expression cassette into the genome is mediated by the piggyBac transposon, wherein the GL-2045 expression cassette is flanked by piggyBac minimal inverted repeat elements. Co-expression of this GL-2045 expression vector with a vector encoding a piggyBac transposase mediates gene integration into regions of the genome that are actively transcribed, resulting in the generation of cell lines with stable and enhanced gene expression compared to standard transfection methods (See US 2010/0311116 and Matasci et al, Biotechnol. Bioeng. V. 108, pp 2141-2140, (2011), herein incorporated by reference). The piggyback system normally increases protein production due, at least in part, to a high number of integrated transgenes. However, the present inventors selected a high titer, high viability clonal cell line wherein the transgene insertion rate was relatively low (e.g., approximately 11 copies determined by UV spectrophotometry); however one of skill in the art would understand that the use of selective antibiotic pressure also allows for the use of transgene insertion rates of greater than about 50 inserted copies or more than about 100 inserted copies. In some aspects, the expression vector comprises a nucleic acid encoding a leader peptide (e.g. SEQ ID NO: 1). In some aspects, the expression vector further comprises an antibiotic resistance gene to allow for the selection of successfully transfected CHO cells. In some aspect of the invention, successfully transfected CHO cells are generated in the absence of antibiotic selection (See US 2010/0311116). In some aspects, the expression vector further comprises a transcriptional promoter to promote high level expression of GL-2045 (e.g. a CMV promoter).

In some embodiments, CHO cells transfected with a GL-2045 expression vector are cultured in a bioreactor. In some embodiments, the CHO cell line, of which there are many variants, is carefully selected so that once stably transfected with a GL-2045 expression vector using techniques that cause insertion preferentially at transcriptionally active sites. In some embodiments, the culture conditions applied to said transfected select CHO cell line allows for the culture protocol to continue longer than by standard manufacturing methods without adversely affecting cell viability. Standard manufacturing methods can average 12 days in a bioreactor, at which point there is a decrease in cell viability due to an increase in cellular debris present in the culture. In addition to being associated with a loss of cell viability, cellular debris dramatically increases challenges associated with filtration and purification. In some embodiments of the present invention, cells are seeded in a bioreactor at a predetermined cell density and cultured for >12 days. In some embodiments, the cells are cultured in the bioreactor with acceptable viable cell density for 13, 14, 15, 16, 17, 18, 19, 20, 21, or more days.

In some embodiments, ActiCHO P is used as the basal media for optimized upstream manufacturing of optimally manufactured GL-2045. The terms "ActiCHO P" and "optimized media," as used interchangeably herein, refer to the commercially available ActiCHO® base media ("ActiCHO P," GE Healthcare), any substantial copies thereof, or media that comprises substantially the same constituents in substantially the same quantities as ActiCHO P. ActiCHO P has also recently been marketed by GE as Hyclone "ActiPro," a nearly identical product to ActiCHO P and which is an equivalent reagent for the purposes of these disclosures. In some embodiments, ActiCHO® Feed A and Feed B (also recently marketed by GE as Hyclone "Cell Boost 7a" and Hyclone "Cell Boost 7b," which are identical products to ActiCHO® Feed A and Feed B and are equivalent reagents for the purposes of this disclosure) are used in addition to the basal media. The terms "ActiCHO Feed A" or "optimized feed A," as used interchangeably herein and "ActiCHO Feed B" or "optimized feed B", as used interchangeably herein refer to the commercially available ActiCHO Feeds (GE Healthcare), substantial copies thereof, or feeds that comprise substantially the same constituents in substantially the same quantities as ActiCHO Feed A and/or ActiCHO Feed B. In some aspects of the invention, CHO cells transfected with a GL-2045 expression vector are fed with ActiCHO Feed A and Feed B every day. In some aspects of the invention, CHO cells transfected with a GL-2045 expression vector are fed with ActiCHO Feed A and Feed B every other day. In some aspects of the invention, CHO cells transfected with a GL-2045 expression vector are fed with ActiCHO Feed A and Feed B via continuous feed.

In some embodiments of optimized upstream manufacturing methods, CHO cells transfected with a GL-2045 expression vector are grown to a specific cell density prior to shifting the temperature. In some aspects, the CHO cells are grown to a density of about 5-30 million cells/mL prior to shifting the temperature. In some aspects, the cells are grown to a density of about 6, 7, 8, 9, 10, 15, 20, 25, or about 30 million cells/mL prior to shifting the temperature. In some aspects, CHO cells are grown to a density of about 10-25 million cells/mL prior to shifting the temperature. In some aspects of optimized manufacturing methods, CHO cells are grown to a density of about 10-15 million cells/mL prior to shifting the temperature.

In some embodiments, CHO cells transfected with a GL-2045 expression vector are cultured at 37° C.±1° C. until reaching a predetermined cell density. In some aspects, the temperature is shifted to 32.5° C.±1° C. after the cells reach a predetermined cell density. This aspect is in contrast to previously described culture methods for recombinant protein production, wherein cells are cultured at 37° C. for a predetermined number of days, after which the temperature is often shifted to 31° C. (Ouguchi et al, Cytotechnology, 52(3), pp. 199-207, (2006), Masterson and Smales, Pharmaceutical Bioprocessing, 2(1), pp. 49-61, (2014)). The present inventors have determined that shifting the temperature from 37° C.±1° C. to 32.5° C.±1° C. based on cell density, rather than culture time, unexpectedly provides the combination of increased viability, improved cell density, and a substantial increase in protein titer relative to standard upstream manufacturing methods. In some embodiments, CHO cells transfected with a GL-2045 expression vector are subjected to a double temperature shift. In one embodiment, transfected CHO cells are cultured at 37° C.±1° C. and shifted to 34° C.±1° C. before reaching peak viable cell density. In a preferred embodiment, this temperature shift occurs while the CHO cells remain in log growth phase. In an especially preferred embodiment, the initial temperature shift occurs on day 3 or 4 of culture. In another embodiment, transfected CHO cells are cultured at 37° C.±1° C. until reaching a predetermined cell density, at which time the temperature is shifted to 34° C.±1° C. In a preferred embodiment, the cell density is between 5-20 million cells/ml at the first temperature shift. In an especially preferred embodiment, the cell density is between 8-15 million cells/ml at the first temperature shift. In some embodiments, the second temperature shift occurs at day 7±1 day. In some embodiments, the temperature is then further shifted to 31° C. In some embodiments, this second temperature shift is performed at about day 4 post initial temperature shift.

Downstream Manufacturing Methods

In some embodiments, harvesting of GL-2045 is accomplished by downstream manufacturing methods. In some embodiments, downstream manufacturing methods are employed in combination with the optimized upstream manufacturing methods described herein to remove or isolate a specific protein fraction (e.g., removal of unordered high molecular weight aggregates of the homodimer GL-2045). As used herein, "downstream manufacturing methods" are protein purification and filtration steps performed on protein supernatants to generate a protein composition of a desired purity and/or concentration. In some embodiments, downstream manufacturing methods have been optimized for the purification and filtration of GL-2045 to result in and/or maintain a particular multimerization profile of GL-2045, referred to herein as "optimized downstream manufacturing methods."

In some embodiments, GL-2045 is purified by affinity chromatography. In some embodiments, GL-2045 is purified using protein A columns. As described above, protein A columns are very expensive and are reused a considerable number of times in order to become economically viable. The re-use of protein A columns necessitates "regenerating" the protein A column in order to maintain protein binding capacity. As used herein "regenerating" or "regenerate" refers to the removal of bound protein from the protein A column that was not removed during the elution process. In some embodiments, the protein A column must be regenerated more often during GL-2045 purification than indicated in the manufacturer instructions or more often than is normal in the art for purifying monoclonal antibodies or Fc fusion proteins. In some embodiments, the protein A column must be regenerated at least twice as often as recommended by the manufacturer. In further embodiments, the protein A column must be regenerated in between each successive round of passing of GL-2045 supernatant over the column. In such embodiments, purification of GL-2045 with a protein A affinity column necessitates the use of a high stringent regeneration buffer to remove avidly bound GL-2045 multimers from the protein A column and regenerate the full binding capacity of the protein A column. In preferred embodiments, the high stringent regeneration buffer does not cause degradation of the protein A column or is associated with little degradation of the column. In some embodiments, the highly stringent regeneration buffer comprises a soluble base. In some embodiments, the base is sodium hydroxide (NaOH). In some embodiments, the regeneration buffer has an NaOH concentration of greater than 0.3 M NaOH. For example, the high stringent regeneration buffer may be greater than 0.35 M, 0.4 M, 0.5 M, 0.6 M, 0.7 M, 0.8 M, 0.9 M, 1.0 M or more NaOH. In particular embodiments, the concentration of NaOH in the regeneration buffer is 0.5 M NaOH.

In some embodiments, elution of GL-2045 from a protein A affinity column is optimized to remove or reduce the amount of high molecular weight, unordered aggregates of GL-2045 from the drug substance. In some embodiments, GL-2045 is eluted from a protein A column by an elution gradient (e.g., a pH elution gradient).

In some embodiments, optimized downstream manufacturing methods for GL-2045 comprise a multiple step purification process comprising purification by affinity chromatography (e.g., protein A affinity chromatography) and at least one or more polishing steps selected from cation exchange chromatography, anion exchange chromatography, and hydrophobic interaction columns. In a preferred embodiment, a four step purification process for GL-2045 is used instead of the two or three step purification process commonly practiced in the art, comprising purification by affinity chromatography (e.g., protein A affinity chromatography) polishing by each of cation exchange chromatography, anion exchange chromatography, and hydrophobic interaction columns. The term "polishing" classically refers to post-protein A purification removal of remaining impurities including aggregates, endotoxin, DNA, and/or viruses. Additionally, with respect to GL-2045, "polishing" additionally means controlling the percent of homodimer and specific higher order multimers such as through the use of these same chromatographic techniques.

In some embodiments, GL-2045 is polished by ion exchange chromatography (e.g., cation or anion exchange). In some embodiments, polishing of GL-2045 by ion exchange chromatography is performed with an elution buffer that reduces and/or minimizes the amount of unordered, high molecular weight aggregates of the GL-2045 homodimer that are retained during the post-protein A purification process. In some embodiments, step elution is performed to elute GL-2045 from the protein A column. In some embodiments, a gradient elution is performed to elute GL-2045 from the protein A column. In some embodiments, the elution buffer is a sodium acetate buffer. In some embodiments, the concentration of sodium acetate in the elution buffer is at least 25 mM. For example, the concentration of sodium acetate in the elution buffer may be at least 30, 35, 40, 45, 50, 55, 60, 75, 100 mM, or more of sodium acetate. In some embodiments, the elution buffer is 50 mM sodium acetate. In some embodiments, the elution buffer is 50 mM sodium acetate with the addition of varying amounts of an additional salt buffer (e.g., an NaCl buffer). In some embodiments, the additional buffer is a 1 M NaCl, pH 5 buffer ("buffer b"). In some embodiments, the elution buffer comprises at least 30% buffer B. In some embodiments, the elution buffer comprises between 30% and 40% buffer B. In some embodiments, the elution buffer comprises between 35% and 40% buffer B. In still further embodiments, the elution buffer comprises between 37% and 39% buffer B. In some embodiments, the elution buffer is 38%+/−0.5% buffer b.

In some embodiments, GL-2045 is polished using hydrophobic interaction chromatography (HIC). In some embodiments, the HIC column is selected to remove the high molecular weight, unordered aggregates of GL-2045 (e.g., an Octyl FF HIC column). Either flow through mode or binding mode may be performed to purify GL-2045 with the HIC column. The skilled artisan understands that adjusting variables such as pH and salt conditions will determine whether GL-2045 binds to the HIC resin or flows through the column. In some embodiments, the HIC column is selected to purify a specific fraction of GL-2045, such as the homodimer and/or the higher order multimers (e.g., a Butyl HP and/or a Phenyl HP column). In some embodiments, it may be desirable to isolate a specific fraction of GL-2045 for the treatment of a particular disease indication. For example, HIC columns may be used to generate drug substances that are substantially comprised of a specific GL-2045 fraction (e.g., a drug substance that is predominantly comprised of GL-2045 homodimers, a drug substance that is predominantly comprised of dimers of the homodimers, a drug substance that is predominantly comprised of higher-ordered multimer of GL-2045, etc.). Separation of GL-2045 fractions into separate products may be advantageous for certain disease indications. For example, the GL-2045 homodimer binds to FcγRI, but does substantially bind to other FcRs. As such, the GL-2045 homodimer may be especially useful in the treatment of diseases mediated, at least in part, by FcγRI signaling, such as peritonitis (Heller et al., J. Immunol, V. 162, 1992) or acute lung injury (Xie et al. J. Immunol., V 188, 2012). Similarly, the trimer of GL-2045, and potentially the dimer and tetramer, may be particularly useful for treating autoimmune diseases (See, WO 2015/168643). As C1q is hexameric, the pentamer, hexamer, and heptamers may be especially useful in the treatment of complement-mediated diseases. A skilled artisan will recognize that these are only some of the ways that GL-2045 fractions may be advantageous for treating certain diseases.

In some embodiments, the optimized downstream manufacturing methods described herein may be a combination of individual purification and/or filtration techniques. For example, in some embodiments, the optimized downstream methods may comprise purification of GL-2045 by affinity chromatography (e.g., purification by optimized methods for protein A columns) followed by additional polishing with ion exchange chromatography methods (e.g. polishing by optimized cation exchange methods) and/or hydrophobic interaction columns. In some embodiments, the optimized downstream methods described herein comprise a four-step purification process including purification by protein A, cation exchange, anion exchange flow through, and hydrophobic interaction columns. In some embodiments, additional depth filtration and/or ultrafiltration steps may also be used.

Figure 33:
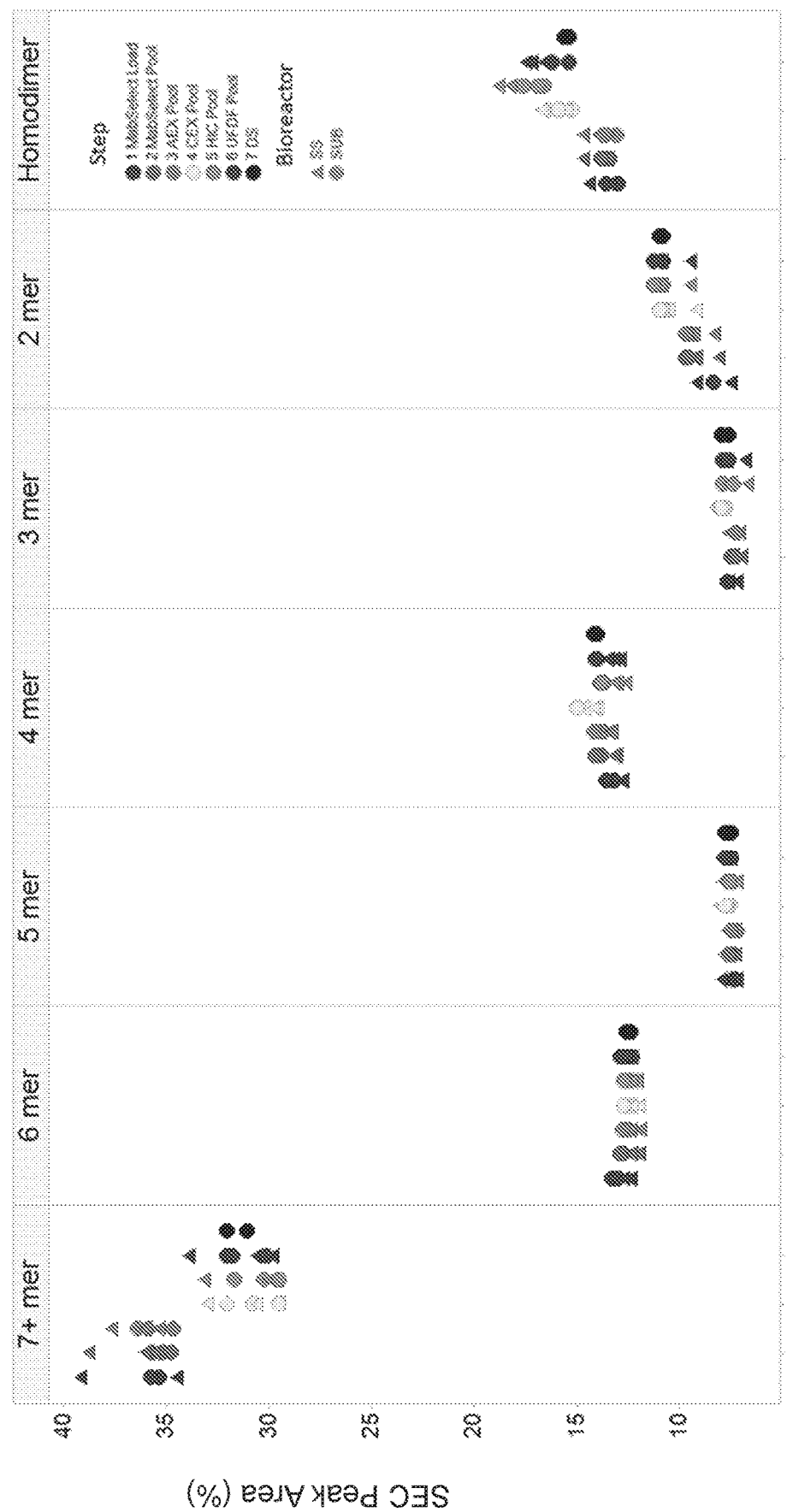
FIG. 33 illustrates a defined multimer pattern of an optimally manufactured GL-2045 composition.

Thus, the terms "optimal manufacturing methods" or "optimized manufacturing methods" used interchangeably herein, may refer to optimized upstream and/or optimized downstream manufacturing methods. In some embodiments, the optimized manufacturing methods comprise both optimized upstream and downstream methods. As such, the terms "optimally manufactured stradomer" or "optimally manufactured GL-2045," as used herein, refer to high titer, high-order multimer dominant GL-2045 compositions made in accordance with optimized upstream manufacturing conditions and/or optimized downstream manufacturing methods. While the GL-2045 composition described herein may be optimally produced GL-2045 (i.e., GL-2045 made by the methods described herein), one of skill in the art will understand that GL-2045 compositions that fall within the defined multimer patterns described herein may be achieved by other means. Therefore, a "GL-2045 composition" or "recombinant GL-2045 composition" or "purified GL-2045 composition" refers to a composition comprising GL-2045, including a GL-2045 drug substance, whether the composition was made via optimal manufacturing methods or not. Herein, the terms "multimer pattern" or "banding pattern" or any like term are used interchangeably and refer to the pattern of multimers observed in an analytical assay of a GL-2045 composition. An exemplary multimer pattern is shown in FIG. 33.

In some embodiments, a recombinantly produced GL-2045 composition with a defined multimer pattern is provided herein. As used herein, the terms "defined multimer pattern" or "defined multimerization pattern" or "defined banding pattern" refer to a pattern of GL-2045 multimerization that is reproducible and can be described in terms of the percentage of the total GL-2045 composition present as homodimers, higher order multimers, and/or highest order multimers. One of ordinary skill in the art will understand that the absolute value of the homodimer and/or multimer percentages may vary based on the analytical method used. By way of example, digital software analysis of an SDS-PAGE gel will yield somewhat different multimer percentages compared with analytical SEC-HPLC of the identical composition. Unless otherwise specified herein, the percentages of homodimers and multimers of the GL-2045 compositions described herein are expressed as percentages measured by analytical SEC-HPLC methods. In some embodiments, a recombinantly produced GL-2045 is provided in which at least 80% of GL-2045 is present as non-homodimers or "multimers" (e.g., dimers of homodimers, trimers of homodimers, etc.). In some embodiments, greater than 80% of GL-2045 is present as multimers. For example, optimized manufacturing methods, such as those described herein may result in a GL-2045 protein composition wherein 80%, 85%, 90%, 95%, or greater of the GL-2045 is present as multimers. In some embodiments, at least 30% of GL-2045 is present as "highest order multimers," defined herein as the 7-mer of the homodimer and above. In some embodiments, no more than 40% of the recombinantly produced GL-2045 is present as highest ordered multimers. One of ordinary skill in the art will also understand that when we talk about "bands," or "fractions" unless specified otherwise, the number of the band connotes the number of homodimers present in the fraction. Thus, for example, band 2 comprises the dimer of the homodimer while band 3 comprises the trimer of the homodimer. Thus, for example, band 2 comprises the dimer of the homodimer, band 3 comprises the trimer of the homodimer, band 4 comprises the tetramer of the homodimer, etc.

As used herein, the term "higher order multimers" refers to the trimers of the homodimer and above (i.e., multimers present in fraction 3 and above). As used herein, the term "highest order multimers" refers to the multimers in fraction 7 and above, or fractions including the 7-mer of the homodimer and above.

In some embodiments, a recombinantly produced GL-2045 composition is provided wherein the homodimeric fraction comprises less than about 20% of the total composition. In some embodiments, the homodimeric fraction comprises about 12% to about 19%, about 14% to about 19%, about 15.5% to about 17.5%, or about 14% to about 18.5% of the total protein composition. In some embodiments, the homodimeric fraction comprises about 15.9% or about 16.2% of the total protein composition.

In some embodiments, a recombinantly produced GL-2045 composition is provided wherein the dimer of the homodimer fraction comprises about 7% to about 13%, about 7% to about 12.5%, about 7% to about 12%, about 90% to about 11%, or about 9.1% to about 11.7% of the total composition. In some embodiments, the dimer of the homodimer fraction comprises about 10% or about 10.6% of the total protein composition.

In some embodiments, a recombinantly produced GL-2045 composition is provided wherein the trimer of the homodimer fraction comprises about 5.5% to about 11%, about 5.5% to about 10%, or about 6.5% to about 8% of the total composition. In some embodiments, the trimer of the homodimer fraction comprises about 7% or about 7.3% of the total protein composition.

In some embodiments, a recombinantly produced GL-2045 composition is provided wherein the tetramer of the homodimer fraction comprises about 10% to about 16%, about 11% to about 16%, about 13% to about 15%, or about 12.4% to about 15.1% of the total composition. In some embodiments, the tetramer of the homodimer fraction comprises about 14% or about 14.3% of the total protein composition.

In some embodiments, a recombinantly produced GL-2045 composition is provided wherein the pentamer of the homodimer fraction comprises about 6% to about 9%, about 7% to about 8%, or about 7.1% to about 8.2% of the total composition. In some embodiments, the dimer of the pentamer fraction comprises about 7% or about 7.5% of the total protein composition.

In some embodiments, a recombinantly produced GL-2045 composition is provided wherein the hexamer of the homodimer fraction comprises about 10% to about 14%, about 12% to about 13%, or about 12.1% to about 13.2% of the total composition. In some embodiments, the hexamer of the homodimer fraction comprises about 12.7% or about 12.6% of the total protein composition.

In some embodiments, a recombinantly produced GL-2045 composition is provided wherein the highest order multimer fraction comprises at least about 28% of the total composition. In some embodiments, the highest order multimer fraction comprises no more than about 35% of the total protein composition. In some embodiments, the highest order multimer fraction comprises about 30% to about 34%, or about 28.6% to about 35.1% of the total protein composition. In some embodiments, the highest order multimer fraction comprises about 31.4% or about 31.9% of the total protein composition. In some embodiments, a recombinantly produced GL-2045 composition is provided wherein the homodimeric fraction comprises less than about 20% of the total composition; the highest order multimer fractions comprise at least about 28% of the total composition; the dimer of the homodimer fraction comprises from about 7% to about 13% of the total composition; the trimer of the homodimer fraction comprises from about 5% to about 11% of the total composition; the tetramer of the homodimer fraction comprises from about 10%/o to about 16% of the total composition; the pentamer of the homodimer fraction comprises from about 6% to about 10% of the total composition; the hexamer of the homodimer fraction comprises from about 10% to about 14% of the total fraction; the dimer of the homodimer through hexamer of the homodimer fraction comprises from about 40% to about 60% of the total composition; the trimer of the homodimer through the hexamer of the homodimer fractions comprise from about 32% to about 50% of the total composition; the tetramer of the homodimer through the hexamer of the homodimer fraction comprise from about 30% to about 37% of the total composition; the pentamer of the homodimer through the hexamer of the homodimer fraction comprise from about 18% to about 23% of the total composition; or any combination of the forgoing.

In some embodiments, a recombinantly produced GL-2045 composition is provided, wherein the approximately 80% of the total GL-2045 composition comprises the dimer of the homodimer and above (i.e., band 2 and above). In some embodiments, approximately 60-80%, 62-80%, or 60-78% of the total recombinantly-produced GL-2045 composition comprises the trimer of the homodimer and above (i.e., bands 3 and above). In some embodiments, about 54-76%, about 54-72%, about 56-76%, or about 54-67% the total recombinantly produced GL-2045 composition comprises the tetramer and above (i.e., bands 4 and above). In some embodiments, a GL-2045 composition is provided, wherein approximately 44-60%, 44-57%, or 44-51% of the total composition comprises the pentamer and above (i.e., bands 5 and above). In some embodiments, a GL-2045 composition is provided, wherein approximately 38-51% of the total composition comprises the hexamer and above (i.e., bands 6 and above).

In some embodiments, a recombinantly produced GL-2045 is provided wherein bands 2-6 of the composition (i.e., the dimer of the homodimer through the hexamer of the homodimer) comprise about 39-61% or about 44-60% of the composition. In some embodiments, a recombinantly produced GL-2045 is provided, wherein bands 3-6 of the composition (i.e., the trimer of the homodimer through the hexamer of the homodimer) comprises about 32-50% or about 35-48% of the composition. In some embodiments, a recombinantly produced GL-2045 is provided wherein bands 4-6 of the composition (i.e., the tetramer of the homodimer through the hexamer of the homodimer) comprises about 26-39% or about 30-39% of the composition. In some embodiments, a recombinantly produced GL-2045 is provided wherein the bands 5-6 of the composition (i.e., the pentamer of the homodimer through the hexamer of the homodimer) comprises about 16-23% or about 18-23% of the composition.

Without being bound by theory, the least active components of GL-2045 in binding to low affinity Fc receptors and to C1q are the homodimer and the dimer of the homodimer. A skilled artisan will readily appreciate that one can use the optimized chromatographic methods described herein, or similar purification techniques, to reduce the amount of homodimer or homodimer and dimer in the final product. The skilled artisan will thus know that doing so will alter the percentages of the multimers disclosed herein. By way of example and without limiting the generality of the foregoing, if the skilled artisan were to remove 50% of the homodimer in the purification process, or homodimer and the dimer, then the percentage of each remaining multimer (i.e., trimers, tetramers, pentamers, hexamers, 7-mers, etc.) would correspondingly increase. Removing 90% of the homodimer and 50% of the dimer will decrease the total protein present in the final product by approximately 20%+/−5%, and will therefore increase the percentages of the trimer, tetramer, pentamer, hexamer, and 7-mer represented as a percent of the total protein.

What is more, one of skilled in the art will further recognize that current chromatography techniques do not generally permit removal or reduction of a single multimer band, such as the highest order multimers, without simultaneously removing, to some degree, the adjacent bands, such as the hexamer and to a lesser extent the pentamer. Therefore, the skilled artisan will know that the observed compensatory increase in the percentage of any given multimer or homodimer as a result of removal or reduction of the highest order multimers will increase by a greater degree the farther the given multimer is from the fraction of GL-2045 that is removed (e.g., the percentage of the homodimer will increase by a greater degree than the increased percentage observed for the hexamers when the highest order multimers are removed or reduced). In any case, the cumulative increase in multimer percentages of the remaining multimers should equal the multimer percent for the removed fractions, subject to some variability attributable to analytical method.

Pharmaceutical Compositions

Administration of the GL-2045 compositions described herein will be via any common route, orally, parenterally, or topically. Exemplary routes include, but are not limited to oral, nasal, buccal, rectal, vaginal, ophthalmic, subcutaneous, intramuscular, intraperitoneal, intravenous, intraarterial, intratumoral, spinal, intrathecal, intra-articular, intra-arterial, sub-arachnoid, sublingual, oral mucosal, bronchial, lymphatic, intrauterine, subcutaneous, intratumor, integrated on an implantable device such as a suture or in an implantable device such as an implantable polymer, intradural, intracortical, or dermal. Such compositions would normally be administered as pharmaceutically acceptable compositions as described herein. In a preferred embodiment, the isolated optimally manufactured stradomer is administered intravenously or subcutaneously.

The term "pharmaceutically acceptable carrier" as used herein includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions The GL-2045 compositions of the present invention may be formulated in a neutral or salt form. Pharmaceutically-acceptable salts include the acid addition salts (formed with the free amino groups of the protein) which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like.

Sterile injectable solutions are prepared by incorporating the optimally manufactured GL-2045 in the required amount in the appropriate solvent with various of the other ingredients enumerated above, as required, followed by filtered sterilization. In some embodiments, the sterile injectable solutions are formulated for intramuscular, subcutaneous, or intravenous administration. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Further, one embodiment is a GL-2045 composition suitable for oral administration and is provided in a pharmaceutically acceptable carrier with or without an inert diluent. The carrier should be assimilable or edible and includes liquid, semi-solid (e.g., pastes), or solid carriers. Except insofar as any conventional media, agent, diluent or carrier is detrimental to the recipient or to the therapeutic effectiveness of an optimally manufactured stradomer preparation contained therein, its use in an orally administrable optimally manufactured stradomer composition for use in practicing the methods of the present invention is appropriate. Examples of carriers or diluents include fats, oils, water, saline solutions, lipids, liposomes, resins, binders, fillers and the like, or combinations thereof. The term "oral administration" as used herein includes oral, buccal, enteral or intragastric administration.

In one embodiment, the GL-2045 composition is combined with the carrier in any convenient and practical manner, i.e., by solution, suspension, emulsification, admixture, encapsulation, microencapsulation, absorption and the like. Such procedures are routine for those skilled in the art.

In a specific embodiment, the GL-2045 composition in powder form is combined or mixed thoroughly with a semi-solid or solid carrier. The mixing can be carried out in any convenient manner such as grinding. Stabilizing agents can be also added in the mixing process in order to protect the composition from loss of therapeutic activity (e.g., through denaturation in the stomach). Examples of stabilizers for use in an orally administrable composition include buffers, antagonists to the secretion of stomach acids, amino acids such as glycine and lysine, carbohydrates such as dextrose, mannose, galactose, fructose, lactose, sucrose, maltose, sorbitol, mannitol, etc., proteolytic enzyme inhibitors, and the like. More preferably, for an orally administered composition, the stabilizer can also include antagonists to the secretion of stomach acids.

Further, the GL-2045 composition for oral administration which is combined with a semi-solid or solid carrier can be further formulated into hard or soft shell gelatin capsules, tablets, or pills. More preferably, gelatin capsules, tablets, or pills are enterically coated. Enteric coatings prevent denaturation of the composition in the stomach or upper bowel where the pH is acidic. See, U.S. Pat. No. 5,629,001. Upon reaching the small intestines, the basic pH therein dissolves the coating and permits the composition to be released to interact with intestinal cells, e.g., Peyer's patch M cells.

In another embodiment, the GL-2045 composition in powder form is combined or mixed thoroughly with materials that create a nanoparticle encapsulating the immunologically active biomimetic or to which the immunologically active biomimetic is attached. Each nanoparticle will have a size of less than or equal to 100 microns. The nanoparticle may have mucoadhesive properties that allow for gastrointestinal absorption of an immunologically active biomimetic that would otherwise not be orally bioavailable.

In another embodiment, a powdered composition is combined with a liquid carrier such as water or a saline solution, with or without a stabilizing agent.

A specific GL-2045 formulation that may be used is a solution of immunologically active biomimetic protein in a hypotonic phosphate based buffer that is free of potassium where the composition of the buffer is as follows: 6 mM sodium phosphate monobasic monohydrate, 9 mM sodium phosphate dibasic heptahydrate, 50 mM sodium chloride, pH 7.0+/−0.1. The concentration of immunologically active biomimetic protein in a hypotonic buffer may range from 10 μg/mL to 100 mg/mL. This formulation may be administered via any route of administration, for example, but not limited to intravenous administration.

Further, a GL-2045 composition for topical administration which is combined with a semi-solid carrier can be further formulated into a cream or gel ointment. A preferred carrier for the formation of a gel ointment is a gel polymer. Preferred polymers that are used to manufacture a gel composition of the present invention include, but are not limited to carbopol, carboxymethyl-cellulose, and pluronic polymers. Specifically, a powdered Fc multimer composition is combined with an aqueous gel containing a polymerization agent such as Carbopol 980 at strengths between 0.5% and 5% wt/volume for application to the skin for treatment of disease on or beneath the skin. The term "topical administration" as used herein includes application to a dermal, epidermal, subcutaneous, or mucosal surface.

Further, a GL-2045 composition can be formulated into a polymer for subcutaneous or subdermal implantation. A preferred formulation for the implantable drug-infused polymer is an agent Generally Regarded as Safe and may include, for example, cross-linked dextran (Samantha Hart, Master of Science Thesis, "Elution of Antibiotics from a Novel Cross-Linked Dextran Gel: Quantification" Virginia Polytechnic Institute and State University, Jun. 8, 2009) dextran-tyramine (Jin, et al. (2010) Tissue Eng. Part A. 16(8):2429-40), dextran-polyethylene glycol (Jukes, et al. (2010) Tissue Eng. Part A., 16(2):565-73), or dextran-gluteraldehyde (Brondsted, et al. (1998) J. Controlled Release, 53:7-13). One skilled in the art will know that many similar polymers and hydrogels can be formed incorporating the stradomer fixed within the polymer or hydrogel and controlling the pore size to the desired diameter.

Upon formulation, solutions are administered in a manner compatible with the dosage formulation and in such amount as is therapeutically effective to result in an improvement or remediation of the symptoms. The formulations are easily administered in a variety of dosage forms such as ingestible solutions, drug release capsules and the like. Some variation in dosage can occur depending on the condition of the subject being treated. The person responsible for administration can, in any event, determine the appropriate dose for the individual subject. Moreover, for human administration, preparations meet sterility, general safety and purity standards as required by FDA Center for Biologics Evaluation and Research standards.

The route of administration will vary, naturally, with the location and nature of the disease being treated, and may include, for example intradermal, transdermal, subdermal, parenteral, nasal, intravenous, intramuscular, intranasal, subcutaneous, percutaneous, intratracheal, intraperitoneal, intratumoral, perfusion, lavage, direct injection, intra-rectal, and oral administration.

In one embodiment, the GL-2045 composition intravenously, subcutaneously, orally, intraperitoneally, sublingually, buccally, transdermally, rectally, by subdermal implant, or intramuscularly. In particular embodiments, the optimally manufactured stradomer is administered intravenously, subcutaneously, or intramuscularly. In one embodiment, the optimally manufactured stradomer is administered at a dose of about 0.005 mg/Kg to about 1000 mg/Kg. In a further embodiment, the optimally manufactured stradomer is administered at about 0.01 mg/Kg to about 100 mg/Kg. In yet a further embodiment, the optimally manufactured stradomer is administered at about 0.1 mg/Kg to about 20 mg/Kg. In still a further embodiment, the optimally manufactured stradomer is administered at about 1 mg/Kg to about 10 mg/Kg. In still a further embodiment, the optimally manufactured stradomer is administered at about 2 mg/Kg to about 5 mg/Kg. The optimally manufactured stradomer may be administered at least once daily, weekly, biweekly, monthly, or sometimes longer intervals. A biphasic dosage regimen may be used wherein the first dosage phase comprises about 0.1% to about 300% of the second dosage phase.

In a further embodiment, the GL-2045 composition is administered before, during or after administration of one or more additional pharmaceutical and/or therapeutic agents. In a further embodiment the additional pharmaceutically active agent comprises a steroid; a biologic anti-autoimmune drug such as a monoclonal antibody, a fusion protein, or an anti-cytokine; a non-biologic anti-autoimmune drug; an immunosuppressant; an antibiotic; and anti-viral agent; a cytokine; or an agent otherwise capable of acting as an immune-modulator. In still a further embodiment, the steroid is prednisone, prednisolone, cortisone, dexamethasone, mometasone testosterone, estrogen, oxandrolone, fluticasone, budesonide, beclamethasone, albuterol, or levalbuterol. In still a further embodiment, the monoclonal antibody is eculizumab, ocrelizumab, infliximab, adalimumab, rituximab, tocilizumab, golimumab, ofatumumab, LY2127399, belimumab, veltuzumab, mepolizumab, necitumumab, nivolumab, dinutuximab, secukinumab, evolocumab, blinatumomab, pembrolizumab, ramucirumab, vedolizumab, siltuximab, obinutuzumab, adotrastuzumab, raxibacumab, pertuzumab, brentuximab, ipilumumab, denosumab, canakinumab, ustekinumab, catumaxomab, ranibizumab, panitumumab, natalizumab, bevacizumab, cetuximab, efalizumab, omalizumab, toitumomab-I131, alemtuzumab, gemtuzumab, trastuzumab, palivizumab, basiliximab, daclizumab, abciximab, murononomab, vedotin, ibritumomab tiuxetan, motavizumab, or certolizumab. In still a further embodiment, the fusion protein is etanercept or abatacept. In still a further embodiment, the anti-cytokine biologic is anakinra. In still a further embodiment, the anti-rheumatic non-biologic drug is cyclophosphamide, methotrexate, azathioprine, hydroxychloroquine, leflunomide, minocycline, organic gold compounds, fostamatinib, tofacitinib, etoricoxib, or sulfasalazine. In still a further embodiment, the immunosuppressant is cyclosporine A, tacrolimus, sirolimus, mycophenolate mofetil, everolimus, OKT3, antithymocyte globulin, basiliximab, daclizumumab, or alemtuzumab. In still a further embodiment, the optimally manufactured stradomer is administered before, during or after administration of a chemotherapeutic agent. In still a further embodiment, the optimally manufactured stradomer and the additional therapeutic agent display therapeutic synergy when administered together. In one embodiment, the optimally manufactured stradomer is administered prior to the administration of the additional therapeutic against. In another embodiment, the optimally manufactured stradomer is administered at the same time as the administration of the additional therapeutic agent. In still another embodiment, the optimally manufactured stradomer is administered after the administration with the additional therapeutic agent.

In one embodiment, the GL-2045 composition is administered covalently fixed to an implantable device. In one embodiment, the optimally manufactured stradomer is fixed to a suture. In another embodiment, the optimally manufactured stradomer is fixed to a graft or stent. In another embodiment, the optimally manufactured stradomer is fixed to a heart valve, an orthopedic joint replacement, or implanted electronic lead. In another embodiment, the optimally manufactured stradomer is fixed to and embedded within an implantable matrix. In a preferred embodiment, the optimally manufactured stradomer is fixed to and embedded within an implantable hydrogel. In one embodiment, the hydrogel is comprised of dextran, polyvinyl alcohol, sodium polyacrylate, or acrylate polymers. In a further embodiment, the optimally manufactured stradomer is administered fixed in a hydrogel with pore sizes large enough to allow entry of immune cells to interact with the fixed stradomer and then return to circulation. In a further embodiment, the pore size of the hydrogel is 5 to 50 microns. In a preferred embodiment, the pore size of the hydrogel is 25-30 microns.

In another embodiment, the GL-2045 composition is administered to treat humans, non-human primates (e.g., monkeys, baboons, and chimpanzees), mice, rats, bovines, horses, cats, dogs, pigs, rabbits, goats, deer, sheep, ferrets, gerbils, guinea pigs, hamsters, bats, birds (e.g., chickens, turkeys, and ducks), fish and reptiles with species-specific or chimeric stradomer molecules. In another embodiment, the human is an adult or a child. In still another embodiment, the optimally manufactured stradomer is administered to prevent a complement-mediated disease. In a further embodiment, the stradomer is administered to prevent vaccine-associated autoimmune conditions in companion animals and livestock.

The term "parenteral administration" as used herein includes any form of administration in which the compound is absorbed into the subject without involving absorption via the intestines. Exemplary parenteral administrations that are used in the present invention include, but are not limited to subcutaneous, intramuscular, intravenous, intraperitoneal, intratumoral, intraocular, nasal, or intraarticular administration.

In addition, the GL-2045 composition of the current invention may optionally be administered before, during, or after another pharmaceutical agent.

Below are specific examples of various pharmaceutical formulation categories and preferred routes of administration, as indicated, for specific exemplary diseases:

Buccal or sub-lingual dissolvable tablet: angina, polyarteritis nodosa.

Intravenous, intramuscular, or subcutaneous: myasthenia gravis, hemolytic uremic syndrome (HUS), atypical hemolytic uremic syndrome (aHUS), paroxysmal nocturnal hemoglobinuria (PNH), membranous nephropathy, neuromyelitis optica, antibody-mediated rejection of allografts, lupus nephritis, membranoproliferative glomerulonephritis (MPGN), idiopathic thrombocytopenic purpura, inclusion body myositis, paraproteinemic IgM demyelinating polyneuropathy, necrotizing fasciitis, pemphigus, gangrene, dermatomyositis, granuloma, lymphoma, sepsis, aplastic anemia, multisystem organ failure, multiple myeloma, monoclonal gammopathy of unknown significance, chronic inflammatory demyelinating polyradiculoneuropathy, inflammatory myopathies, thrombotic thrombocytopenic purpura, myositis, anemia, neoplasia, hemolytic anemia, encephalitis, myelitis, myelopathy especially associated with human T-cell lymphotropic virus-1, leukemia, multiple sclerosis and optic neuritis, asthma, epidermal necrolysis, Lambert-Eaton myasthenic syndrome, neuropathy, uveitis, Guillain-Barré syndrome, graft versus host disease, stiff man syndrome, paraneoplastic cerebellar degeneration with anti-Yo antibodies, paraneoplastic encephalomyelitis and sensory neuropathy with anti-Hu antibodies, systemic vasculitis, systemic lupus erythematosus, autoimmune diabetic neuropathy, acute idiopathic dysautonomic neuropathy, Vogt-Koyanagi-Harada Syndrome, multifocal motor neuropathy, lower motor neuron syndrome associated with anti-/GM1, demyelination, membranoproliferative glomerulonephritis, cardiomyopathy, Kawasaki's disease, rheumatoid arthritis, and Evan's syndrome, CIDP, MS, dermatomyositis, muscular dystrophy. The term "intravenous administration" as used herein includes all techniques to deliver a compound or composition of the present invention to the systemic circulation via an intravenous injection or infusion.

Dermal gel, lotion, cream or patch: vitiligo, Herpes zoster, acne, chelitis.

Rectal suppository, gel, or infusion: ulcerative colitis, hemorrhoidal inflammation.

Oral as pill, troche, encapsulated, or with enteric coating: Crohn's disease, celiac sprue, irritable bowel syndrome, inflammatory liver disease, Barrett's esophagus.

Intra-cortical: epilepsy, Alzheimer's, multiple sclerosis, Parkinson's Disease, Huntington's Disease.

Intra-abdominal infusion or implant: endometriosis.

Medical devices: coated on coronary artery stent, prosthetic joints.

Therapeutic Applications of Optimally Manufactured GL-2045

In one embodiment, a method for treating or preventing a disease or condition such as an autoimmune disease, inflammatory disease, or complement-mediated disease or condition is provided.

Based on rational design and in vitro and in vivo validations, the optimally manufactured GL-2045 of the present invention will serve as an important biopharmaceuticals for treating inflammatory diseases and disorders, as well as for altering immune function in a variety of other contexts such as bioimmunotherapy for allergies, cancer, autoimmune diseases, infectious diseases, and inflammatory diseases. Medical conditions suitable for treatment with the immunologically active optimally manufactured GL-2045 disclosed herein include any disease caused by or associated with complement activation or complement-mediated effector functions, including increased or inappropriate complement activity. Such medical conditions include those that are currently or have previously been treated with complement binding drugs such as eculizumab. Eculizumab binds to complement protein C5 (a complement protein that is downstream of C1 and C1q in the classical complement pathway), inhibiting its cleavage and subsequent complement-mediated cell lysis. The biomimetics of the present invention provide a safe and effective alternative to other complement-binding drugs known in the art. For example, in some embodiments, the biomimetics of the present invention bind C1q, the first subunit in the C1 complex of the classical complement pathway. Medical conditions suitable for treatment with the immunologically active optimally manufactured stradomers include, but are not limited to, myasthenia gravis, hemolytic uremic syndrome (HUS), atypical hemolytic uremic syndrome (aHUS), paroxysmal nocturnal hemoglobinuria (PNH), membranous nephropathy, neuromyelitis optica, antibody-mediated rejection of allografts, lupus nephritis, macular degeneration, sickle cell disease, and membranoproliferative glomerulonephritis (MPGN). Additional medical conditions suitable for treatment with the immunologically active optimally manufactured GL-2045 described herein include those currently routinely treated with broadly immune suppressive therapies including hIVIG, or in which hIVIG has been found to be clinically useful such as autoimmune cytopenias, chronic inflammatory demyelinating polyneuropathy, Guillain-Barre' syndrome, myasthenia gravis, anti-Factor VIII autoimmune disease, dermatomyositis, vasculitis, and uveitis (See, F. G. van der Meche et al., N. Engl. J. Med. 326, 1123 (1992); P. Gajdos et al, Lancet i, 406 (1984); Y. Sultan, M. et al, Lancet ii, 765 (1984); M. C. Dalakas et al., N. Engl. J. Med. 329, 1993 (1993); D. R. Jayne et al., Lancet 337, 1137 (1991); P. LeHoang, et al., Ocul. Immunol. Inflamm. 8, 49 (2000)) and those cancers or inflammatory disease conditions in which a monoclonal antibody may be used or is already in clinical use. Conditions included among those that may be effectively treated by the compounds that are the subject of this invention include an inflammatory disease with an imbalance in cytokine networks, an autoimmune disorder mediated by pathogenic autoantibodies or autoaggressive T cells, or an acute or chronic phase of a chronic relapsing autoimmune, inflammatory, or infectious disease or process.

In addition, other medical conditions having an inflammatory component involving complement will benefit from treatment with the GL-2045 composition such as asthma, lupus erythematosus, glomerulonephritis, glomerular nephropathy, arthritis, autoantibody-mediated diseases including autoimmune hemolytic anemia and autoimmune heart disease, multiple sclerosis, Amyotrophic Lateral Sclerosis, Huntington's Disease, Alzheimer's Disease, Parkinson's Disease, Inflammatory Bowel Disease, paroxysman nocturnal hemoglobinuria, atypical hemolytic uremic syndrome, ischemia-reperfusion injuries including as examples myocardial infarction, spinal cord injury, and stroke, rejection of transplanted organs or blood, Hepatitis B, Hepatitis C, Human Immunodeficiency Virus associated inflammation, adrenoleukodystrophy, and epileptic disorders especially those believed to be associated with postviral encephalitis including Rasmussen Syndrome, West Syndrome, and Lennox-Gastaut Syndrome.

The general approach to therapy using the GL-2045 composition described herein is to administer to a subject having a disease or condition, a therapeutically effective amount of the GL-2045 composition to effect a treatment. In some embodiments, diseases or conditions may be broadly categorized as inflammatory diseases with an imbalance in cytokine networks, an autoimmune disorder mediated by pathogenic autoantibodies or autoaggressive T cells, or an acute or chronic phase of a chronic relapsing disease or process.

The term "treating" and "treatment" as used herein refers to administering to a subject a therapeutically effective amount of an optimally manufactured stradomer of the present invention so that the subject has an improvement in a disease or condition, or a symptom of the disease or condition. The improvement is any improvement or remediation of the disease or condition, or symptom of the disease or condition. The improvement is an observable or measurable improvement, or may be an improvement in the general feeling of well-being of the subject. Thus, one of skill in the art realizes that a treatment may improve the disease condition, but may not be a complete cure for the disease. Specifically, improvements in subjects may include one or more of: decreased inflammation; decreased inflammatory laboratory markers such as C-reactive protein; decreased autoimmunity as evidenced by one or more of improvements in autoimmune markers such as autoantibodies or in platelet count, white cell count, or red cell count, decreased rash or purpura, decrease in weakness, numbness, or tingling, increased glucose levels in patients with hyperglycemia, decreased joint pain, inflammation, swelling, or degradation, decrease in cramping and diarrhea frequency and volume, decreased angina, decreased tissue inflammation, or decrease in seizure frequency; decreases in cancer tumor burden, increased time to tumor progression, decreased cancer pain, increased survival or improvements in the quality of life; or delay of progression or improvement of osteoporosis.

The term "therapeutically effective amount" as used herein refers to an amount that results in an improvement or remediation of the symptoms of the disease or condition. One of ordinary skill in the art will understand that the therapeutically effective amount of the GL-2045 produced herein can vary depending on the final drug substance. Thus, for example, if one were to eliminate all lower order multimers, it is conceivable that a reduced dose of the resulting higher order multimers may be required. As such, there is more than one "therapeutically effective dose" of GL-2045.

As used herein, "prophylaxis" can mean complete prevention of the symptoms of a disease, a delay in onset of the symptoms of a disease, or a lessening in the severity of subsequently developed disease symptoms.

The term "subject" as used herein, is taken to mean any mammalian subject to which optimally manufactured stradomers of the present invention are administered according to the methods described herein. In a specific embodiment, the methods of the present disclosure are employed to treat a human subject. The methods of the present disclosure may also be employed to treat non-human primates (e.g., monkeys, baboons, and chimpanzees), mice, rats, bovines, horses, cats, dogs, pigs, rabbits, goats, deer, sheep, ferrets, gerbils, guinea pigs, hamsters, bats, birds (e.g., chickens, turkeys, and ducks), fish, and reptiles to produce species-specific or chimeric stradomer molecules.

Complement inhibition has been demonstrated to decrease antibody-mediated diseases (See for example Stegall et al., American Journal of Transplantation 2011 November; 11(1):2405-2413-Epub 2011 Sep. 22). The optimally manufactured stradomers of the present invention may also be used to treat a disease or condition that is antibody-mediated. Auto-antibodies mediate many known autoimmune diseases and likely play a role in numerous other autoimmune diseases. Recognized antibody mediated diseases in which the optimally manufactured stradomers of the present invention may be used include, but are not limited to, anti-glomerular basement membrane antibody mediated nephritis including Goodpasture's; anti-donor antibodies (donors-specific alloantibodies) in solid organ transplantation; anti-Aquaporin-4 antibody in neuromyelitis optica; anti-VGKC antibody in neuromyotonia, limbic encephalitis, and Morvan's syndrome; anti-nicotinic acetylcholine receptor and anti-MuSK antibodies in myasthenia gravis; anti-VGCC antibodies in Lambert Eaton myasthenic syndrome; anti-AMPAR and anti-GABA(B)R antibodies in limbic encephalitis often associated with tumors; anti-GlyR antibodies in stiff person syndrome or hyperekplexia; anti-phospholipid, anti-cardiolipin, and anti-$\beta_2$ glycoprotein I antibodies in recurrent spontaneous abortion, Hughes syndrome, and systemic lupus erythematosus; anti-glutamic acid decarboxylase antibodies in stiff person syndrome, autoimmune cerebellar ataxia or limbic encephalitis; anti-NMDA receptor antibodies in a newly-described syndrome including both limbic and subcortical features with prominent movement disorders often in young adults and children that is often associated with ovarian teratoma but can be non-paraneoplastic; anti-double stranded DNA, anti-single stranded DNA, anti-RNA, anti-SM, and anti-C1q antibodies in systemic lupus erythematosus; anti-nuclear and anti-nucleolar antibodies in connective tissue diseases including scleroderma, Sjogren's syndrome, and polymyositis including anti-Ro, anti-La, anti-Scl 70, anti-Jo-1; anti-rheumatoid factor antibodies in rheumatoid arthritis; anti-hepatitis B surface antigen antibodies in polyarteritis nodosa; anti-centromere antibodies in CREST syndrome; anti-streptococcal antibodies in or as a risk for endocarditis; anti-thyroglobulin, anti-thyroid peroxidase, and anti-TSH receptor antibodies in Hashimoto's thyroiditis; anti-U1 RNP antibodies in mixed connective tissue disease and systemic lupus erythematosus; and anti-desmoglein and anti-keratinocyte antibodies in pemphigus.

The GL-2045 composition of the present invention may be used to treat conditions including but not limited to congestive heart failure (CHF), vasculitis, rosacea, acne, eczema, myocarditis and other conditions of the myocardium, systemic lupus erythematosus, diabetes, spondylopathies, synovial fibroblasts, and bone marrow stroma; bone loss; Paget's disease, osteoclastoma; multiple myeloma; breast cancer; disuse osteopenia; malnutrition, periodontal disease, Gaucher's disease, Langerhans' cell histiocytosis, spinal cord injury, acute septic arthritis, osteomalacia, Cushing's syndrome, monoostotic fibrous dysplasia, polyostotic fibrous dysplasia, periodontal reconstruction, and bone fractures; sarcoidosis; osteolytic bone cancers, lung cancer, kidney cancer and rectal cancer; bone metastasis, bone pain management, and humoral malignant hypercalcemia, ankylosing spondylitis and other spondyloarthropathies; transplantation rejection, viral infections, hematologic neoplasias and neoplastic-like conditions for example, Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplasmacytic leukemia), tumors of lymphocyte precursor cells, including B-cell acute lymphoblastic leukemia % lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histiocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia, tumors of the central nervous system, e.g., brain tumors (glioma, neuroblastoma, astrocytoma, medulloblastoma, ependymoma, and retinoblastoma), solid tumors (nasopharyngeal cancer, basal cell carcinoma, pancreatic cancer, cancer of the bile duct, Kaposi's sarcoma, testicular cancer, uterine, vaginal or cervical cancers, ovarian cancer, primary liver cancer or endometrial cancer, tumors of the vascular system (angiosarcoma and hemangiopericytoma)) or other cancer.

The GL-2045 composition of the present invention may be used to treat autoimmune diseases. The term "autoimmune disease" as used herein refers to a varied group of more than 80 diseases and conditions. In all of these diseases and conditions, the underlying problem is that the body's immune system attacks the body itself. Autoimmune diseases affect all major body systems including connective tissue, nerves, muscles, the endocrine system, skin, blood, and the respiratory and gastrointestinal systems. Autoimmune diseases include, for example, chronic inflammatory demyelinating polyneuropathy, multifocal motor neuropathy, systemic lupus erythematosus, rheumatoid arthritis, multiple sclerosis, myasthenia gravis, and type 1 diabetes.

The disease or condition treatable using the compositions and methods of the present invention may be a hematoimmunological process, including but not limited to sickle cell disease, idiopathic thrombocytopenic purpura, alloimmune/autoimmune thrombocytopenia, acquired immune thrombocytopenia, autoimmune neutropenia, autoimmune hemolytic anemia, parvovirus B19-associated red cell aplasia, acquired antifactor VIII autoimmunity, acquired von Willebrand disease, multiple myeloma and monoclonal gammopathy of unknown significance, sepsis, aplastic anemia, pure red cell aplasia, Diamond-Blackfan anemia, hemolytic disease of the newborn, Immune-mediated neutropenia, refractoriness to platelet transfusion, neonatal, post-transfusion purpura, hemolytic uremic syndrome, systemic vasculitis, thrombotic thrombocytopenic purpura, or Evan's syndrome.

The disease or condition may also be a neuroimmunological process, including, but not limited to, Guillain-Barre syndrome, chronic inflammatory demyelinating polyradiculoneuropathy, paraproteinemic IgM demyelinating polyneuropathy, Lambert-Eaton myasthenic syndrome, myasthenia gravis, multifocal motor neuropathy, lower motor neuron syndrome associated with anti-GM1, demyelination, multiple sclerosis and optic neuritis, stiff man syndrome, paraneoplastic cerebellar degeneration with anti-Yo antibodies, paraneoplastic encephalomyelitis, sensory neuropathy with anti-Hu antibodies, epilepsy, encephalitis, myelitis, myelopathy especially associated with human T-cell lymphotropic virus-1, autoimmune diabetic neuropathy, Alzheimer's disease, Parkinson's disease, Huntingdon's disease, or acute idiopathic dysautonomic neuropathy.

The disease or condition may also be inflammation or autoimmunity associated with hearing loss or vision loss. For example, the disease or condition may be autoimmune-related hearing loss such as noise-induced hearing loss or age-related hearing loss, or may be associated with implantation of devices such as hearing devices (e.g., cochlear implants). In some embodiments, the compositions provided herein may be administered to a subject prior to, concurrently with, or subsequent to the implantation of a device.

The disease or condition may also be a rheumatic disease process including, but not limited to, Kawasaki's disease, rheumatoid arthritis, Felty's syndrome, ANCA-positive vasculitis, spontaneous polymyositis, dermatomyositis, antiphospholipid syndromes, recurrent spontaneous abortions, systemic lupus erythematosus, juvenile idiopathic arthritis, Raynaud's, CREST syndrome, or uveitis.

The disease or condition may also be a dermatoimmunological disease process including, but not limited to, toxic epidermal necrolysis, gangrene, granuloma, autoimmune skin blistering diseases including pemphigus vulgaris, bullous pemphigoid, pemphigus foliaceus, vitiligo, Streptococcal toxic shock syndrome, scleroderma, systemic sclerosis including diffuse and limited cutaneous systemic sclerosis, or atopic dermatitis (especially steroid dependent).

The disease or condition may also be a musculoskeletal immunological disease process including, but not limited to, inclusion body myositis, necrotizing fasciitis, inflammatory myopathies, myositis, anti-decorin (BJ antigen) myopathy, paraneoplastic necrotic myopathy, X-linked vacuolated myopathy, penacillamine-induced polymyositis, atherosclerosis, coronary artery disease, or cardiomyopathy.

The disease or condition may also be a gastrointestinal immunological disease process including, but not limited to, pernicious anemia, autoimmune chronic active hepatitis, primary biliary cirrhosis, celiac disease, dermatitis herpetiformis, cryptogenic cirrhosis, reactive arthritis, Crohn's disease, Whipple's disease, ulcerative colitis, or sclerosing cholangitis.

The disease or condition may also be graft versus host disease, antibody-mediated rejection of the graft, post-bone marrow transplant rejection, post-infectious disease inflammation, lymphoma, leukemia, neoplasia, asthma, Type 1 Diabetes mellitus with anti-beta cell antibodies, Sjogren's syndrome, mixed connective tissue disease, Addison's disease, Vogt-Koyanagi-Harada Syndrome, membranoproliferative glomerulonephritis, Goodpasture's syndrome, Graves' disease, Hashimoto's thyroiditis, Wegener's granulomatosis, micropolyarterits, Churg-Strauss syndrome, polyarteritis nodosa, or multisystem organ failure.

"Allergy," as used herein, includes all immune reactions mediated by IgE as well as those reactions that mimic IgE-mediated reactions. Allergies are induced by allergens, including proteins, peptides, carbohydrates, and combinations thereof, that trigger an IgE or IgE-like immune response. Exemplary allergies include nut allergies, pollen allergies, and insect sting allergies. Exemplary allergens include urushiol in poison ivy and oak; house dust antigen; birch pollen components Bet v 1 and Bet v 2; the 15 kD antigen in celery; apple antigen Mal d 1; Pru p3 in peach; Timothy grass pollen allergen Phi p 1; Lol p 3, Lol p I, or Lol p V in Rye grass; Cyn d 1 in Bermuda grass; dust mite allergens dust mite Der p1, Der p2, or Der f1: α-gliadin and γ-gliadin epitopes in gluten; bee venom phospholipase A2; Ara h 1, Ara h 2, and Ara h 3 epitopes in peanuts.

In another embodiment, the GL-2045 composition described herein could be utilized in a priming system wherein blood is drawn from a patient and transiently contacted with the optimally manufactured stradomer(s) for a period of time from about one half hour to about three hours prior to being introduced back into the patient. In this form of cell therapy, the patient's own effector cells are exposed to the optimally manufactured stradomer that is fixed on a matrix ex vivo in order to modulate the effector cells through exposure of the effector cells to the optimally manufactured stradomer. The blood, including the modulated effector cells, is then infused back into the patient. Such a priming system could have numerous clinical and therapeutic applications.

The GL-2045 composition disclosed herein may also be readily applied to alter immune system responses in a variety of contexts to affect specific changes in immune response profiles. Altering or modulating an immune response in a subject refers to increasing, decreasing or changing the ratio or components of an immune response. For example, cytokine production or secretion levels may be increased or decreased as desired by targeting complement along with the appropriate combination of FcRs with a stradomer designed to bind complement and interact with those receptors. Antibody production may also be increased or decreased; the ratio of two or more cytokines or immune cell receptors may be changed; or additional types of cytokines or antibodies may be caused to be produced.

In a preferred embodiment, a subject with an autoimmune or inflammatory disease has their immune response altered comprising the step of administering a therapeutically effective amount of the GL-2045 composition described herein to a subject, wherein the therapeutically effective amount of the GL-2045 composition alters the immune response in the subject. Ideally, this intervention treats the disease or condition in the subject. The altered immune response may be an increased or a decreased response and may involve altered cytokine levels including the levels of any of IL-IRA and other IL-1 family members, IL-6, IL-10, IL-8, IL-23, IL-7, IL-4, IL-12, IL-13, IL-17, IL-1 receptors, TNF-α, other TNF family members and TNF receptors, IFN-α, other interferon family members and interferon receptors or chemokine levels including the levels of any of the CCL, CXC, XC, and FAM19 chemokine family members. In a preferred embodiment, IL-6 or IL-8 is decreased in response to therapy. In an especially preferred embodiment, IL-6 and IL-8 are decreased in response to therapy and/or IL-10 or IL-IRA are increased in response to therapy. The invention is, however, not limited by any particular mechanism of action of the described biomimetics. The altered immune response may be an altered autoantibody level in the subject. The altered immune response may be an altered autoaggressive T-cell level in the subject.

For example, reducing the amount of TNF-alpha production in autoimmune diseases can have therapeutic effects. A practical application of this is anti-TNF-alpha antibody therapy (e.g. REMICADE®), which is clinically proven to treat plaque psoriasis, rheumatoid arthritis, psoriatic arthritis, Crohn's Disease, ulcerative colitis, and ankylosing spondylitis. These autoimmune diseases have distinct etiologies but share key immunological components of the disease processes related to inflammation and immune cell activity. A stradomer designed to reduce TNF-alpha production will likewise be effective in these and many other autoimmune diseases. The altered immune response profile may also be direct or indirect modulation to effect a reduction in antibody production, for example autoantibodies targeting a subject's own tissues, or altered auto-aggressive T-cell levels in the subject. For example, multiple sclerosis is an autoimmune disorder involving autoreactive T-cells which may be treated by interferon beta therapy. See, e.g., Zafranskaya M, et al., Immunology 2007 May; 121(1):29-39-Epub 2006 Dec. 18. An optimally manufactured stradomer designed to reduce autoreactive T-cell levels will likewise be effective in multiple sclerosis and may other autoimmune diseases involving autoreactive T-cells.

The GL-2045 composition described herein may be used to modulate expression of co-stimulatory molecules from an immune cell, including a dendritic cell, a macrophage, an osteoclast, a monocyte, or an NK cell or to inhibit in these same immune cells' differentiation, maturation, or cytokine secretion, including interleukin-12 (IL-12), or to increase cytokine secretion, including interleukin-10 (IL-10), interleukin-6 (IL-6), or IL-RA. A skilled artisan may also validate the efficacy of an optimized immunologically active biomimetic by exposing an immune cell to the optimized immunologically active biomimetic and measuring modulation of the immune cell function, wherein the immune cell is a dendritic cell, a macrophage, an osteoclast, or a monocyte. In one embodiment, the immune cell is exposed to the optimized immunologically active biomimetic in vitro, further comprising the step of determining an amount of a cell surface receptor or of a cytokine production, wherein a change in the amount of the cell surface receptor or the cytokine production indicates a modulation of the immune cell function. In another embodiment, the immune cell is exposed to the optimized immunologically active biomimetic in vivo in a model animal for an autoimmune disease, further comprising a step of assessing a degree of improvement in the autoimmune disease.

The GL-2045 composition described herein may also be used as a component of a device. In some embodiments, the GL-2045 provided herein may be coated on a device, such as a medical implant. For example, the optimally manufactured stradomers may be coated on a coronary stent or as part of nanoparticle therapy to enhance penetration and prolong drug release, for example for intra-ophthalmic use in uveitis or macular degeneration. The optimally manufactured stradomers described herein may also be used as a component of a diagnostic. In some embodiments, a skilled artisan may personalize therapy by determining, in which patients, use of a stradomer may be particularly beneficial. For example, the skilled artisan may expose a patient's immune cells to the immunologically active biomimetic and measure modulation of the immune cell's activation or maturation by flow cytometry or cytokine profile in order to identify high responders.

All references cited herein are incorporated by reference in their entireties.

EXAMPLES

Various approaches in manufacturing process were taken to optimize the combination of high protein titer, long viability with concomitant low cellular debris, and production of higher-order multimers of GL-2045. Specifically, the following aspects of the upstream manufacturing process were varied to determine the optimal conditions for GL-2045 products with the property of increased multimerization: basal media, type of feed, timing of feed, temperature shift, aeration, and shake flask conditions. In each instance, cell density, viability, protein titer, and multimerization were analyzed in order to identify optimal conditions. Further, aspects of the downstream manufacturing process, including buffers, wash protocols, and column selection, were varied to determine the optimal conditions for purification and filtration of GL-2045 wherein the optimal multimerization profile of GL-2045 was maintained. The following examples are provided by way of illustration only and not by way of limitation.

Example 1—Fractionation and Biolayer Interferometry Analysis of GL-2045

Figure 1B:
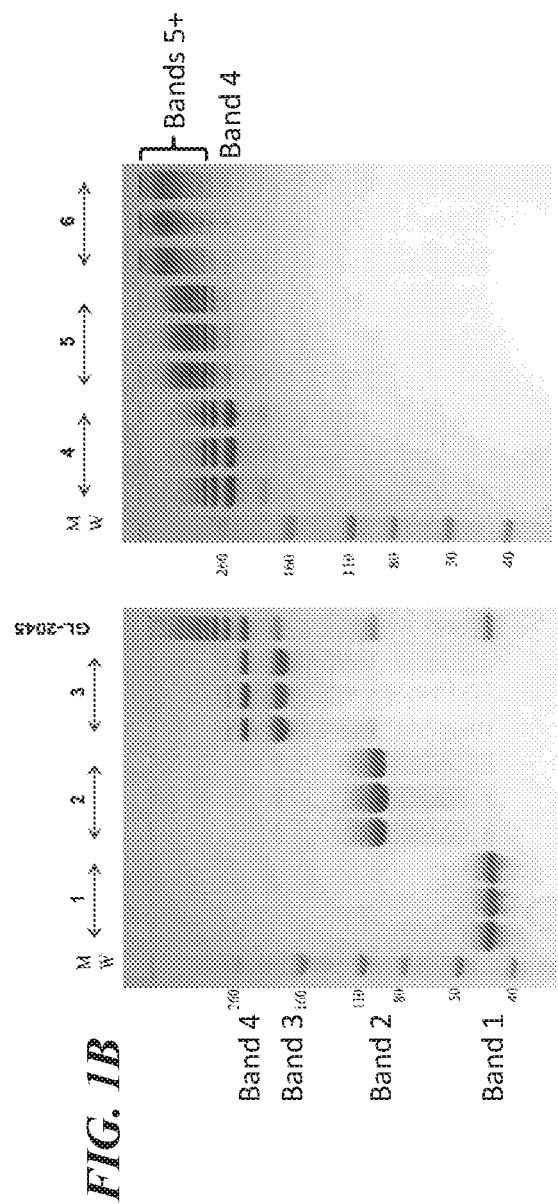

Solutions of GL-2045 were fractionated using a GE Hi-Load 26/60 Superdex 200 pg column (GE, #17-1071-01) in 0.05 M Tris-HCL+0.15 M NaCl buffer (pH 7.5). 3.2 mL GL-2045 solution was loaded at a flow rate of 2.6 mL/min. Six fractions (1-6) were collected in 2.0 mL volumes and protein concentration determined by UV measurement at 280 nm (FIG. 1A). Multimerization for each of the GL-2045 fractions was assessed. Briefly, samples of each of fractions 1-6 were loaded onto 4-12% non-reducing Nu-Page BT gels (Invitrogen, #NP0322BOX). Samples were run for approximately 3 hours at 150 volts. Results are provided in FIG. 1B and demonstrate distinct differences in the presence of higher order multimers of GL-2045 between Fractions 1-6. Fractions 1-3 are comprised of lower order multimers (e.g., bands 1-4). Fraction 1 is comprised nearly exclusively of homodimer having an apparent MW of 55 KD (Band 1, MW estimations from non-reducing SDS-PAGE). Fraction 2 is comprised of approximately 97/dimer of the homodimer having a MW of 110 KD (Band 2). Fraction 3 is comprised primarily of Bands 3 and 4 having MWs of 165 KD and 220 KD, respectively along with smaller amounts of Bands 2, 5 (MW=275 KD), 6 (MW=330 KD), and 7 (MW=385 KD). Fraction 4 is comprised predominantly of bands 4, 5, and 6, along with smaller amounts of Bands 3, 7, 8 (MW=440 KD) and higher order bands. However, Fractions 5 and 6 are comprised predominantly of higher order multimers (bands 5+).

Fractions of GL-2045 were analyzed for binding to FcγRIIIA receptor using a biolayer interferometry kinetic binding analysis. Biolayer interferometry detects the binding between a ligand immobilized on the biosensor tip surface and an analyte in solution. When binding occurs it produces an increase in optical thickness at the biosensor tip, which results in a wavelength shift (detected as a response unit of "RU"). The maximum binding level (RU max) is the maximum possible amount of sample binding at equilibrium that saturates the amount of ligand on the sensor surface.

His-tagged receptor proteins (5 μg/mL) were bound to an anti-His sensor tip (Anti-Penta-His HIS1K, ForteBio Cat. #18-5121) in 1× kinetic analysis buffer from ForteBio (Cat. #18-1092) for 300 seconds. The loaded sensor was transferred into 1× kinetic buffer without labeled receptors or ligands in order to obtain baseline measurements for 60 seconds. After obtaining a baseline, the on rate of the receptor/protein was measured by transferring the sensor tip to a 1× kinetics buffer containing the purified stradomer of choice for 60 seconds at concentrations of 50 μg/mL, 25 μg/g/mL, and 12.5 μg/mL. Off rate was measured for 300 seconds by transferring the sensor tip to a 1× kinetics buffer, and RU value, on rate value, dissociation rate and $K_d$ value was calculated using the ForteBio software.

Figure 2:
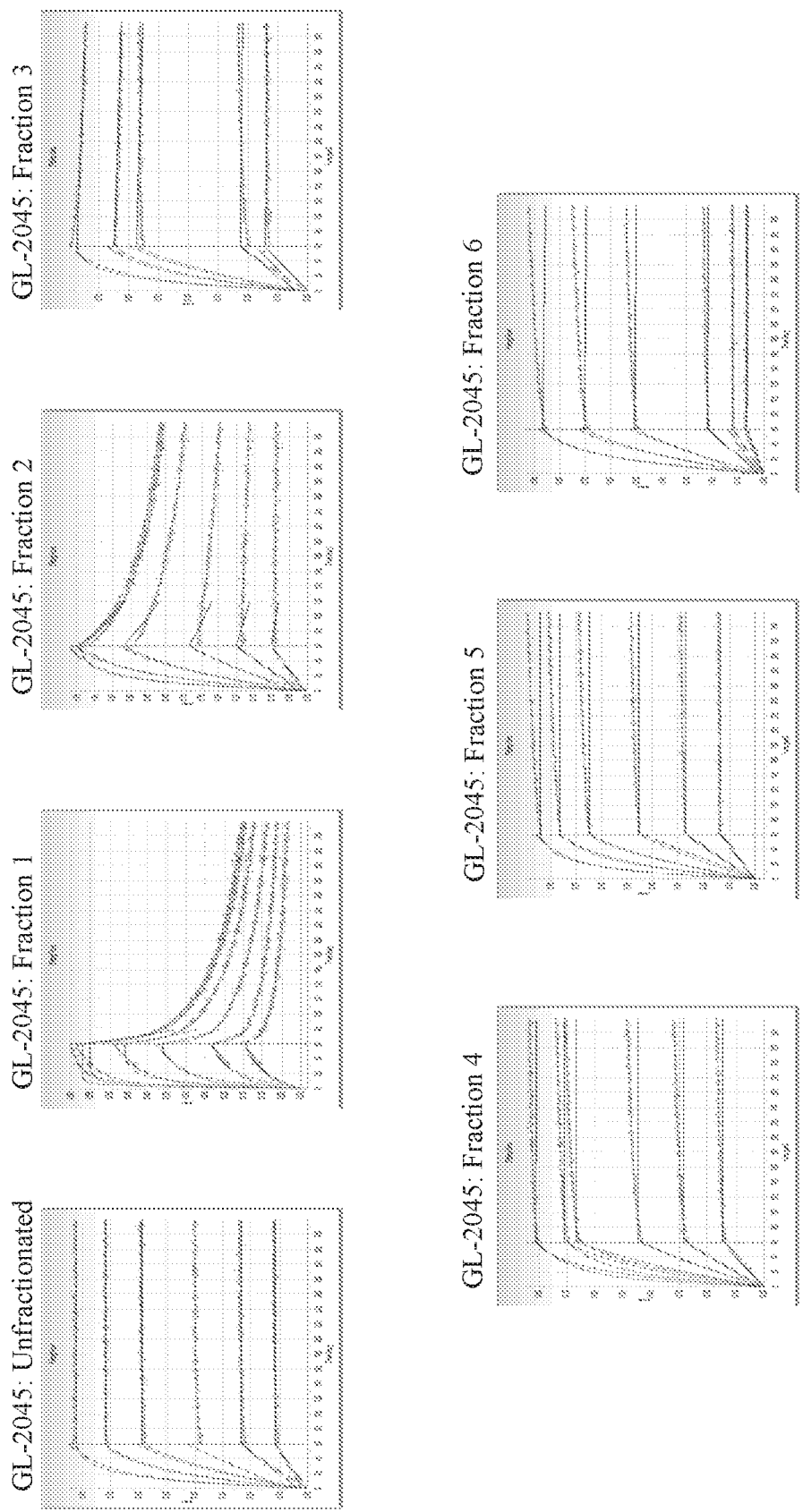
FIG. 2 illustrates biolayer interferometry analysis of GL-2045 fractions.

Binding curve results are shown in FIG. 2 and kinetic binding data calculated by ForteBio Octet software is provided in Table 2. These binding curves demonstrate higher avidity with an increasingly lower off rate for fractions containing higher molecular weight GL-2045 (e.g., Fractions 3, 4, 5, and 6) than observed for lower molecular weight fractions (e.g. Fractions 1 and 2), and indicate that the high molecular weight fractions of GL-2045 bind more avidly than the lower molecular weight fractions.

Figure 3B:
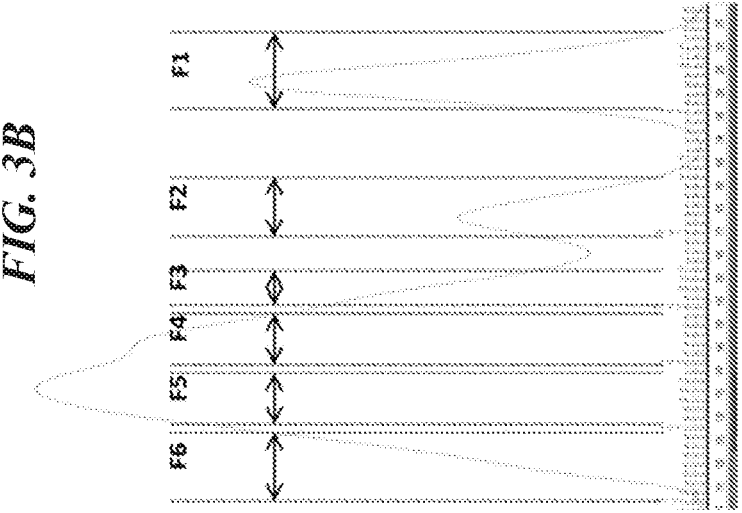
FIG. 3A-FIG. 3B illustrate gel analysis (FIG. 3A) and size-exclusion fractionation results (FIG. 3B) for GL-2045.
Figure 3A:
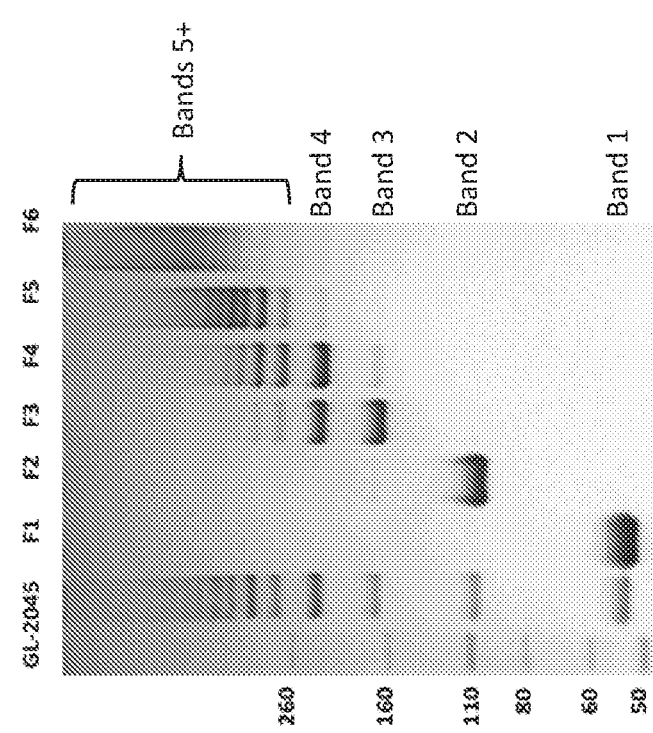
Figure 4B:
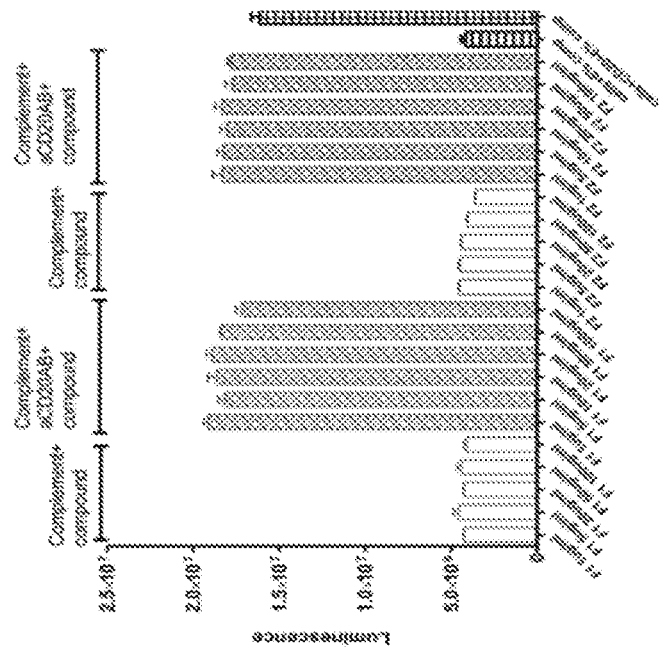
FIG. 4A-FIG. 4D illustrate the effects of GL-2045 fractions in a complement-dependent cell killing assay.
Figure 4A:
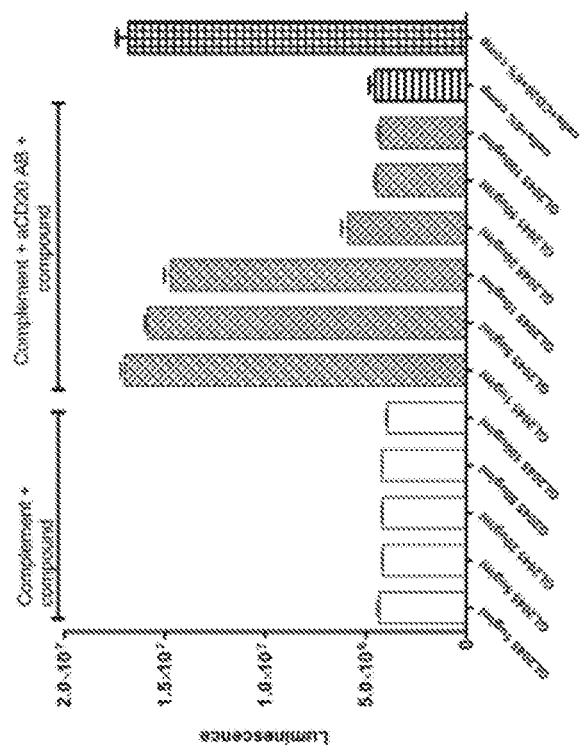
Figure 4C:
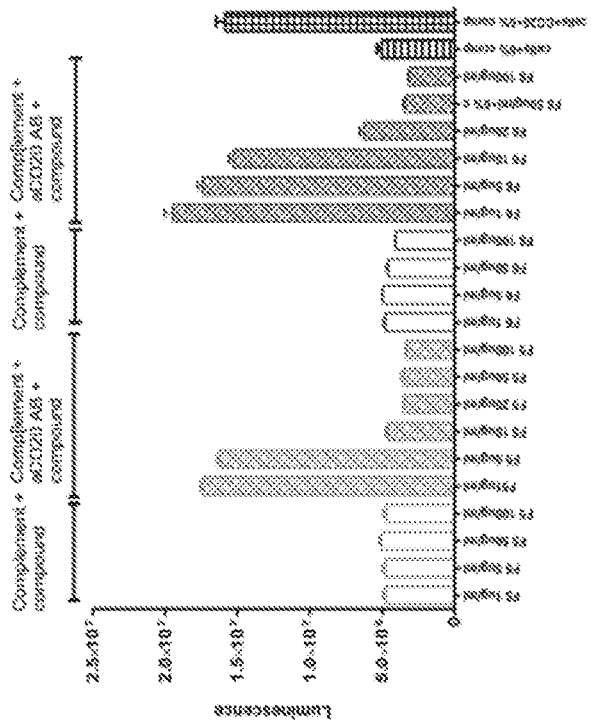
Figure 4D:
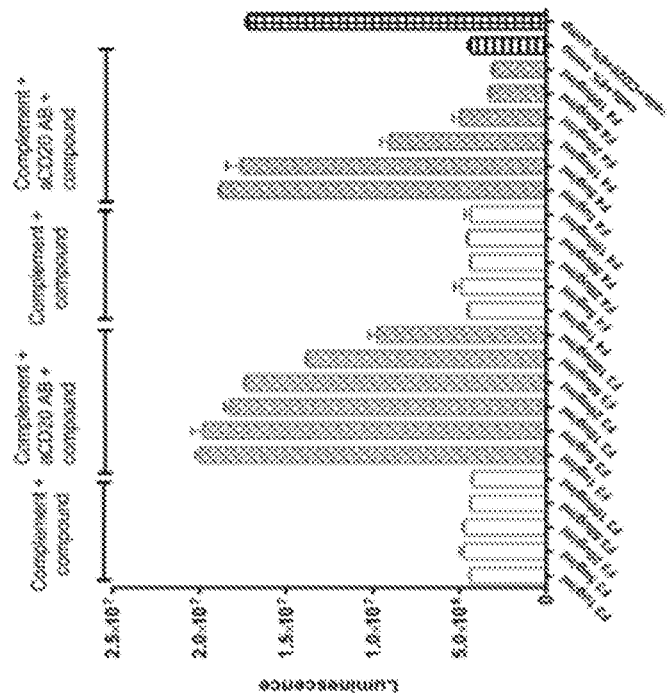

Example 2—Complement-Dependent Cell (CDC) Killing Assay with GL-2045 Fractions The ability of GL-2045 fractions to inhibit complement activation was assessed. GL-2045 was fractionated by size exclusion chromatography in to 6 fractions (FIG. 3A), each analyzed for multimerization on a non-reducing gel (FIG. 3B). To determine the effects of each fraction on complement activation, CD20-expressing Will-2 cells were incubated with an anti-CD20 monoclonal antibody for 20 minutes, after which the cells were centrifuged and re-suspended in fresh media. Cells were then incubated in a 96 well plate in media containing each of the fractions 1-6 described herein as well as unfractionated GL-2045 as comparison at one of six concentrations; 100 μg/mL, 50 μg/mL, 20 μg/mL, 10 μg/mL, 5 μg/mL, or 1 μg/mL. Serum was added to the cell suspensions in order to initiate complement dependent cell lysis, and the plate was incubated at 37° C. for 3 hours. Cell death was quantitated with the Promega Cytotox Glo Assay. The Cytotox Assay Reagent was added to each well of the plate, and the plate was incubated in the dark for 15 minutes at room temperature. The luminescence after 15 minutes was read on a Promega GloMax luminometer and cell death was calculated from this reading. Results are shown in FIGS. 4A-4D and demonstrate that fractions 5 and 6 (containing the higher molecular weight multimers in bands 5-13) showed more profound inhibition of CDC than the smaller molecular weight multimers present in fractions 1-4. It is also noted that only fractions that comprise band 4 and higher demonstrate effective inhibition of CDC, consistent with the polyvalent Fc binding of higher order multimers to hexameric C1 q.

Example 3—Binding of GL-2045 Fractions to FcγRIIIa

The binding of GL-2045 fractions to FcγRIIIa was determined. GL-2045 supernatant was purified by affinity chromatography with protein A HiTrap MabSelect Sure (GE #11-0034-95) with a binding buffer of 20 mM sodium phosphate, 0.15 M NaCl, pH 7.2 and was eluted with 0.1 M glycine, pH 2.7 (FIG. 5A). Affinity chromatography-purified GL-2045 was stored in 1×PBS, pH 7.2 (Quality Biological, Inc #119-069-101). A pool of purified GL-2045 was further dialyzed against 50 mM Sodium Acetate, pH 5.0 and polished by cat-ion exchange chromatography on a POROS CIEX column (GOPURE Column 1.2 cm D×10 cm L, Poros XS, Life Technologies, #4448885) with a binding buffer of 50 mM Sodium Acetate pH 5.0 and an elution gradient (0 to 100% elution buffer) with 50 mM Sodium Acetate, 1 M NaCl, pH 5.0. This polishing step was performed without the elimination of the highest order multimers and/or un-ordered aggregates from the final fractions. As a final step, the CIEX-polished GL-2045 was concentrated to a volume of

TABLE 2

Summary of Kinetic Binding Data for GL-2045 Fractions

| Fraction | $K_D$ | $K_{on}$ | $K_{dis}$ | $R_{max}$ | $R^2$ | $X^2$ |
|---|---|---|---|---|---|---|
| GL-2045 | 1.56E-11 | 4.73E+05 | 7.39E-06 | 0.830 | 0.999 | 0.0640 |
| 1 | 2.72E-07 | 1.00E+05 | 2.73E-02 | 0.507 | 0.986 | 0.0760 |
| 2 | 1.06E-08 | 3.34E+05 | 3.55E-03 | 0.673 | 0.995 | 0.0543 |
| 3 | 2.14E-10 | 5.94E+05 | 1.27E-04 | 0.786 | 0.997 | 0.1195 |
| 4 | 7.33E-12 | 5.99E+05 | 4.39E-06 | 0.852 | 0.991 | 0.2782 |
| 5 | 1.25E-12 | 1.18E+06 | 1.47E-06 | 0.853 | 0.993 | 0.1366 |
| 6 | 4.01E-11 | 1.08E+06 | 4.33E-05 | 0.930 | 0.994 | 0.0691 |

≤5 mL, and buffer exchanged against the gel filtration running buffer and injected into the gel filtration column (Hiload 26/60 Superdex 200 pg (GE #17-1071-01)) using 0.05 M Tris-HCl+0.15 M NaCl, pH 7.5 as running buffer (Tris HCL, pH 7.5 Teknova #T1075). Fractions were then analyzed for multimerization by gel analysis (FIG. 5B and FIG. 5C).

Figure 6B:
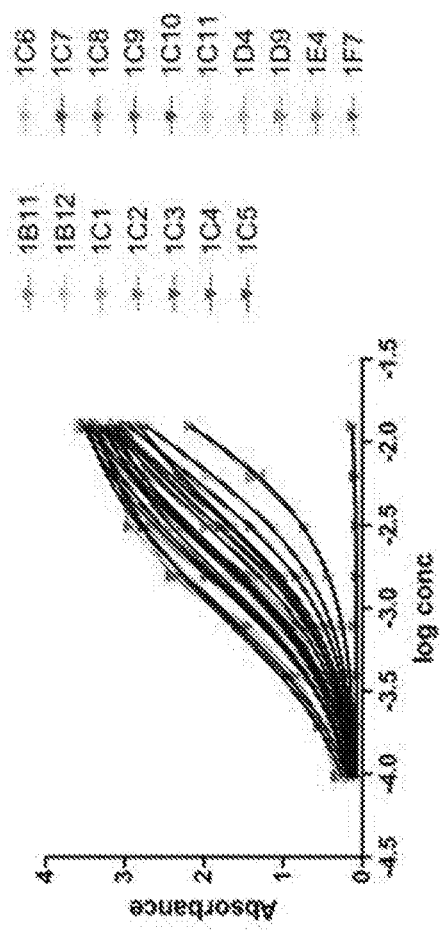
FIG. 6A-FIG. 6B illustrate the binding of eluted fractions shown in FIG. 5 to FcγRIIa (FIG. 6A) and the best-fit curve (FIG. 6B).
Figure 6A:
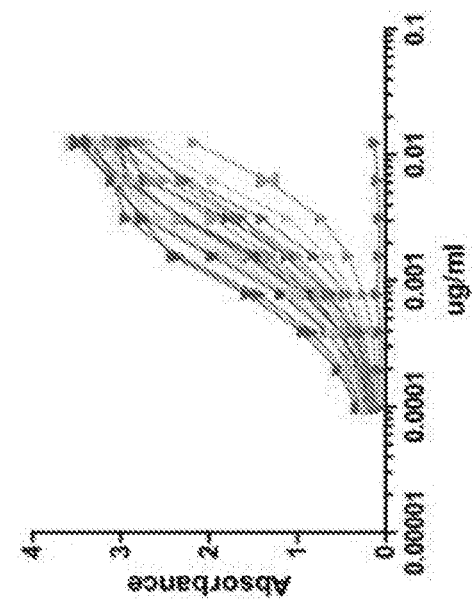

Binding of fractionated GL-2045 to FcγRIIIa was determined using an FcγRIIIa ELISA binding assay. Briefly, 96 plates were coated with recombinant FcγRIIIa and allowed to react with GL-2045. After washing, the amount of FcγRIIIa-bound material was determined using an Fc detecting mAb in an ELISA based assay (FIG. 6A and FIG. 6B). $EC_{50}$ values for each fraction are shown in Table 3. These results demonstrate that higher order multimers (Fractions 1C4, 1C5, 1C6, 1C7, 1C8, 1C9, 1C10, and 1C11) demonstrate more avid binding, noted by a low $EC_{50}$, to FcγRIIIa than lower order multimers (Fractions 1D9, 1E4 and 1F7) and, surprisingly, more avid binding than the highest molecular weight multimers (Fractions 1C3, 1C2, 1C1, 1B12, 1B11. The very highest molecular weight fractions are presumed to comprise some lower potency high molecular weight aggregated fractions along with the highly functional highest order multimers (e.g., Fractions 1B11, 1B12, 1C1, 1C2, and 1C3). These results indicate very surprisingly that not all high molecular weight fractions of GL-2045 demonstrate increased binding to FcγRs, likely due to effects of un-ordered aggregation of the homodimer as opposed to the formation of highly-ordered, high molecular weight multimers. These data indicate the need for optimized downstream manufacturing methods (including optimized conditions for protein A purification, ion exchange chromatography, and hydrophobic interaction chromatography) in combination with the optimal upstream manufacturing methods to result in the production and retention of high-molecular weight, higher order multimers and elimination of un-ordered, high molecular weight aggregates (e.g., 1B11 and 1B12), which are less effective at binding target low-affinity receptors (see $EC_{50}$ value for 1B11 and 1B12 in Table 3).

TABLE 3

$EC_{50}$ Values for GL-2045 Fractions Binding to FcγRIIIa

| Fraction | AC/CIEX EC50 ng/mL |
|---|---|
| 1B9 | NT |
| 1B10 | NT |
| 1B11 | 27.2 |
| 1B12 | 10.8 |
| 1C1 | 4.96 |
| 1C2 | 7.09 |
| 1C3 | 3.68 |
| 1C4 | 1.92 |
| 1C5 | 2.33 |
| 1C6 | 1.59 |
| 1C7 | 1.56 |
| 1C8 | 1.01 |
| 1C9 | 2.52 |
| 1C10 | 0.870 |
| 1C11 | 1.60 |
| 1D4 | 2.26 |
| 1D5 | NT |
| 1D9 | 3.15 |
| 1E4 | 3.82 |
| 1E8 | NT |
| 1F | 15.7 |
| 1F8 | NT |

NT = Not Tested

Example 4—C5a-Induced Chemotactic Analysis of GL-2045 Fractions

Figure 7:
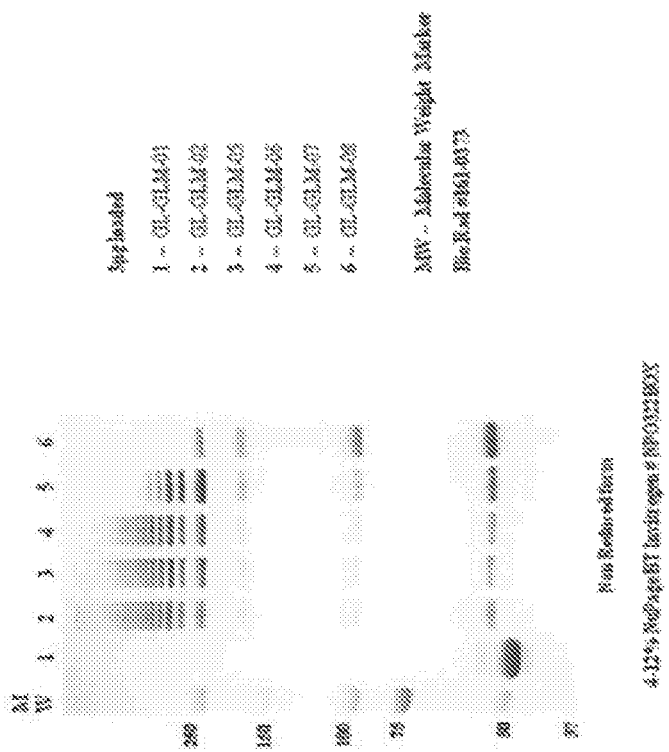
FIG. 7 illustrates SDS-Page analysis of anion exchange fractions: GL-GLM-01=recombinant, unfractionated Fc (G001), GL-GLM-02=unfractionated GL-2045, GL-GLM-05=fractionated GL-2045 at pH 6.0, GL-GLM-06=fractionated GL-2045 at pH 6.5, GL-GLM-07=fractionated GL-2045 at pH 7.0, GL-GLM-08=fractionated GL-2045 at pH 7.5.

GL-2045 cell culture was grown in PowerCHO2 media (Lonza, #U21-070) with L-Glutamine (Lonza, #17-605E) and HT supplement (Life Technologies, #11067-030). GL-2045 supernatant was purified by affinity chromatography with protein A HiTrap MabSelect Sure (GE, #11-0034-95) then fractionated with AIEX HiScreen Q FF (GE, #28-9505-10) using different pH conditions to separate the low molecular bands to the high molecular bands. Results are shown in FIG. 7 (GL-GLM-01=recombinant, unfractionated Fc (G001), GL-GLM-02=unfractionated GL-2045, GL-GLM-05=fractionated GL-2045 at pH 6.0, GL-GLM-06=fractionated GL-2045 at pH 6.5, GL-GLM-07=fractionated GL-2045 at pH 7.0, GL-GLM-08=fractionated GL-2045 at pH 7.5). Finally, the different fractions were concentrated and dialyzed against HBSS (Lonza, #10-527F).

GL-2045 supernatant was purified by affinity chromatography with protein A (pA) HiTrap MabSelect Sure (GE, #11-0034-95) with a binding buffer of 20 mM sodium phosphate, 0.15 M NaCl pH 7.2. After a first wash with the binding buffer and a second wash a buffer comprising 1 M NaCl, 5 mM EDTA, 2 M Urea, 50 mM phosphate pH 7.0, the protein bound to pA was eluted with 0.1M glycine, pH 2.7.

Affinity chromatography-purified GL-2045 was stored in 1×PBS, pH 7.0 (Quality Biological, Inc #119-069-101). 4 batches of purified GL-2045 were further diluted (6×) with 50 mM Tris-HCL at pH 6.0, 6.5, 7.0 or 7.5 and purified by anion exchange chromatography on a HiScreen Q FF column with a binding buffer of 50 mM Tris-HCL pH 6.0, 6.5, 7.0 or 7.5 and eluted by gradient elution (0 to 100% elution buffer) with 50 mM Tris-HCL+1 M NaCl at pH 6.0, 6.5, 7.0, 7.5.

Figure 8:
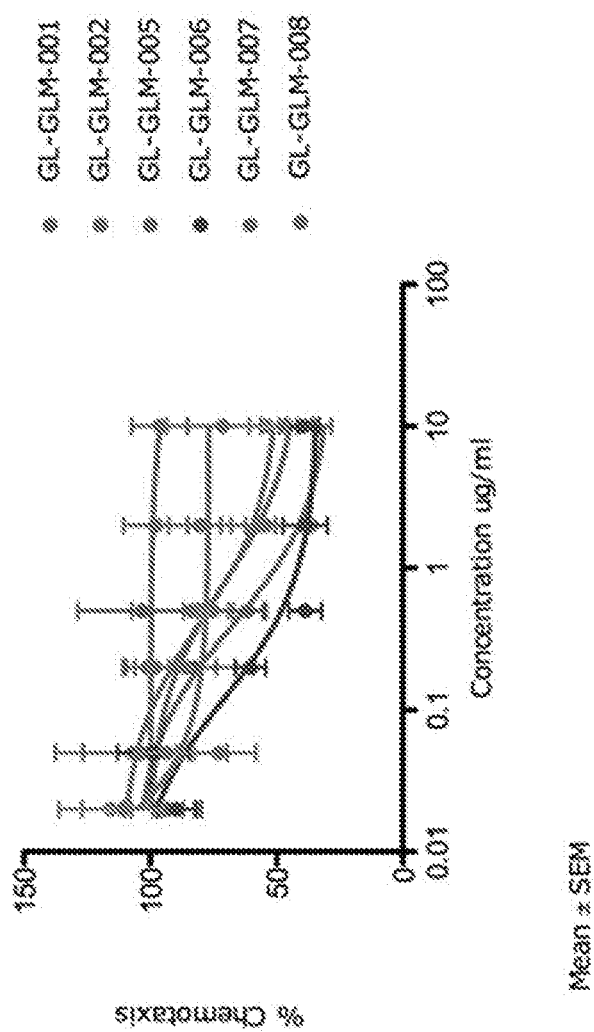
FIG. 8 illustrates the results of a neutrophil chemotaxis assay with C5a as the chemoattractant in the presence of unfractionated or fractionated GL-2045: GL-GLM-01=recombinant, unfractionated Fc (G001), GL-GLM-02=unfractionated GL-2045, GL-GLM-05=fractionated GL-2045 at pH 6.0, GL-GLM-06=fractionated GL-2045 at pH 6.5, GL-GLM-07=fractionated GL-2045 at pH 7.0, GL-GLM-08=fractionated GL-2045 at pH 7.5.

These purified fractions were utilized to determine the effects of GL-2045 fractions on neutrophil chemotaxis. Briefly, complement C5a was added as a chemoattractant to the lower well of a Boyden chamber at a concentration of 1 nM. Prior to addition to the Boyden chamber, neutrophils (final concentration $2.25 \times 10^6$ cells/mL, purified from whole blood from PBMCs) were pre-incubated with the indicated GL-2045 fractions (0.02-10 pg/mL final concentrations pg/mL) or recombinant Fc control (GLM-001, G001) for 30 minutes. Cell suspensions were then added to the upper well of the Boyden chamber and incubated for 25 minutes. Following the incubation period, migrated populations were assessed by counting the number of cells in the lower chamber for each condition and a percent chemotaxis for each condition was determined (FIG. 8). No chemotaxis was observed for GL-GLM-001 (recombinant Fc control, G001). Higher order multimers (Fractions GL-GLM-002, GL-GLM-005, GL-GLM-006, and GL-GLM-007 comprising bands 5-13) demonstrated more avid inhibition of C5a-induced chemotaxis than lower order multimers (Fraction GL-GLM-008 comprising bands 1-4).

The data provided in Examples 1-4 demonstrate the enhanced efficacy of higher-order multimers on GL-2045. Based on the above data, upstream manufacturing protocols were tested in order to determine the optimal conditions for the specific production of higher-order multimers (e.g. bands 5+ in FIGS. 1, 3, 5, and 7) of GL-2045 in order to achieve maximum biological efficacy.

Example 5—Base Media Screening in GL-2045 Production

The purpose of this experiment was to test the effect of a panel of basal medias on GL-2045 protein titer, cell viability, cell density, and GL-2045 multimerization.

GL-2045 was grown in ProCHO5 media (Lonza #12-766Q) with L-Glutamine (Lonza #17-605E) and sodium hypoxanthine and thymidine (HT, Gibco #11067-030) in a shaker incubator at 37 C and 5% $CO_2$. After passaging, the cells were washed and inoculated in duplicate at $0.5 \times 10^6$ cells/mL in Selected Media (shown in Table 4) into a 50 mL Tube Spin. Each tube contained 10 mL of culture and was placed in a Kuhner brand maglev shaker incubator at 37° C., 5% CO2, 80% humidity and 180 rpm rotation speed. At day 4, 8, and 10, one milliliter of sample was taken from each culture for measuring cell density, cell viability and glucose level. Samples were centrifuged and supernatants were stored at +4° C. Selected Medias that did not list 4 mM L-Glutamine and 1× sodium hypoxanthine and thymidine were supplemented with L-Glutamine and HT as components. Growth conditions for Selected Media are shown in Table 4.

TABLE 4

Selected Media Growth Conditions

| Medium | Manufacturer | L-Glutamine | HT | % CO2 | % Humidity |
|---|---|---|---|---|---|
| CD FortiCHO | LifeTechnologies | 4 mM | 1X | 5 | 80 |
| TC-42 (CHOMACS CD) | TeutoCell (Xell) | 4 mM | 1X | 5 | 80 |
| Hyclone CDM4CHO | Thermo Scientific | 4 mM | — | 5 | 80 |
| Hyclone ADCF MAB | Thermo Scientific | 4 mM | — | 5 | 80 |
| PowerCHO3 CD | Lonza | 4 mM | 1X | 5 | 80 |
| Ex-Cell CHO5 | Sigma-Aldrich | 4 mM | — | 5 | 80 |
| BalanCD CHO Growth A | Irvine | 4 mM | 1X | 5 | 80 |
| EX-CELL CD CHO | Sigma Aldrich | 4 mM | — | 5 | 80 |
| CHO-S-SFM II | LifeTechnologies | 4 mM | — | 5 | 80 |
| ExpiCHO Expression | LifeTechnologies | — | 1X | 5 | 80 |
| GE Healthcare SFM4CHO | GE Healthcare | 4 mM | 1X | 5 | 80 |
| ClonaCell-CHO CD | Stemcell Tech. | 4 mM | 1X | 5 | 80 |
| GE Healthcare HYQ SFX-CHO LM | GE Healthcare | 4 mM | 1X | 5 | 80 |
| Cell Vento CHO 210 | Millipore | 4 mM | 1X | 5 | 80 |
| ActiCHO P | GE | 4 mM | — | 5 | 80 |
| Cell Vento CHO 110 | Millipore | 4 mM | 1X | | 80 |
| CD Hybridoma | Thermo Scientific | 4 mM | — | 5 | 80 |
| CD OptiCHO | Thermo Scientific | 4 mM | 1X | 5 | 80 |
| PowerCHO-GS | Sartorius AG | 4 mM | — | | 80 |

Figure 9:
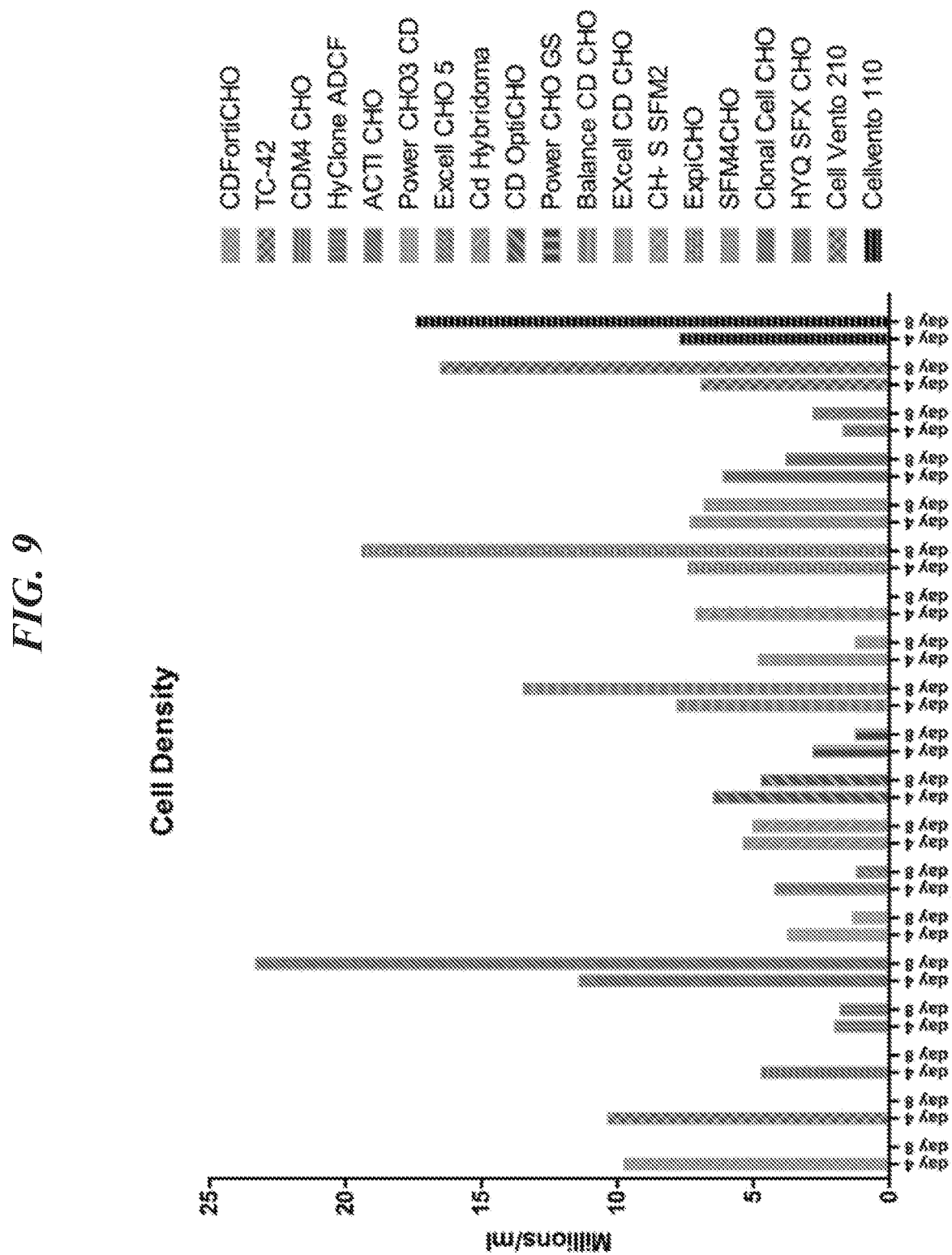
FIG. 9 illustrates cell density (in millions/mL) of CHO cells grown in a panel of different media on days 4, 8, and 10 of culture.
Figure 10:
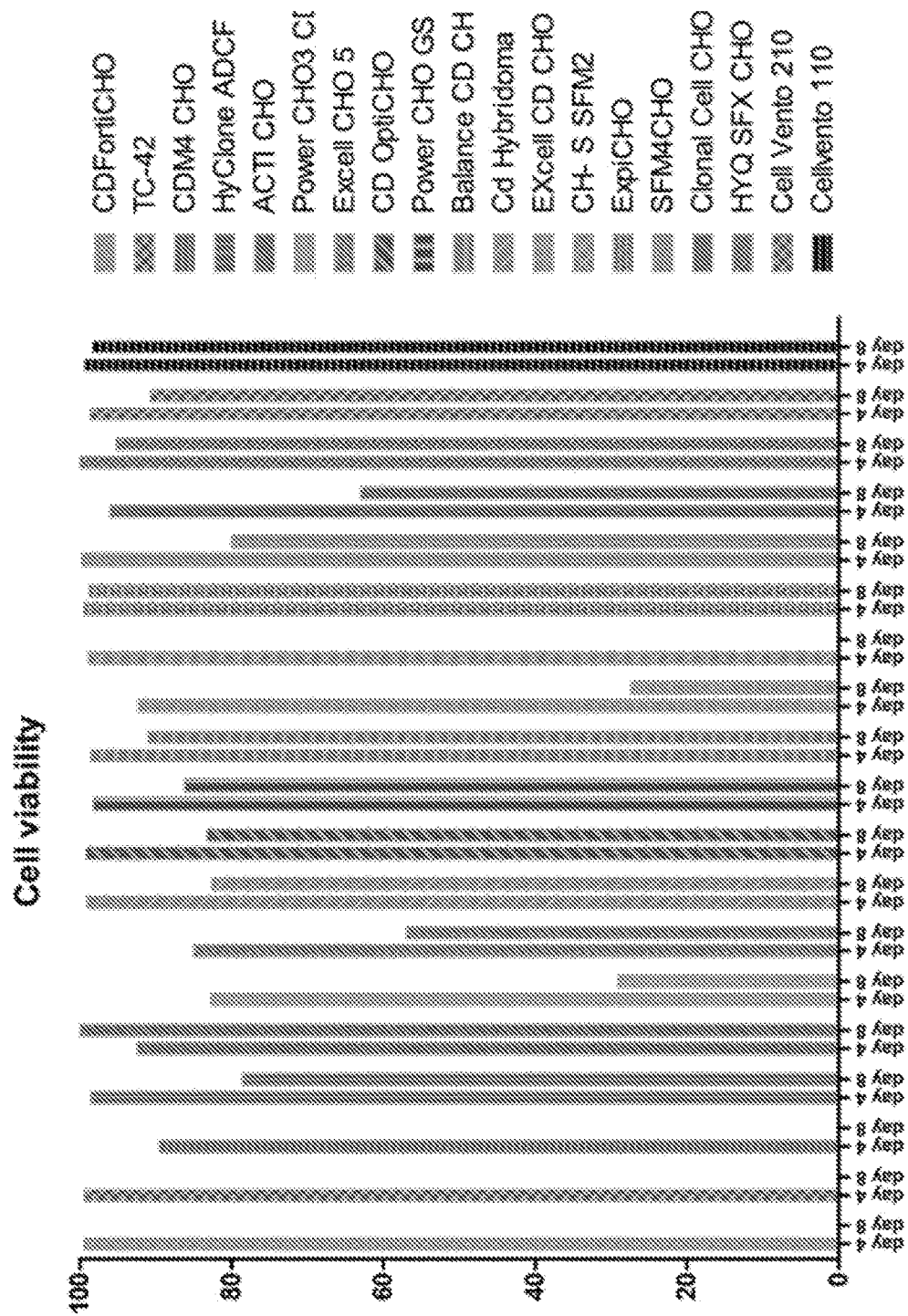
FIG. 10 illustrates cell viability (%) of CHO cells grown in a panel of different media on days 4, 8, and 10 of culture.

The GL-2045 cell cultures grown in selected media were assessed for cell density, cell viability, protein titer, and percent of higher order multimers. Cell density and cell viability assessments were performed by mixing cells with Trypan Blue. Viable and dead cells were counted using a manual cell counter. Data for Day 4 and Day 8 of culture are shown for cell density (FIG. 9, Table 5) and cell viability (FIG. 10, Table 6). Of the 19 media tested, the greatest cell density at day 4 was observed with ActiCHO P, CHOMACS CD, and CD FortiCHO. By day 8, the trend in cell density was negative for all media except for ActiCHO P, BalanCD CHO, ExpiCHO, Cell Vento CHO 210, and Cell Vento CHO 210, compared to day 4. Of the 19 media, the greatest cell viability at day 8 tested was observed with ActiCHO P followed by ExpiCHO, Cell Vento CHO 110, and HYQ SFX-CHO LM. The only media of the 19 media tested to have a positive trend in cell viability from Day 4 to Day 8 was ActiCHO P. Therefore, the only media which produces high cell density at Day 4 and does not have a negative trend for cell density at Day 8 is ActiCHO P.

TABLE 5

GL-2045-Producing CHO Cell Density

| Medium | Day 4 ($10^6$/mL) | Day 8 ($10^6$/mL) |
|---|---|---|
| CD FortiCHO | 9.75 | 0.00 |
| TC-42 (CHOMACS CD) | 10.35 | 0.00 |
| Hyclone CDM4CHO | 4.70 | 0.00 |
| Hyclone ADCF MAB | 2.00 | 1.81 |
| PowerCHO3 CD | 3.72 | 1.34 |
| Ex-Cell CHO5 | 4.20 | 1.20 |
| ActiCHO P | 11.40 | 23.30 |
| BalanCD CHO Growth A | 7.80 | 13.46 |
| EX-CELL CD CHO | 4.80 | 1.24 |
| CHO-S-SFM II | 7.10 | 0.00 |
| ExpiCHO Expression | 7.40 | 19.40 |
| SFM4CHO | 7.30 | 6.80 |
| ClonaCell-CHO CD | 6.10 | 3.80 |
| HYQ SFX-CHO LM | 1.70 | 2.80 |
| Cell Vento CHO 210 | 6.90 | 16.50 |
| Cell Vento CHO 110 | 7.70 | 17.40 |
| CD Hybridoma | 5.35 | 5.00 |
| CD OptiCHO | 6.45 | 4.70 |
| PowerCHO-GS | 2.80 | 1.25 |

TABLE 6

GL-2045-Producing CHO Cell Viability

| Medium | Day 4 (% Viable) | Day 8 (% Viable) |
|---|---|---|
| CD FortiCHO | 99.5 | 0.0 |
| TC-42 (CHOMACS CD) | 99.4 | 0.0 |
| Hyclone CDM4CHO | 89.5 | 0.0 |
| Hyclone ADCF MAB | 98.5 | 78.6 |
| PowerCHO3 CD | 82.7 | 29.1 |
| Ex-Cell CHO5 | 85.0 | 56.9 |
| ActiCHO P | 92.4 | 100.0 |
| BalanCD CHO Growth A | 98.5 | 91.0 |
| EX-CELL CD CHO | 92.2 | 27.3 |
| CHO-S-SFM II | 98.9 | 0.0 |
| ExpiCHO Expression | 99.5 | 98.8 |
| SFM4CHO | 99.7 | 80.0 |
| ClonaCell-CHO CD | 96.0 | 62.9 |
| HYQ SFX-CHO LM | 100.0 | 95.2 |
| Cell Vento CHO 210 | 98.6 | 90.7 |
| Cell Vento CHO 110 | 99.4 | 98.3 |
| CD Hybridoma | 99.1 | 82.6 |
| CD OptiCHO | 99.2 | 83.2 |
| PowerCHO-GS | 98.2 | 86.2 |

Figure 11:
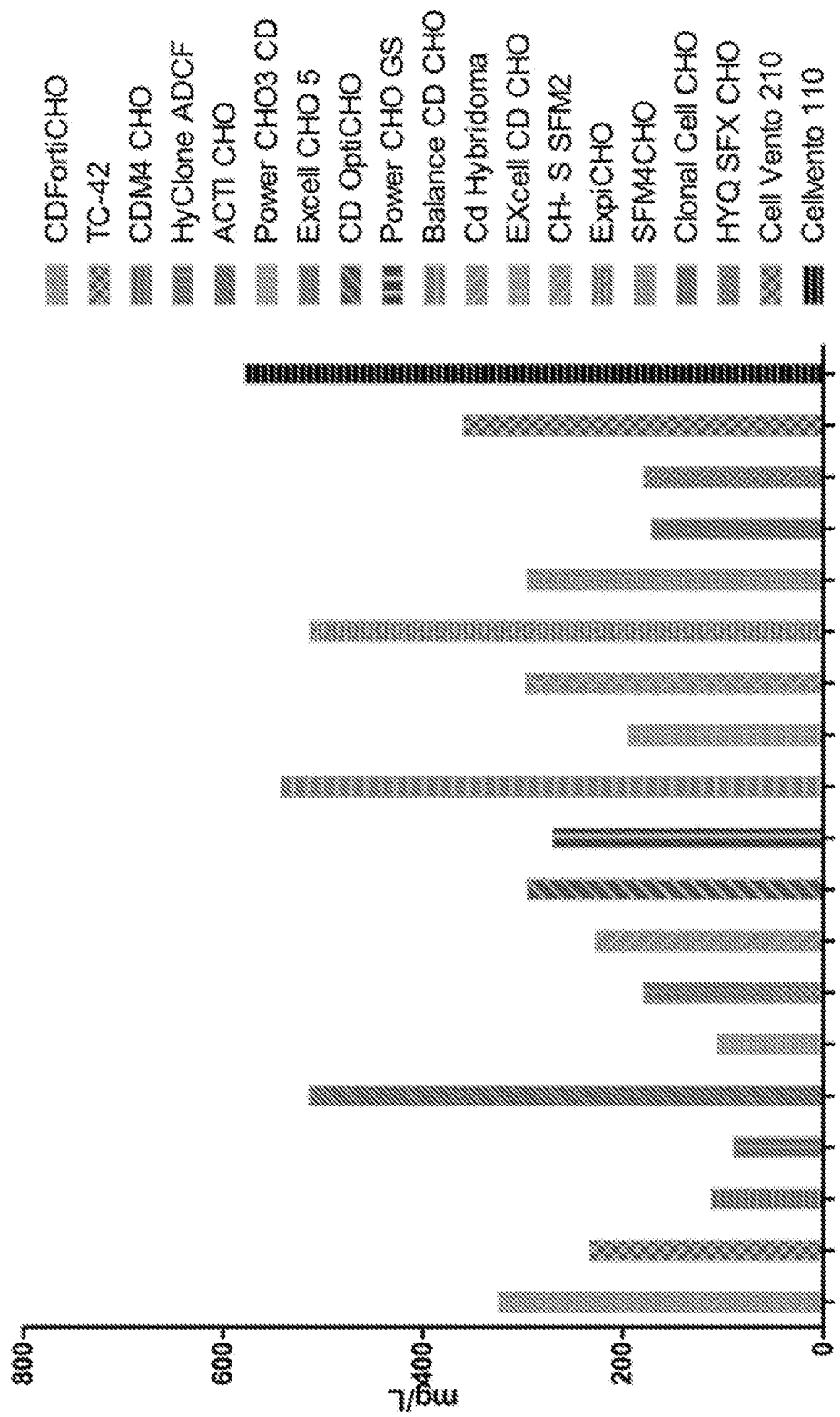
FIG. 11 illustrates protein titer (mg/mL) of CHO cells grown in a panel of different media on day 10 of culture.

Cultures were spun down on day 10, filtered at 0.2 μm and kept at 4° C. until purification using a protein A affinity column. For purification, supernatant cultures were purified by affinity chromatography with 1 mL protein A column HiTrap MabSelect SuRe (GE, #11-0034-93) with a binding buffer of 20 mM sodium phosphate, 0.15M NaCl, pH 7.2. The column-bound protein was washed with the binding buffer followed by a second wash with 1 M NaCl, 5 mM EDTA, 2 M Urea, 50 mM phosphate, pH 7.0. GL-2045 bound to the column was eluted with 0.1 M glycine pH 2.7 and desalted in 1×PBS at pH 7.0 thru HiPrep 26/10 desalting column (GE, #17-5087-01). All samples purified were stored at 4° C. Measurements of protein titer were performed by biolayer interferometry (Octet) (FIG. 11 and Table 7). Of the 19 base media tested, the greatest protein titer at day 10 was observed with Cell Vento CHO 110 followed by BalanCD CHO Growth A Medium, ActiCHO P, and ExpiCHO. A significant drop in titer occurred with other media.

TABLE 7

GL-2045 Titer

| Medium | Protein (mg/L) |
|---|---|
| Cell Vento CHO 110 | 577.9 |
| BalanCD CHO Growth A | 542.0 |
| ActiCHO P | 514.4 |
| ExpiCHO Expression | 513.0 |
| Cell Vento CHO 210 | 359.1 |
| CD FortiCHO | 323.7 |
| CHO-S-SFM II | 296.2 |
| CD OptiCHO | 295.8 |
| SFM4CHO | 295.8 |
| PoweiCHO-GS | 269.9 |
| TC-42 (CHOMACS CD) | 232.4 |
| CD Hybridoma | 226.7 |
| EX-CELL CD CHO | 194.4 |
| HYQ SFX-CHO LM | 179.2 |
| Ex-Cell CHO5 | 179.2 |
| ClonaCell-CHO CD | 170.9 |
| Hyclone CDM4CHO | 111.6 |
| PowerCHO3 CD | 105.5 |
| Hyclone ADCF MAB | 89.4 |

Figure 12A:
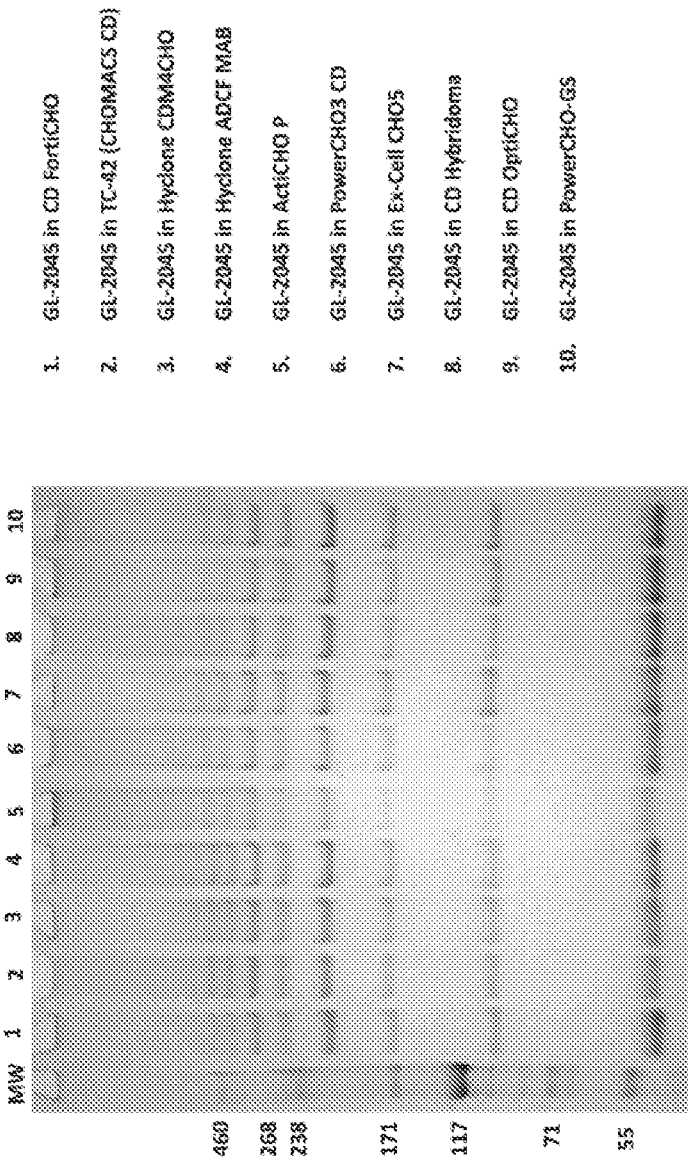
FIG. 12A-FIG. 12B illustrate gel analyses of GL-2045 protein produced from CHO cells grown in the panel of media illustrated in FIGS. 9-11.
Figure 12B:
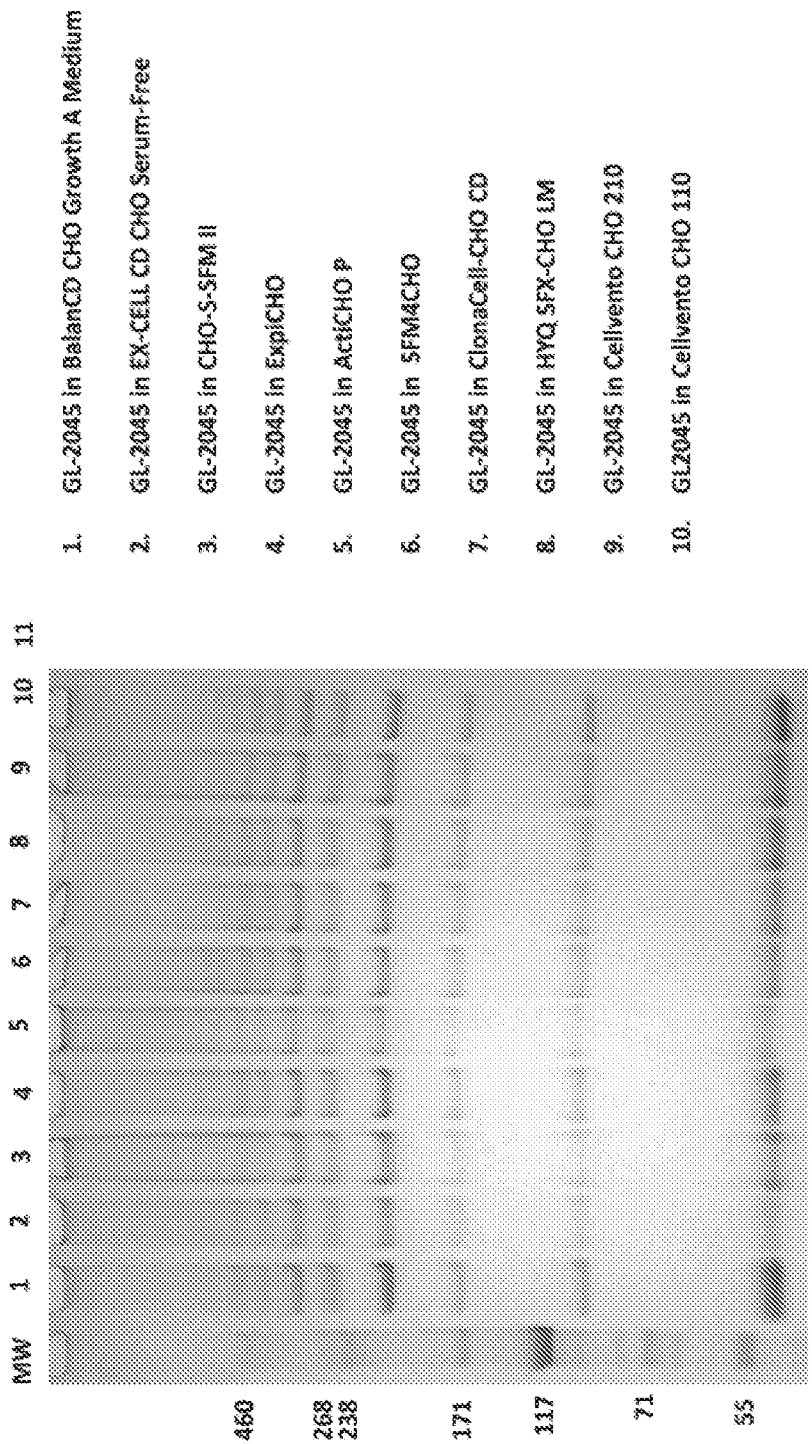

In order to determine the percent of higher order multimers, each purified culture was run (in non-reduced form) onto an SDS-PAGE gel (NuPage 3-8% Tris-Acetate gel, Life Technologies, #EA03752BOX). 2 pg of protein was diluted in 3 μL of sample buffer (NuPage, LDS (4×), Life Technologies, #NP0007), 20 μM of Iodoacetamide (Bio Rad #163-2109) and deionized (DI) water to a final volume of 10 μL. Samples were heated at 80° C. for 10 minutes and loaded onto the gel and run at 150V for 1 hour and 25 minutes using running buffer (Tris-Acetate SDS (20×) (Life Technologies, #LA0041)). Gels were washed in DI water, stained with SimplyBlue Safe (Life Technologies, #LC6060) and destained in DI water. After a complete destaining a picture was taken using G:BOX system from Syngene and the banding pattern was analyzed by densitometry with Gene-Tools, Syngene software. The intensity in each individual band in each lane was measured (FIG. 12A and FIG. 12B).

Unexpectedly, the greatest percent of higher order multimers above band 4 of the 19 media tested was observed with ActiCHO P followed by EX-CELL CD CHO and CH-S SFM2 (Table 8). These data indicate that increased percentage of higher-order multimers is an independent variable to be controlled and is not simply correlated with an increase in total protein titer. ActiCHO P resulted in the third highest protein titer and greatest level of multimerization (45.9% of protein present in bands 5+), while Cell Vento CHO 110 resulted in the greatest protein titer but a substantially lower level of multimerization (32.6% of protein present in bands 5+).

TABLE 8

GL-2045 Multimerization Analysis

| Medium | % Bands (1-4) | % Bands (5+) |
|---|---|---|
| ActiCHO P | 54.1 | 45.9 |
| EX-CELL CD CHO | 59.4 | 40.6 |
| CHO- SSFM2 | 61.2 | 38.8 |
| TC-42 | 64 0 | 36.0 |
| SFM4CHO | 64.1 | 35.9 |
| Power CHO3 CD | 65 3 | 34.7 |
| Hyclone ADCF | 66.1 | 33.9 |
| Cell Vento 210 | 66.5 | 33.5 |
| Cell Vento 110 | 67.4 | 32.6 |
| CD OptiCHO | 67.6 | 32.4 |
| ExpiCHO | 68.1 | 31.9 |
| CD Hybridoma | 68.6 | 31.4 |
| Power CHO GS | 68.7 | 31.3 |
| Balance CD CHO | 70.0 | 30.0 |
| CDM4 CHO | 70.2 | 29.8 |
| Clonal Cell CHO | 70.4 | 29.6 |
| CD FortiCHO | 70 4 | 29.6 |
| HYQ SFX CHO | 70.8 | 29.2 |
| EX-CELL CHO 5 | 71.4 | 28.6 |

Example 6—Media Screening of GL-2045 with Feeds

Recommended Feeding Schedules

Based on the results of the experiments in Example 5, four base media associated with the highest GL-2045 protein titers and three base media associated with the lowest GL-2045 protein titers were subjected to a repeat experiment in which commercially available feeds were provided during culture. Cell Vento 110 and ExpiCHO, which produced high titers, were not selected for the feed experiment because no manufacturer-recommended feeds were identified. Cell Vento CHO 110 is a complete media to be used for cell adaptation without feeds, while Cell Vento 210 is used for culture in combination with feeds. Media and feed combinations used in this experiment are detailed in Table 9.

TABLE 9

Media + Feed combinations

| Media | Feed |
|---|---|
| Cell Vento CHO-210 EMD Millipore #1025531000 | Cell Vento Feed-210 + Cysteine /Tyrosine + Glucose EMD Millipore #1.02488 |
| BalanCD CHO Growth A Medium IRVINE #91118 | BalanCD CHO Feed I IRVINE #91127 |
| CD FortiCHO Life Technologies #A11483-01 | CD EfficientFeed C AGT Nutriment Supplement Life Tech. #A13275-04 |
| CDM4CHO Hyclone #SH30558.01 | Cell Boost 4 (PS307) Hyclone SH30857 |
| PowerCHO3 CD Lonza #12-772Q | Power Feed A + L-Glutamine #BE02-044Q |
| ADCF-Mab Hyclone #SH30349.02 | Cell Boost 4 (PS307) Hyclone #SH30857 |
| ActiCHO P media PAA #U21-070 | Feed A, Feed B PAA #U15-072, PAA #U05-034* |

*PAA subsequently became part of GE Lifesciences

Figure 13B:
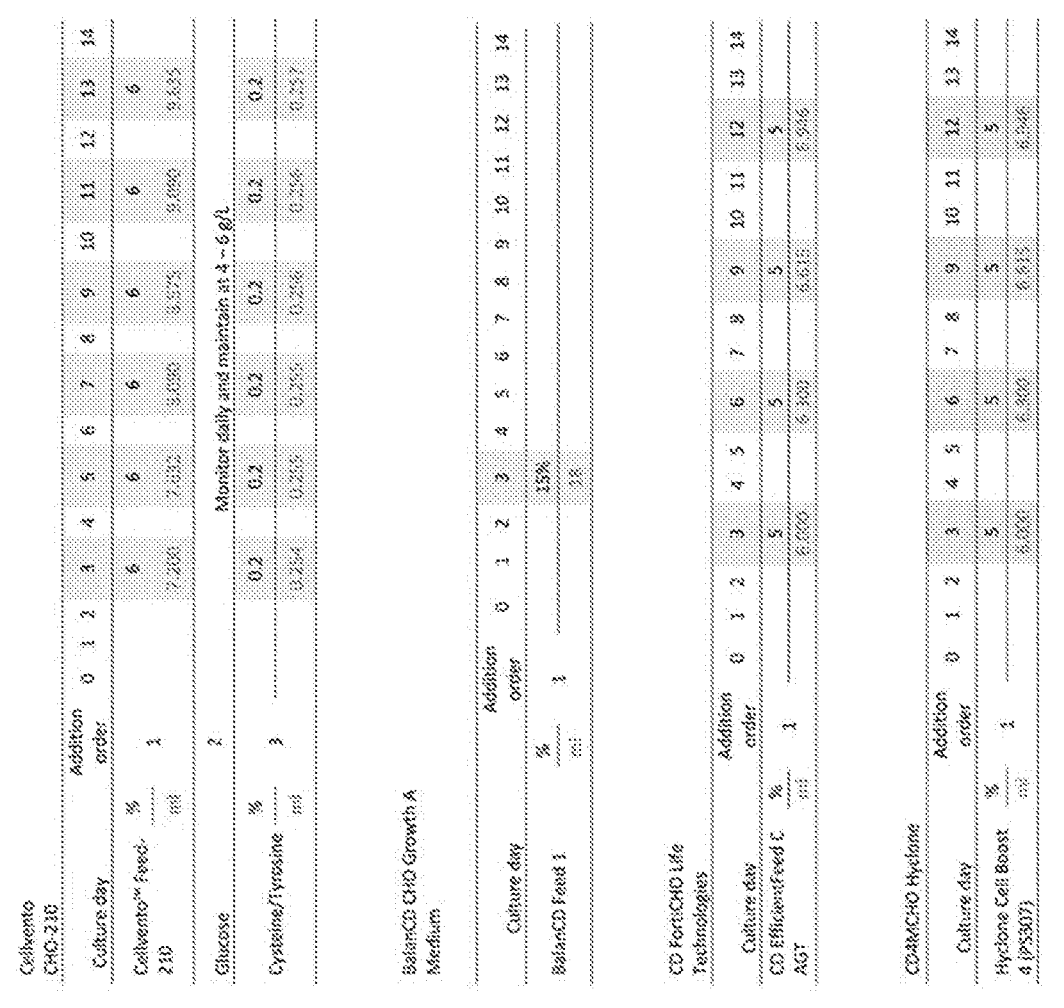

GL-2045 clone 58 was cultured in "ProCHO5" media (Lonza #12-766Q) with L-Glutamine (Lonza #17-605E) and Sodium hypoxanthine and Thymidine (HT, Gibco #11067-030) in a shaker incubator at 37 C and 5% $CO_2$. After passaging, cells were washed and inoculated at $0.5 \times 10^6$ cells/ml, then sub-cultured when densities reach $1 \times 10^6$ to 3×10⁶ cells/mL and ≥80% viability. GL-2045 clone 58 was adapted directly into selected media detailed in Table 10. Adaptation was considered complete when cells attained a stable doubling time (20-30 hours) and a viable cell density (VCD)≥90% over at least 2-3 passages. Cells were seeded at 0.5×10⁶ cells/mL into selected media (d0) and incubated in a standard shaking platform in an incubator set at 150 rpm at 37 C, 5% $CO_2$, and high humidity. For all culture except PowerCHO3 CD, feeding began on Day 3 (d3). Feeding for PowerCHO3 CD media began at d1. Total culture volume was 120 mL. Cultures were harvested when viability fell to 50%. GL-2045 stable cell line was grown in each of 7 media along with the manufacturer recommended feed according to the recommended protocol. The feeding strategy and schedule for each of the tested media is outlined in FIG. 13A and FIG. 13B.

Measurements of cell density, cell viability, and GL-2045 protein titer were performed throughout the study. For protein titer, samples were centrifuged to pellet cells and measurement of protein in cell supernatant was performed by biolayer interferometry (Octet) of the cell supernatant as described in Example 6. GL-2045 multimerization was assessed at termination of each arm of the study after protein A purification as described in Example 5. Cultures were continued until day 14 or until viability dropped below 50%.

Figure 14:
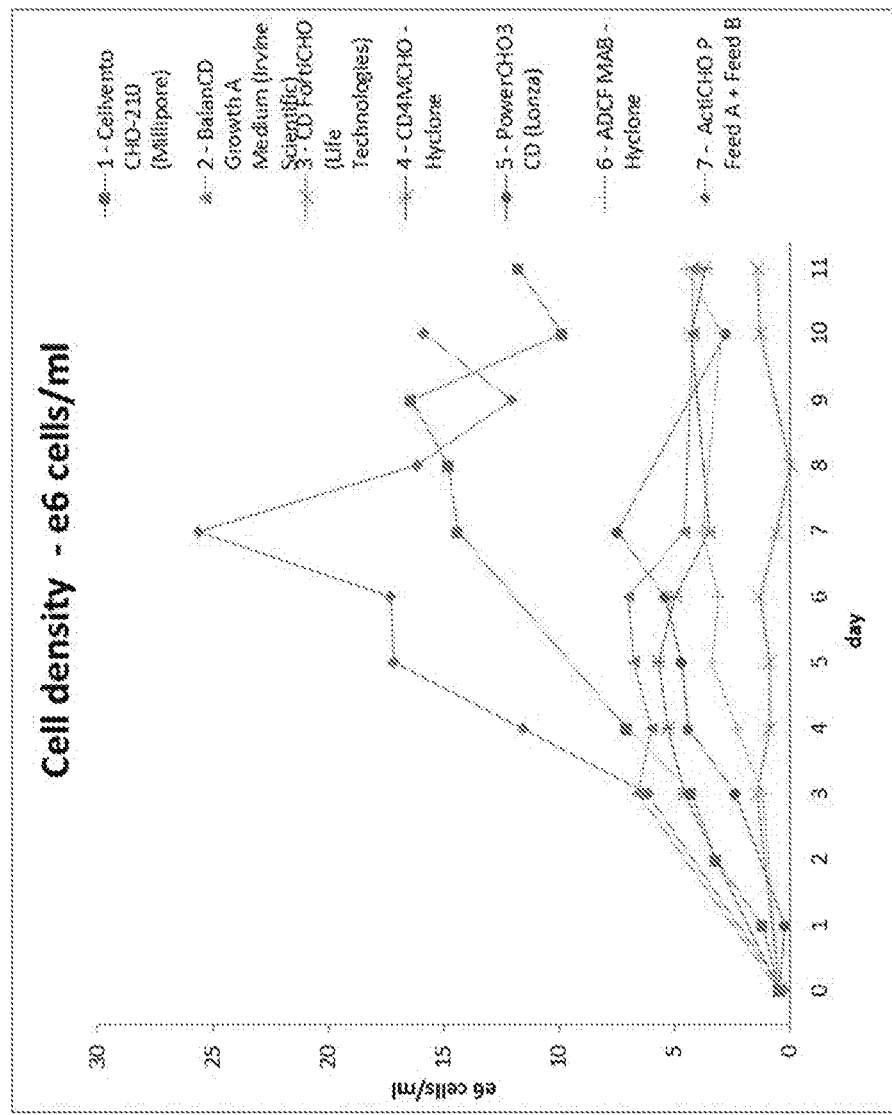
FIG. 14 illustrates cell density ($e^6$ cells/mL) of CHO cells grown in a panel of different media+feed combinations on days 0-11 of culture.

Surprisingly, GL-2045 grown in ActiCHO P with manufacturer-recommended feeds achieved a far higher peak cell density than GL-2045 grown in any of the other media with manufacturer-recommended feeds. This superior cell density was surprisingly 3-fold or greater compared with all other media/feed combinations tested except for Cell Vento 210 (FIG. 14).

Figure 15:
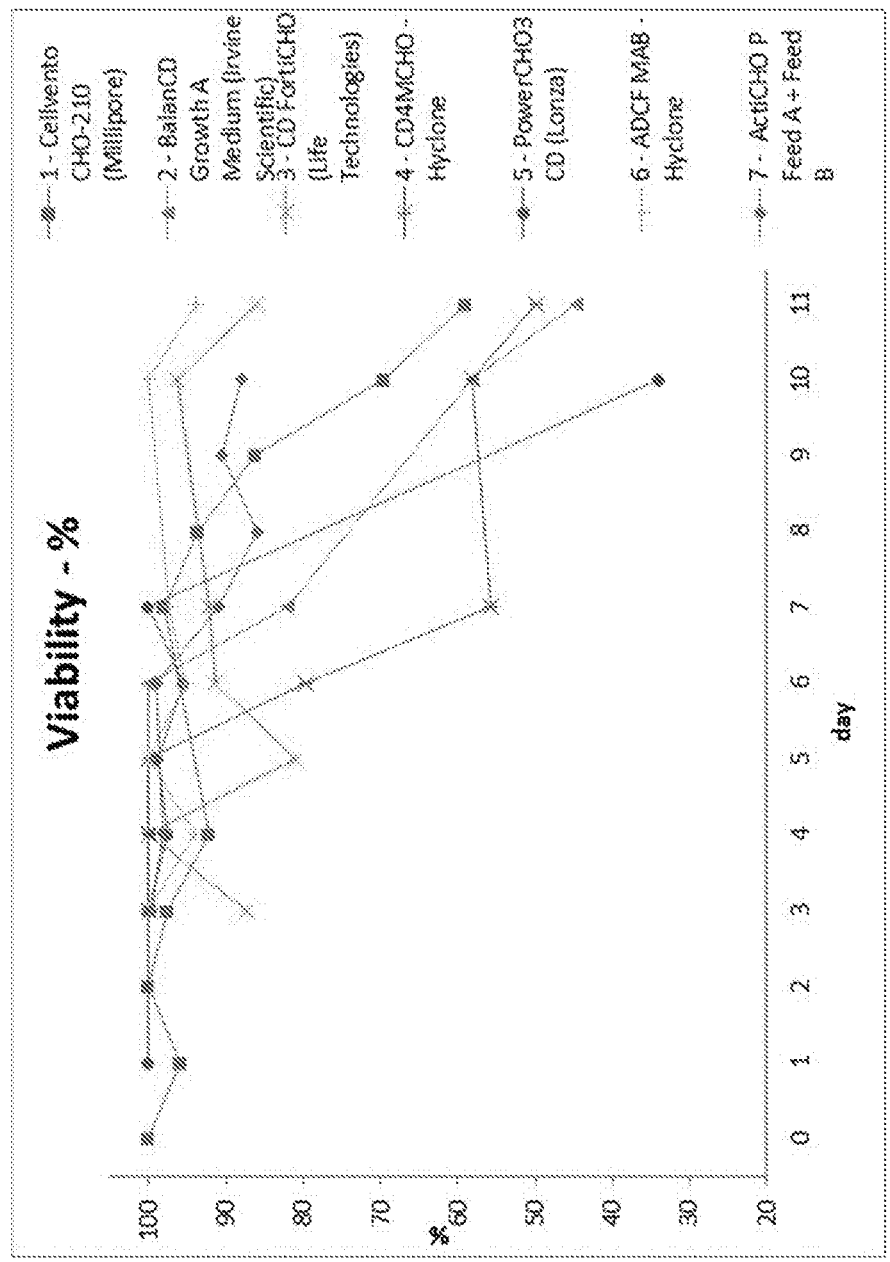
FIG. 15 illustrates cell viability (%) of CHO cells grown in a panel of different media+feed combinations on days 0-11 of culture.

Further, GL-2045 grown in ActiCHO P, CD FortiCHO, or ADCF MAB with manufacturer-recommended feeds achieved far better (2-3 fold) cell viability at day 10 than GL-2045 grown in the other media tested with manufacturer-recommended feeds. This demonstrates that these three media result in superior cell viability compared with several other media/feed combinations tested (FIG. 15).

Figure 16:
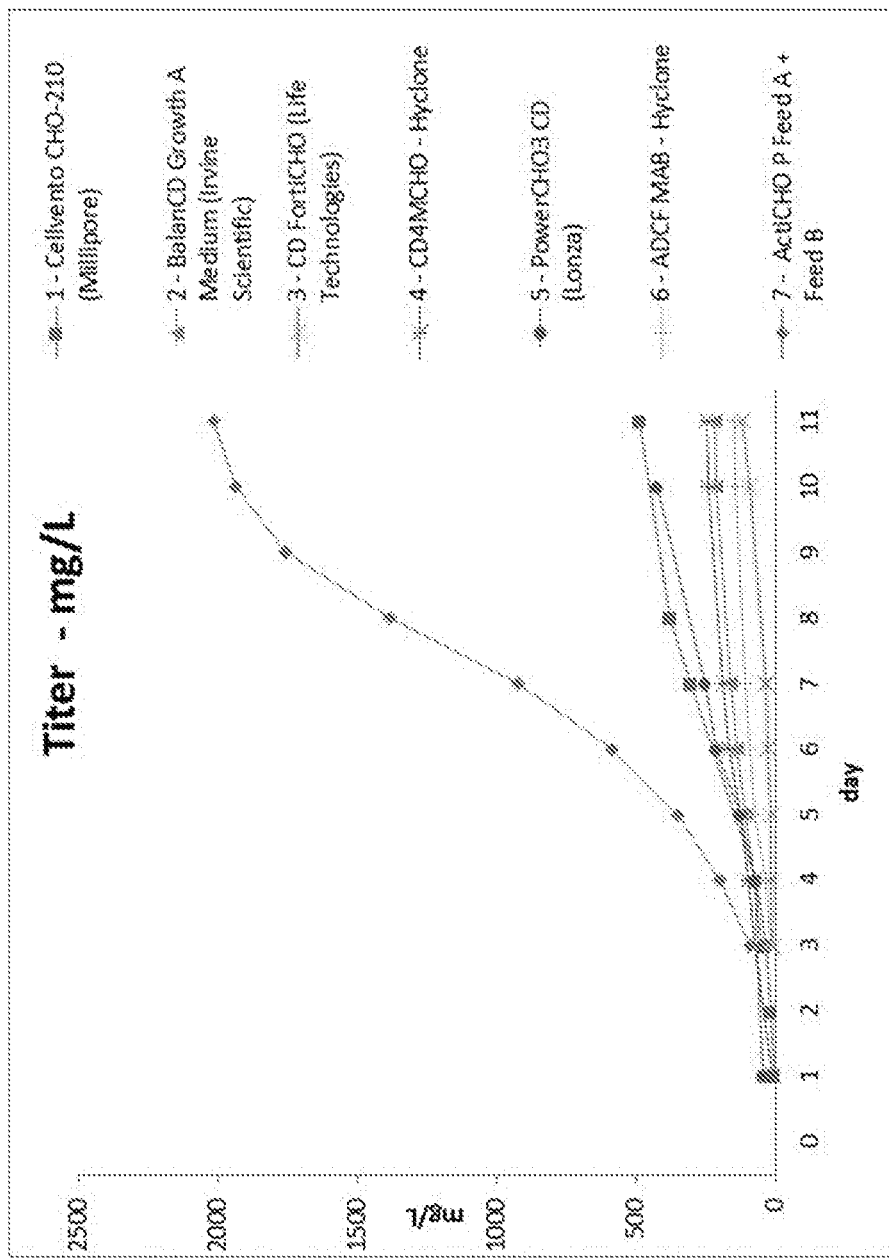
FIG. 16 illustrates protein titer (mg/mL) of GL-2045 from CHO cells grown in a panel of different media+feed combinations on days 0-11 of culture.

Additionally, the GL-2045 CHO stable cell line grown in ActiCHO P media with manufacturer recommended ActiCHO Feed A and ActiCHO Feed B generated substantially higher titers than any other media and manufacturer recommended feed tested (FIG. 16). The titer produced from the ActiCHO P culture was at least 4 fold higher than from any of the other media tested, reaching 2 g/L at day 10 in shake flask compared to less than 500 mg/L for Cell Vento CHO-210—at day 12 and even less for other media.

Figure 17:
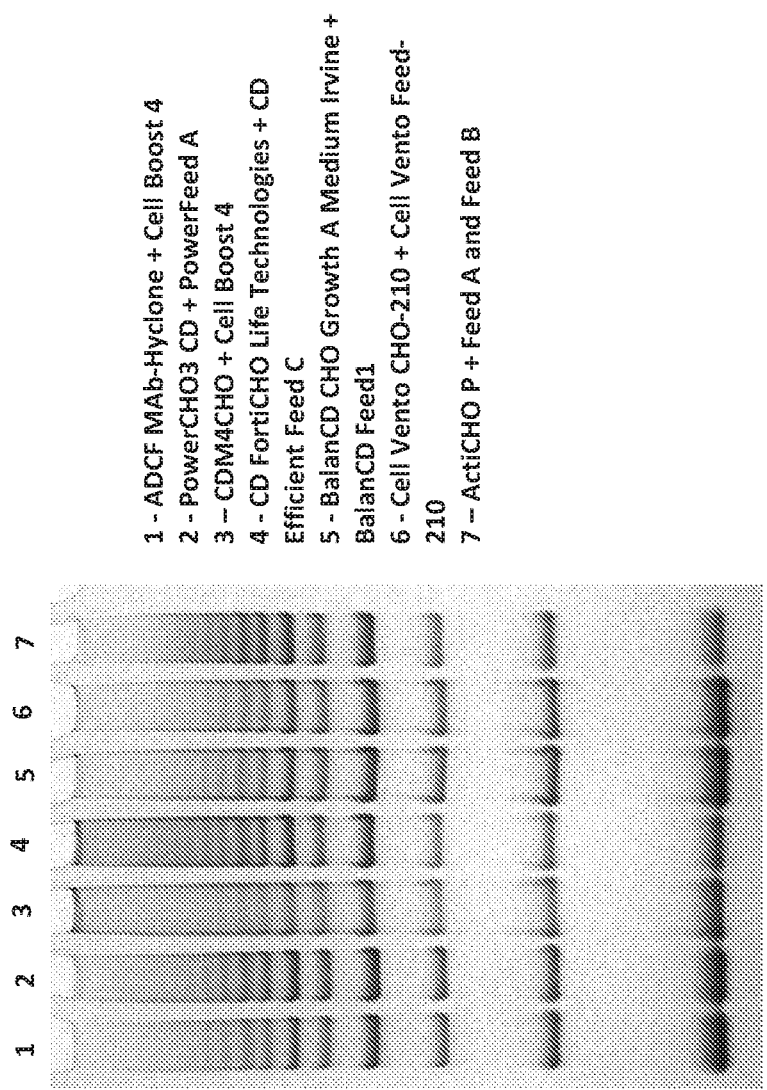
FIG. 17 illustrates SDS-PAGE analysis of the effects of the media+feed combinations and schedules illustrated in FIG. 13A-13B on GL-2045 multimerization.

Multimerization of GL-2045 as measured by percent multimer in bands 5 and above (5+) from the different culture conditions was determined as described in Example 5 (FIG. 17, Table 10). The highest rate of GL-2045 multimerization using manufacturer-recommended base media and feeds was CD FortiCHO followed by ActiCHO and PowerCHO3. ADCF-Mab and BalanCD demonstrated significantly worse GL-2045 multimerization compared with other culture conditions.

TABLE 10

Percent multimeters with Media + Feed combinations

| Media + Feed | % Bands 1-4 | % Bands 5+ |
|---|---|---|
| (1) ADCF-Mab + Cell Boost 4 Feed | 76.2% | 23.8% |
| (2) PowerCHO3 CD + PowerFeed A | 70.3% | 29.7% |
| (3) CDM4CHO + Cell Boost 4 Feed | 74.8% | 25.2% |
| (4) CD FortiCHO + CD Efficient Feed C | 64.3% | 35.7% |

TABLE 10-continued

Percent multimeters with Media + Feed combinations

| Media + Feed | % Bands 1-4 | % Bands 5+ |
|---|---|---|
| (5) BalanCD CHO Growth A + BalanCD CHO Feed1 | 76.1% | 23.9% |
| (6) Cell Vento CHO-210 + Cell Vento Feed-210 | 72.2% | 27.8% |
| (7) ActiCHO P + Feed A, Feed B | 69.9% | 30.1% |

In summary, ActiCHO P media is significantly better than the other media tested in regards to cell density, viability and protein titer. Densitometry analysis indicates that the CD FortiCHO medium+CD Efficient Feed C has the highest percent of most active multimers (Table 10, band 5+) at 35.7%. However, the CD FortiCHO medium+CD Efficient Feed C has the highest percent of high molecular weight material that does not move into the gel at 4.7% (as seen at the top of the gel in FIG. 17), suggesting that this media also generates a greater fraction of aggregated, un-ordered multimers with fewer highly ordered and more functional multimers than ActiCHO P. ActiCHO P plus feed A and B has the second highest percent of higher order multimer bands above band 4 at 30.1% with a negligible amount of non-specifically aggregated high molecular weight material that does not move into the gel. Thus, ActiCHO P likely has the highest percent of fully functional higher order multimer bands. These data further indicate, surprisingly, that upstream manufacturing conditions not only affect the cell viability, density, and total protein titer, but also the production of clinically efficacious higher order multimers of GL-2045. As demonstrated in Example 3, the highest molecular weight fractions exhibited decreased binding to FcRγIIIa, suggesting that the highest molecular weight fractions (e.g., unordered GL-2045 aggregates) are less biologically active than highly-ordered multimer of GL-2045. As shown herein, very surprisingly, of all the basal media tested, only ActiCHO-P demonstrated high total GL-2045 protein titer, high multimerization, as well as minimal amounts of unordered, high molecular weight GL-2045 aggregates.

Altered Feeding Protocols

Figure 18A:
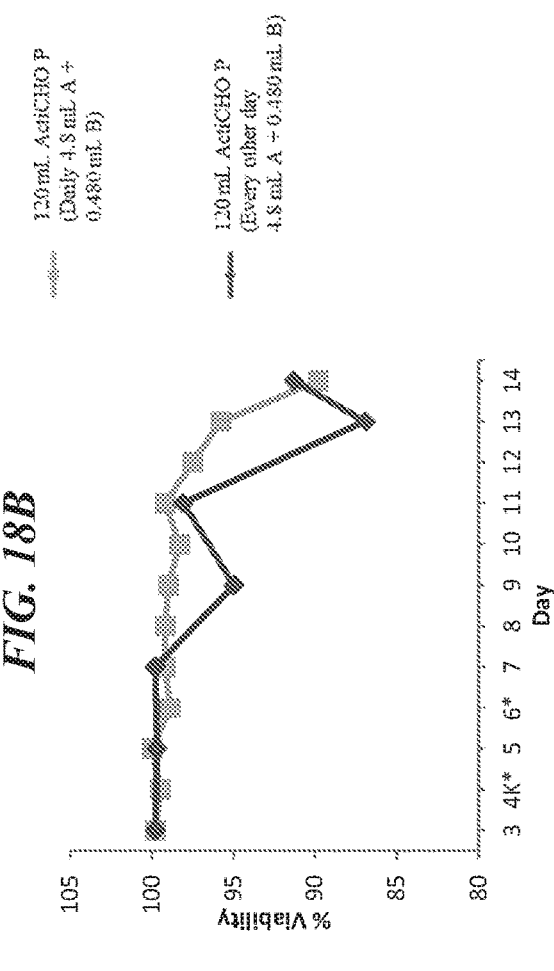
FIG. 18A-FIG. 18D illustrate the effects of ActiCHO-P media+feeding everyday (Red), and ActiCHO-P media+feeding every other day (Blue) on cell density (FIG. 18A), cell viability (FIG. 18B), culture pH (FIG. 18C), and GL-2045 protein titer (FIG. 18D).
Figure 18C:
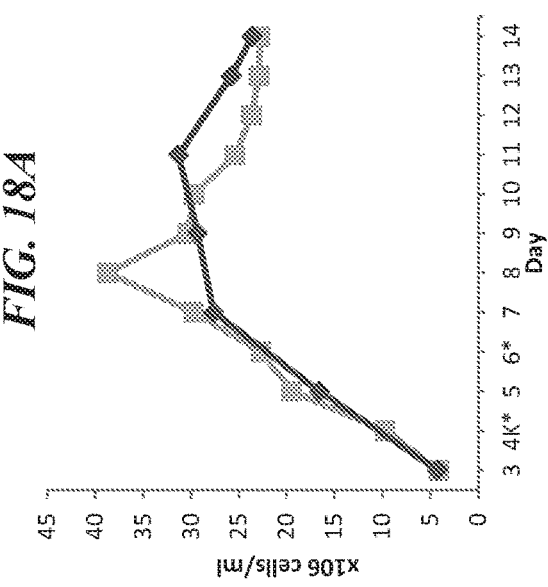
Figure 18B:
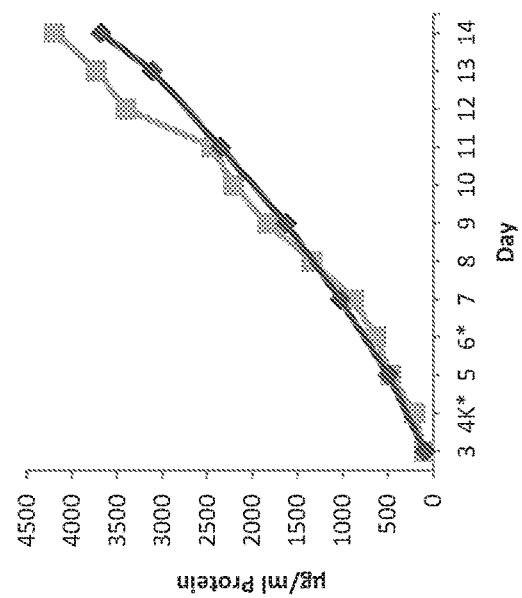
Figure 18D:
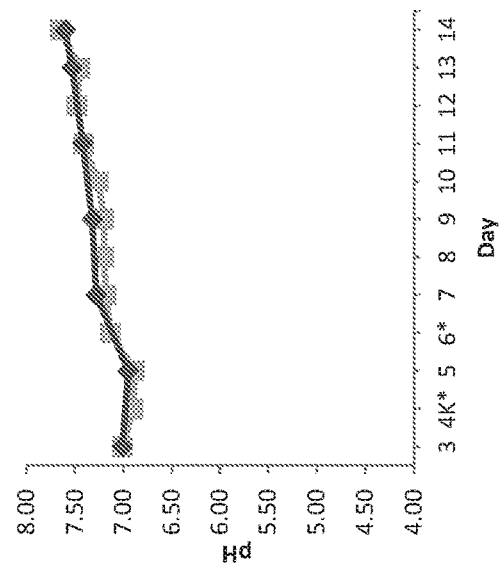
Figure 19:
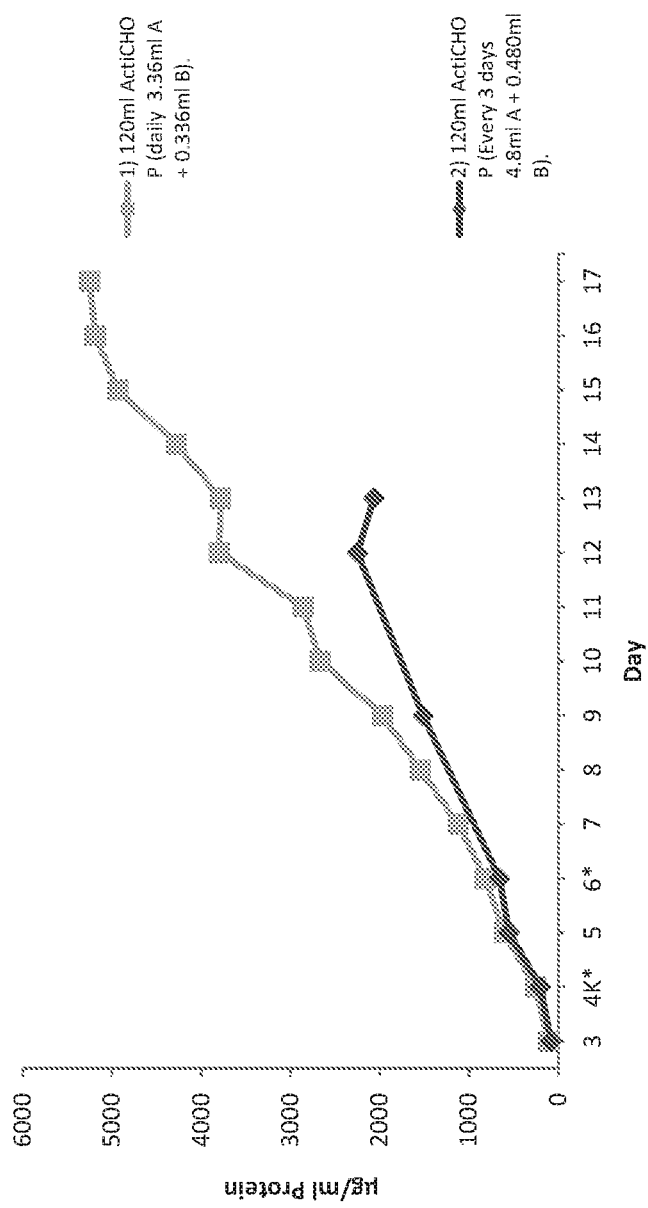
FIG. 19 illustrates the effect of ActiCHO-P media+feeding everyday (Red) and ActiCHO-P media+feeding every 3 days (Blue) on GL-2045 protein titers.

After determining that ActiCHO P media+feed resulted in optimal protein titer and production of higher order multimers, altered feeding schedules were tested to determine whether one could attain similar or optimized results by feeding every other day. As demonstrated in FIG. 18, feeding every other day (blue) did not markedly effect cell density (FIG. 18A), cell viability (FIG. 18B), culture pH (FIG. 18C), or protein titer (FIG. 18D) as compared to feeding every day. These results surprisingly indicate that similar results can be obtained with feeding every other day, and may be preferable for maintaining sterility and minimizing manufacturing costs. However, similar experiments feeding every third day suggested that viability and protein production may start to decrease with feeding less frequently than every 2 days (FIG. 19).

Figure 20B:
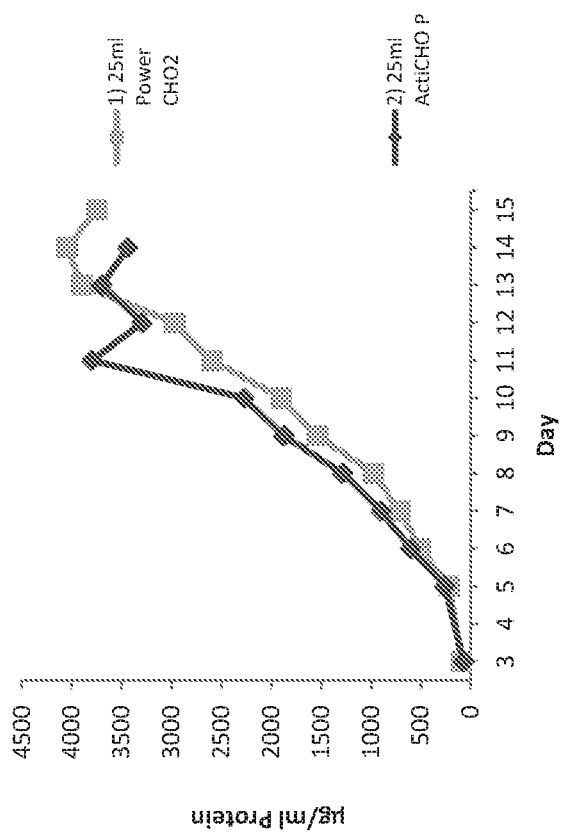
FIG. 20A-FIG. 20B illustrate the effects of combining ActiCHO Feed A with PowerCHO2 (Red) base media on cell viability (FIG. 20A) and GL-2045 protein titer (FIG. 20B) compared to using ActiCHO Feed A with ActiCHO-P base media (Blue).
Figure 20A:
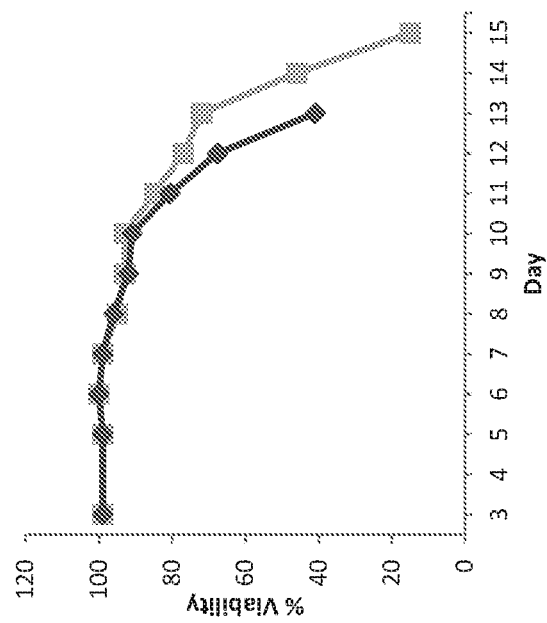

Additional experiments were performed to determine if ActiCHO P Feeds could be used with other non-ActiCHO basal media to achieve similar results. Briefly, GL-2045 clone 58 was cultured in Power CHO-2 CD (Lonza, #12-771Q)+4 mM L-Glutamine (Lonza, #17-605E)+1×HT Supplement (Gibco, #11067-030). After passaging, the cells were washed and inoculated at 0.3×10⁶ cells/ml in ActiCHO P complete media ActiCHO P+6 mM L-Glutamine (Lonza, #17-605E) or Power CHO-2 CD complete media and cultured without temperature shift. ActiCHO P PowerCHO cultures were fed every day with +1 mL ActiCHO Feed-A (PAA, #U15-072)+0.1 mL Feed-B (PAA, #U05-034). On day 9, cell viability and protein titer were determined as described in Example 5 throughout the culture (FIG. 20). The results show that, when used with ActiCHO Feeds A and B pursuant to the manufacturer's recommendation, both PowerCHO2 and ActiCHO P generate the same cell viability and GL-2045 protein yield. Thus, if multimer composition remains unchanged relative to ActiCHO P+A+B, ActiCHO Feeds A and B may be able to be used with other select high-performing base media.

Example 7—Optimal Timing and Extent of Temperature Shift for GL-2045 Production

The purpose of this experiment was to assess the optimal timing and extent of temperature shift. Numerous investigators have considered the effects of temperature shift on the cell cycle, apoptosis, and metabolism of a recombinant Chinese hamster ovary (CHO) cell line. However, while consideration is generally given to the effect of temperature shift on the viable cell density, little if any attention has been paid to the required minimal cell density for optimal temperature shift results. Further, the minimal cell density is necessary for successfully conducting a temperature shift in multimerizing stradomers has not been considered.

The present investigators surprisingly found that for optimal GL-2045 expression and maximum titer, a minimum viable cell density of 10 million cells/mL at the time of temperature shift is required. Further, this requirement is more important than the day of culture at which the temperature shift takes place. The timing of the temperature shift is surprisingly most successful when viable cell density is in a logarithmic growth phase, generally when the viable cell density is 10-15 million cells/mL. This generally corresponds to day 4-5 of bioreactor culture depending on initial seeding density.

Furthermore, in a departure from what is described in the art, a temperature shift from 37 degrees centigrade (37° C.)+/−1. ° C. to 32.5 C+/−1. ° C. is preferable to a temperature shift to 31° C.+/−0.5 C for optimal upstream conditions for manufacturing high-titers of GL-2045. Two separate pools of GL-2045 supernatant were generated from stable CHO clones using identical conditions except for the nature of the temperature shift. CHO cells were cultured in a 10 L XDR-10 Single-Use Bioreactor System bioreactor (Xcellerex, GE) with a pH shift from 7.1 to 7.0 at day 5. ActiCHO-P CD (cat #U21-051) 7 liters was used for production along with 280 ml daily of PAA Feed A (cat #U15-053) and 28 ml daily of PAA Feed B (cat #U15-054). PAA Feed A and B are equivalent to ActiCHO Feed A and Feed B. Temperature shift to 32.5 degrees (A) and temperature shift to 31.0 degrees (B) each occurred on day 5. Results are shown in Table 11.

TABLE 11

Effects of temperature shift on CHO cell viability and GL-2045 yield

| Group | pA-purified yield | Day 21 viability | Day 22 viability | Peak cell density |
|---|---|---|---|---|
| A | 7.2 g/L | 90.2% | 88.8% | $25.0 \times 10^6$ cells/mL (day 9) |
| B | 5.1 g/L | 86.1% | 83.8% | $19.3 \times 10^6$ cells/mL (day 9) |

Figure 22:
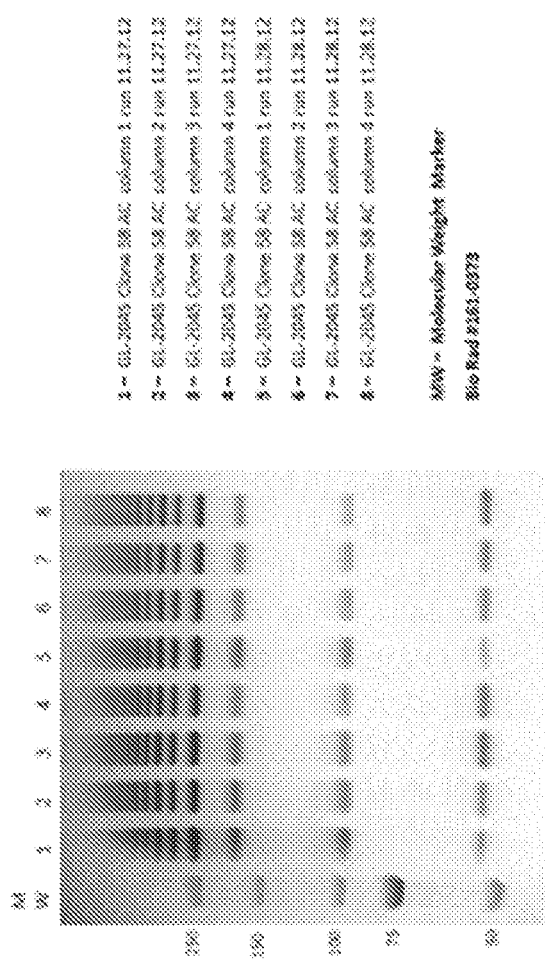
FIG. 22 illustrates SDS-PAGE analysis of protein A purified GL-2045.

Example 8—Protein a Column Purification of GL-2045 Requires More Frequent CIP Procedures GL-2045 was purified with by affinity chromatography (AC) with a protein A HiTrap MabSelect SuRe column (GE #11-0034-95) with a binding buffer of 20 mM sodium phosphate, 0.15 M NaCl, pH 7.2 and was eluted with 0.1 M glycine, pH 2.7. AC-purified GL-2045 was stored in 1×PBS, pH 7.0 (Quality Biological, Inc. #119-069-101). AC GL-2045 purifications were processed without column Cleaning In Place (CIP) procedures at the end of each run. CIP procedures typically involve flowing diluted sodium hydroxide (0.1-0.5 M NaOH) through the column between purification cycles to hydrolyze deposits while sanitizing the protein A resin, thus regenerating the binding capacity of the protein A column (Boulet-Audet et al, Scientific Reports, Vol. 6, 2016). GL-2045 was purified on 4 separate protein A affinity columns (columns 1-4, run 11.27.12). The same protein A affinity columns were then used for a second affinity purification run (run 11.28.12) after eluting the column with 100% elution buffer. Purification of GL2045 twice using the same column showed reduced amount of the lower molecular weight species, both the homodimer and the dimer of the homodimer, after a second purification run (FIG. 22). As shown in Table 12, densitometry analysis of SDS-PAGE demonstrated significant loss of homodimer and dimer bands, indicating that the lower molecular weight bands are outcompeted in binding to the protein A affinity columns by residual, highly protein A-avid, GL-2045 protein that is not completely removed from the protein A column by elution with elution buffer.

TABLE 12

Densitometry of protein A-purified GL-2045

| Homodimer Band 1 | Run 11.27.12 | Run 11.28.12 | % Difference Run ½ |
|---|---|---|---|
| Column 1 | 14.1 | 8.8 | −37.6 |
| Column 2 | 16.5 | 16.8 | 1.8 |
| Column 3 | 21.8 | 18.5 | −15.1 |
| Column 4 | 22.2 | 21.3 | −4.1 |
| | | Average | −13.8 |

| Dimer Band 2 | Run 11.27.12 | Run 11.28.12 | Percent Difference Run ½ |
|---|---|---|---|
| Column 1 | 24.9 | 19.8 | −20.4 |
| Column 2 | 17.5 | 15.3 | −12.6 |
| Column 3 | 17.1 | 14.5 | −15.2 |
| Column 4 | 15.5 | 11.7 | −24.5 |
| | | Average | −18.2 |

Loss of lower molecular weight bands indicates that there is an avidity-based binding to the affinity column whereby high molecular weight multimeric GL-2045 with multiple protein A binding sites outcompetes the low molecular weight species, causing a loss of the lower molecular weight species and effectively changing the composition of the drug. These data suggest that more frequent CIP procedures, and thus more frequent regeneration of the protein A column, are necessary for optimal purification of GL-2045 when using protein A columns for multiple purification runs. These results were unexpected since, as described above, regeneration typically requires the use of NaOH that would degrade the protein A columns most commonly used in the art. More frequent use of such a buffer would thus result in faster degradation of the protein A column. As such, a protein A column capable of withstanding frequent CIP procedures with a high-strength NaOH buffer, such as 0.5 M NaOH, must be used for regeneration of protein A columns used repetitively in the purification of GL-2045 in order to maintain the optimal profile of the intact GL-2045 drug.

Example 9—CIP Procedures for Regenerating Protein A for Repetitive Purification Cycles of GL-2045 Requires 0.5 M NaOH Loss of low molecular weight species in the absence of CIP procedures, as shown in Example 8, also indicates that there is high molecular weight species that remains bound to the protein A affinity column after the first column run, thus occupying the binding sites and preventing the binding of lower molecular weight species in subsequent purification runs. These data indicated that additional CIP procedures should be employed to maintain the multimer profile of protein A-purified GL-2045.

The present inventors discovered by regular, daily purification using the HiTrap MabSelect column (GE #28-4082-58) that after approximately 6-7 purification runs, the composition of the purified GL-2045 changed, marked by a subtle loss of the homodimer and dimer fractions. A skilled artisan purifying, for example, a monoclonal antibody would not expect to find a change in the composition of the purified product after 6-7 protein A purification runs. To solve this problem, CIP procedures with the manufacturer's recommended 0.1 M NaOH were performed to regenerate the binding capacity of the protein A column. These CIP procedures were performed after each purification run, which is more frequently than used in the art. Employing frequent CIP procedures resulted in some improvement, but did not resolve the problem of a loss of the lower molecule weight species. The inventors thus deduced that the avid binding of GL-2045 to protein A requires a more stringent CIP regimen than a skilled artisan would normally use in order to fully regenerate the column in order to facilitate retention of the homodimer and dimer.

However, the resins commonly used in protein A columns (e.g., MabSelect) are not NaOH resistant and would therefore quickly degrade with the use of a more stringent NaOH buffer, and such degeneration is associated with diminished purification capacity and with a change in the GL-2045 multimer composition. However, less commonly used protein A media (e.g., MabSelect SuRe (General Electric #11-0034-95)), can withstand enhanced cleaning at 0.5 NaOH. As such, the inventors used a MabSelect SuRe column with daily CIP procedures using a 0.5 M NaOH buffer. After the implementation of more frequent and more stringent CIP procedures, protein A purification of GL-2045 was accomplished on a daily basis without loss of homodimer or dimer and without change in the composition of GL-2045.

Thus, the inventors discovered that protein A column CIP of GL-2045 requires more stringent and more frequent CIP procedures than would normally be employed by a skilled artisan working with a monoclonal antibody or Fc fusion protein in order to retain the homodimer and dimer, and thus the optimal profile, of the intact GL-2045 drug.

Example 10—Protein A Column pH Elution Gradients are Used to Purify GL-2045 of Homodimer Aggregates that are not Highly Ordered Multimers pH elution gradients are commonly used with protein A columns during protein purification to optimize for total protein yield, but are not typically used to change the composition of a drug. The present inventors discovered that such pH elution gradient on a protein A column can be used to eliminate unordered aggregates of GL-2045 from the higher order multimers. GL-2045 CHO supernatant was purified by affinity chromatography (AC) with protein A HiTrap MabSelect SuRe (GE #11-0034-95) with a binding buffer of 20 mM sodium phosphate, 0.15 M NaCl pH 7.2, followed by an additional wash with the binding buffer. GL-2045 bound to the protein A was eluted by an elution buffer comprising 0% to 100% of 0.1 M glycine pH 2.7, thereby creating a pH gradient for GL-2045 elution from the protein A affinity column. Eluate fractions were collected into a 96 well plate (Greiner bio-one #780271), and neutralized at pH 7.5 by adding Tris-HCl pH 9.0 into each well. Equivalent protein amounts of each of the fractions were then run on a non-reducing SDS-PAGE gel (4-12% NuPage Bis-Tris, Invitrogen #NPO322BOX).

Figure 23B:
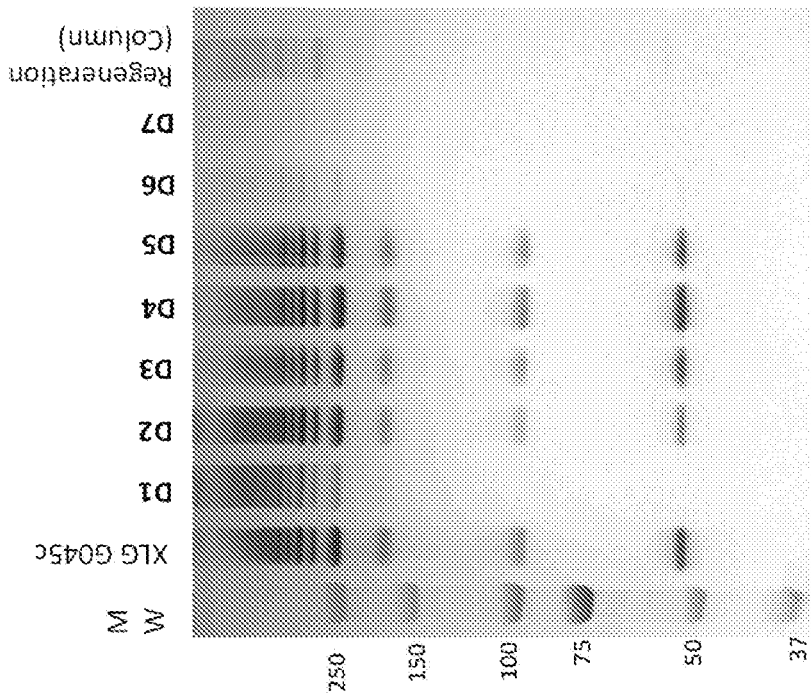
FIG. 23A-FIG. 23B illustrate an elution profile from protein A column after elution of GL-2045 by pH gradient elution (FIG. 23A) and SDS-PAGE analysis of isolated fractions (FIG. 23B).
Figure 23A:
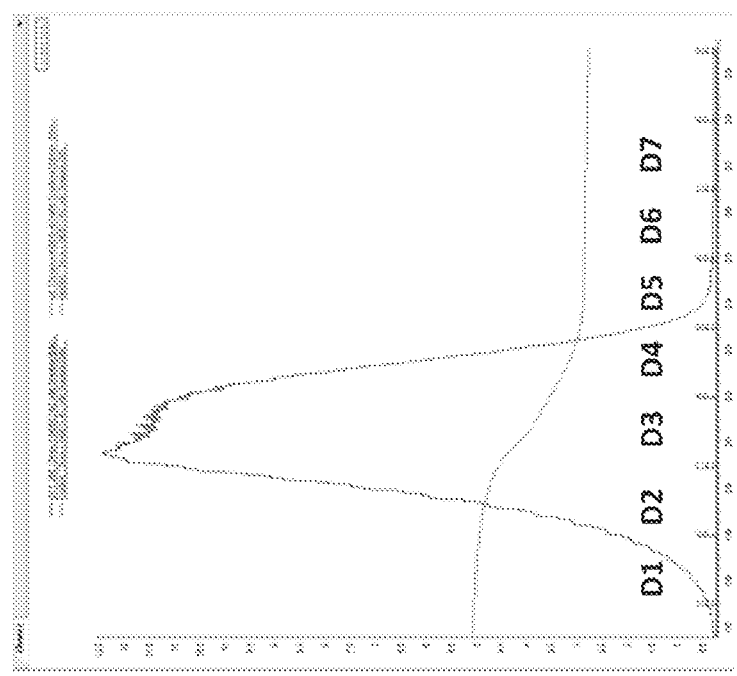

SDS-PAGE analysis of the fractions obtained by elution of the protein A column with a pH elution gradient demonstrated that very high molecular weight species were eluted last in fraction D6 and D7 (FIG. 23A and FIG. 23B). Surprisingly, the very first fraction (D1) also contained high molecular weight species. As such, these results indicate that high molecular weight fractions can be separated from the main species (e.g., homodimers, dimers and higher order multimers) of GL-2045 by pH gradient elution of protein A affinity column. As shown in Examples 1-3, these fractions may represent lower activity species demonstrated by diminished Fc receptor binding and diminished CDC inhibition.

Also shown on gel (FIG. 23B, far right lane) is a very high molecular weight fraction obtained by regeneration (CIP by 0.5M NaOH and neutralized by HCl). These results indicate that there is high molecular weight species residing on the protein A column after elution indicating again a need for high stringent NaOH buffer during CIP procedures to regenerate full column binding capacity.

Therefore, though not normally used for this purposed, pH elution gradients can be used to remove separate the high molecular weight, unordered aggregates of GL-2045 from the biologically active lower and higher order multimers. Such separation may be employed to further optimize or maintain the multimer profile of purified GL-2045. Alternatively, a step elution gradient may be used to arrive at an optimized GL-2045 composition.

Example 11—Ion Exchange Column Salt and pH Conditions Modify GL-2045 Multimer Composition An important goal for purification of GL-2045 is the tight control of the multimer composition of the final, purified product. Ion exchange columns (e.g., cation and anion exchange) are routinely used for polishing steps of purification of monoclonal antibodies and Fc fusion proteins. The present inventors tested the cation exchange medium, POROS CIEX (Invitrogen GoPure XS (10 mL) cat #4448885) with elution buffers comprising different concentrations of salt. GL-2045 was first purified by protein A affinity chromatography, and then pooled and dialyzed in 50 mM Sodium Acetate, pH 5.0 prior to loading on the CIEX column. 50 mM Sodium Acetate, pH 5, was used as equilibration and wash buffer. The effects of elution buffer (EB) salt content on GL-2045 polishing were tested with a 50 mM Sodium Acetate elution buffer with varying amounts of buffer B added (1M NaCl, pH 5, shown as % in FIG. 24). Chromatography runs were performed on AktaAvant. Briefly, the Avant method comprises equilibrating the CIEX column with 50 mM Sodium Acetate pH 5 at 2 mL/min at a total volume of 10 column volumes (cv). 65 to 100 mg of GL-2045 that was previously dialyzed in 50 mM sodium acetate, pH 5 was loaded onto the column. The column was washed with 5 cv of binding buffer at 2 mL/min. GL-2045 was then eluted with between 9 and 15 cv of buffers comprising varied percentages of NaCl (e.g. elution buffers comprised of 30-50% buffer B) at 2 mL/min.

Figure 24:
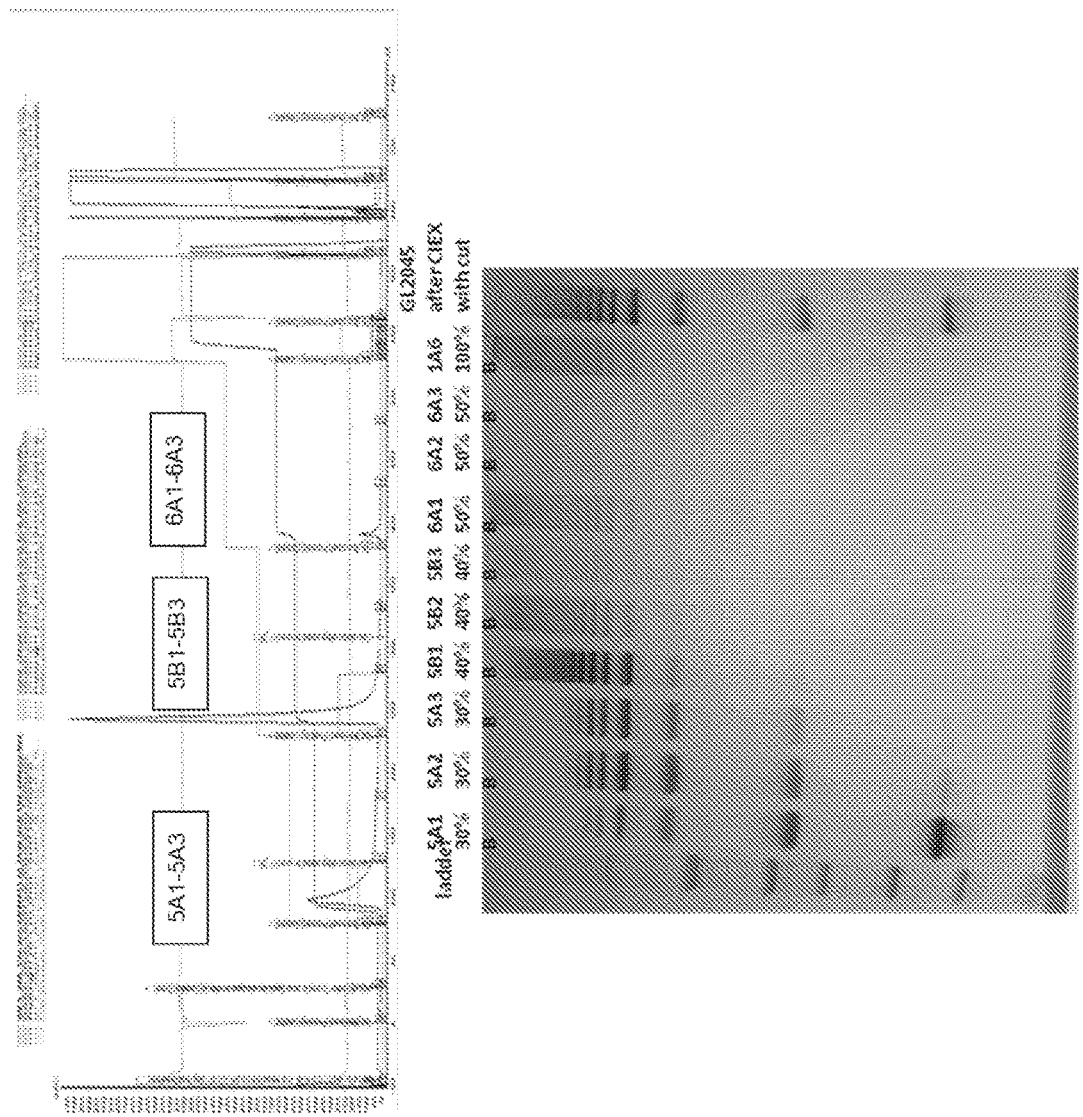
FIG. 24 illustrates an elution chromatogram and non-reducing SDS-PAGE analysis.

The % recovery of GL-2045 was determined for GL-2045 eluted with elution buffers comprising 30% buffer b, 40% buffer b and 50% buffer b (30% EB, 40% EB and 50% EB, respectively) to determine the optimal range of salt concentrations for elution buffers (FIG. 24). These data demonstrated that alterations of the salt content in the elution buffer can substantially modify the multimer composition of GL-2045.

TABLE 13

% recovery of GL-2045 eluted with elution buffers comprising 30-50% buffer b

| Elution Step | % Buffer B | Fraction | % of load |
|---|---|---|---|
| 1 | 30 | 5A1-5A3 | 37.9 |
| 2 | 40 | 5B1-5B3 | 53.8 |
| 3 | 50 | 6A1-6A3 | 3.2 |
| 4 | 100 | 1A1-1B5 | 0.6 |
| Waste | | | 4.2 |

As shown in Example 11 and quantitated in Table 13, SDS-PAGE analysis demonstrated dramatic differences in separation of GL-2045 molecular weight species when eluted with 30% EB, 40% EB, or 50% EB elution buffer. 91.7% of the material was eluted with an elution buffer comprising 30-40% buffer b, and the material recovered with an elution buffer comprising 50% buffer B was only high molecular weight material. These data demonstrate that alterations of the elution buffer can substantially modify the multimer composition of GL-2045. Thus, it is clear that the elution buffer selected for the ion exchange can be used to modify the multimer composition of GL-2045, a novel use of this technology. At the same time, the inventors have discovered that, if no change in composition of GL-2045 is desired in the ion exchange polishing step, a level of precision not normally practiced by the skilled artisan is required in selecting the salt concentration of the elution buffer for use in the ion exchange polishing steps.

Example 12—Ion Exchange Chromatography can be Used to Reduce or Eliminate Homodimer or Dimer of the Homodimer As 91.7% of the GL-2045 material in Example 11 was eluted with elution buffers comprising between 30-40% buffer b, and the material recovered with elution buffers comprising 50% buffer B was only the high molecular weight material, elution buffers with a buffer b range of 30-40% were selected for further analysis. The methods employed were similar to those described in Example 11.

Figure 25:
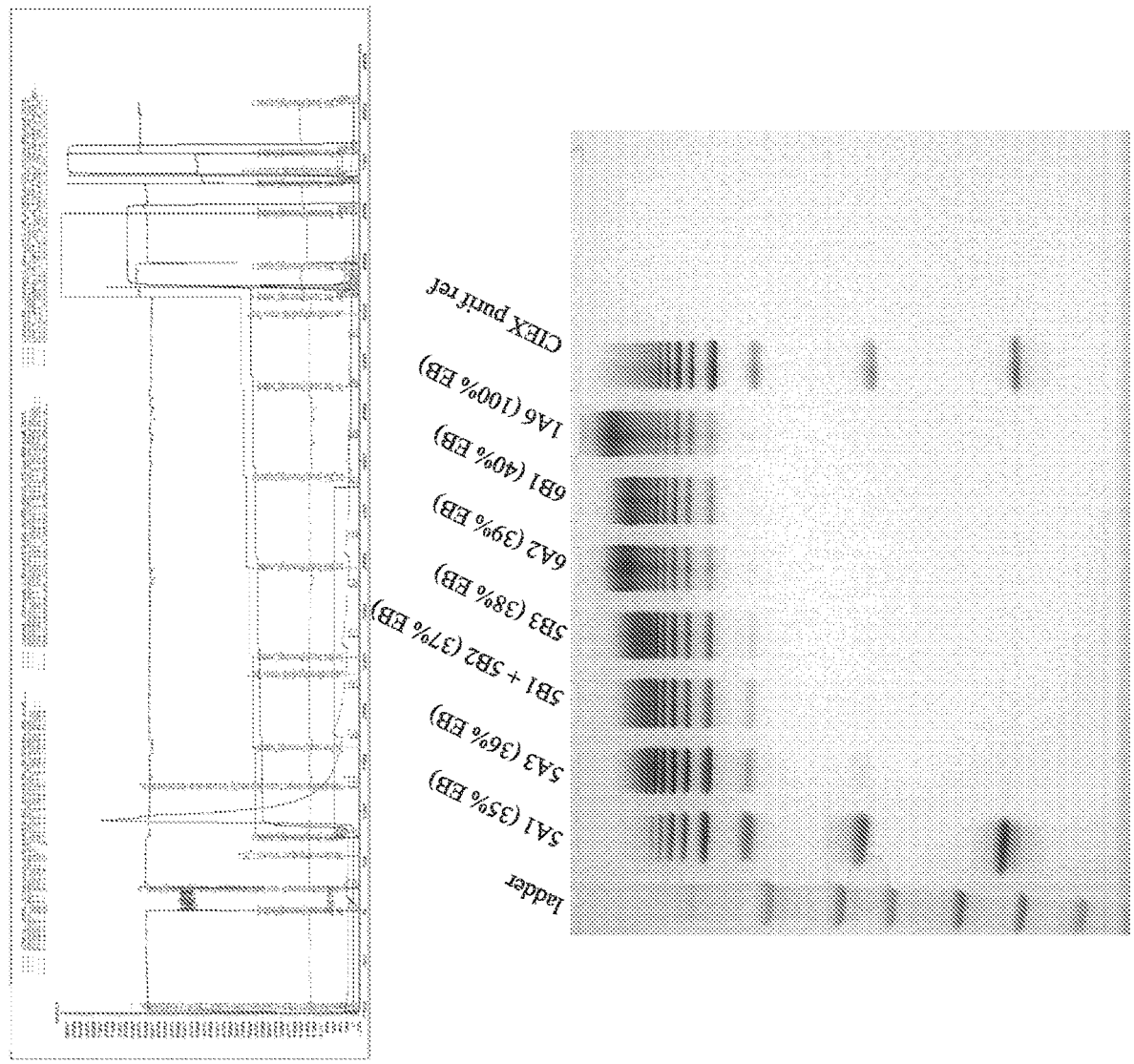
FIG. 25 illustrates an elution chromatogram and non-reducing SDS-PAGE analysis.

The SDS-PAGE analysis demonstrated dramatic differences in separation of GL-2045 homodimer when eluted with elution buffers comprising 35%, 36%, or 37% or higher of buffer b (35% EB, 36% EB, 37% EB, etc., respectively). Note that the homodimer and dimer of the homodimer that are clearly visible at 35% EB are, in contrast, greatly reduced at 36% EB and completely eliminated at 37/EB and higher (FIG. 25). Similarly, the SDS-PAGE analysis demonstrates dramatic differences in separation of the highest order multimers of GL-2045 and large unordered aggregates when eluted at 35% EB, 36% EB, or 37% EB, or when eluted with elution buffers with higher buffer b concentrations. Thus, it is clear that the elution buffer selected for the ion exchange can be used to modify the multimer profile of GL-2045, a novel use of this technology. It is also apparent that the data from this step elution can be used by a skilled artisan to select a single step or multiple step elution to obtain the desired GL-2045 profile. For example, GL-2045 polishing using a POROS CIEX column and an elution buffer comprising 36.5-38.5% buffer b will retain all homodimer, dimer, and multimers through multimer 10 and will elute off the large unordered aggregates and the highest order multimers. A similar example using a different column is shown in Example 4.

Figure 26:
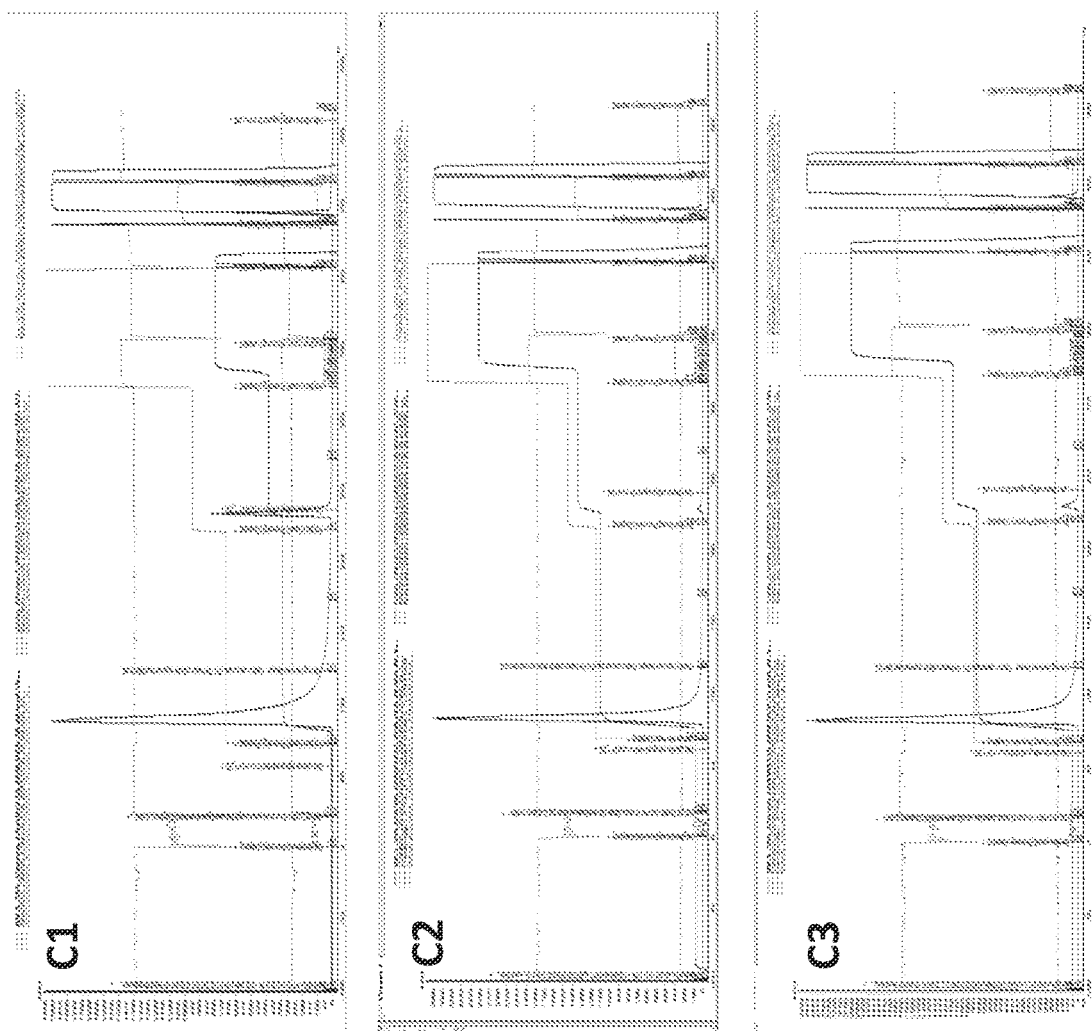
FIG. 26 illustrates an elution chromatogram of Run C1-C3.

Example 13—Ion Exchange Chromatography can be Used to Reduce or Eliminate Large Homodimer Aggregates and the Highest Order Multimers Manufacturing of optimal compositions of GL-2045 require minimizing the amount of the highest order GL-2045 multimer (e.g., bands above the clearly delineable band 10, approximately 600 kD) and eliminating material above 1000 kD to remove both large homodimer aggregates and the highest order multimers whose increased valency confers increased theoretical risk of immunogenicity. GL-2045 was eluted with elution buffers comprising different percentage of buffer b (38% EB (C1), 39% EB (C2), and 40% EB (C3)) (FIG. 26). Main elution peaks for GL-2045 were observed at 38% (C1), 39% (C2), and 40% (C3) (FIG. 26), followed by smaller elution peaks at 50% and 100% buffer B. The % of GL-2045 recovery for each elution buffer was determined and is represented in Table 14.

TABLE 14

Percent Yield of CL-2045 with varied elution buffers

| Elution Step | % Buffer B | % Yield |
|---|---|---|
| C1 Yield | | |
| 1 | 38 | 85.1 |
| 2 | 50 | 10.7 |
| 3 | 100 | 0.6 |
| Waste | | 3.5 |
| C2 Yield | | |
| 1 | 39 | 93.4 |
| 2 | 50 | 2.96 |
| 3 | 100 | 0.2 |
| Waste | | 3.6 |
| C3 Yield | | |
| 1 | 40 | 93.8 |
| 2 | 50 | 1.97 |
| 3 | 100 | 0.6 |
| Waste | | 3.5 |

Figure 27:
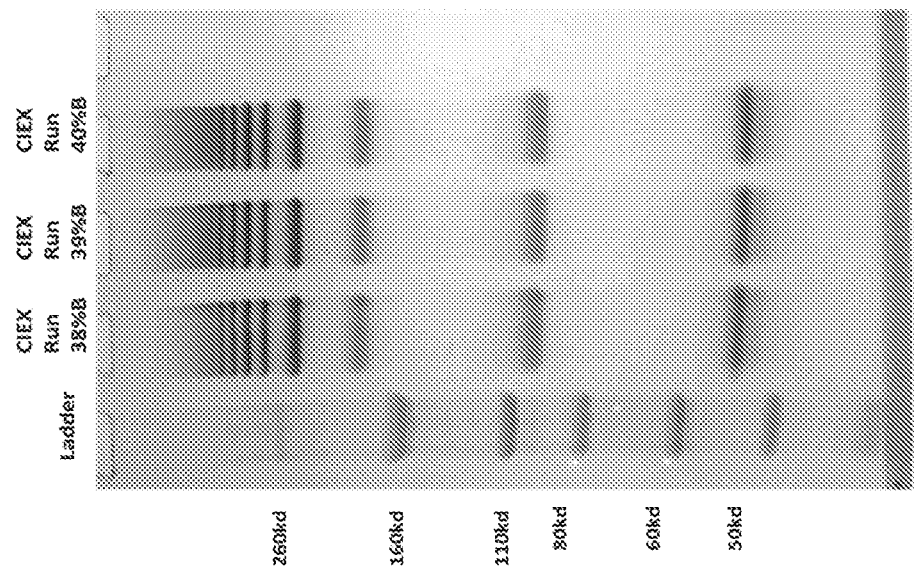
FIG. 27 illustrates non-reducing SDS-PAGE analysis of elution peaks 38%-39% from run C1-C3.

Multimer profiles of the eluted GL-2045 fractions were determined by visual inspection of SDS-PAGE analysis (FIG. 27). Visual inspection of the SDS-PAGE analysis of eluted fractions indicated that 38% of elution buffer, recovered GL-2045 with the least amount of residual high molecular weight material.

Figure 28:
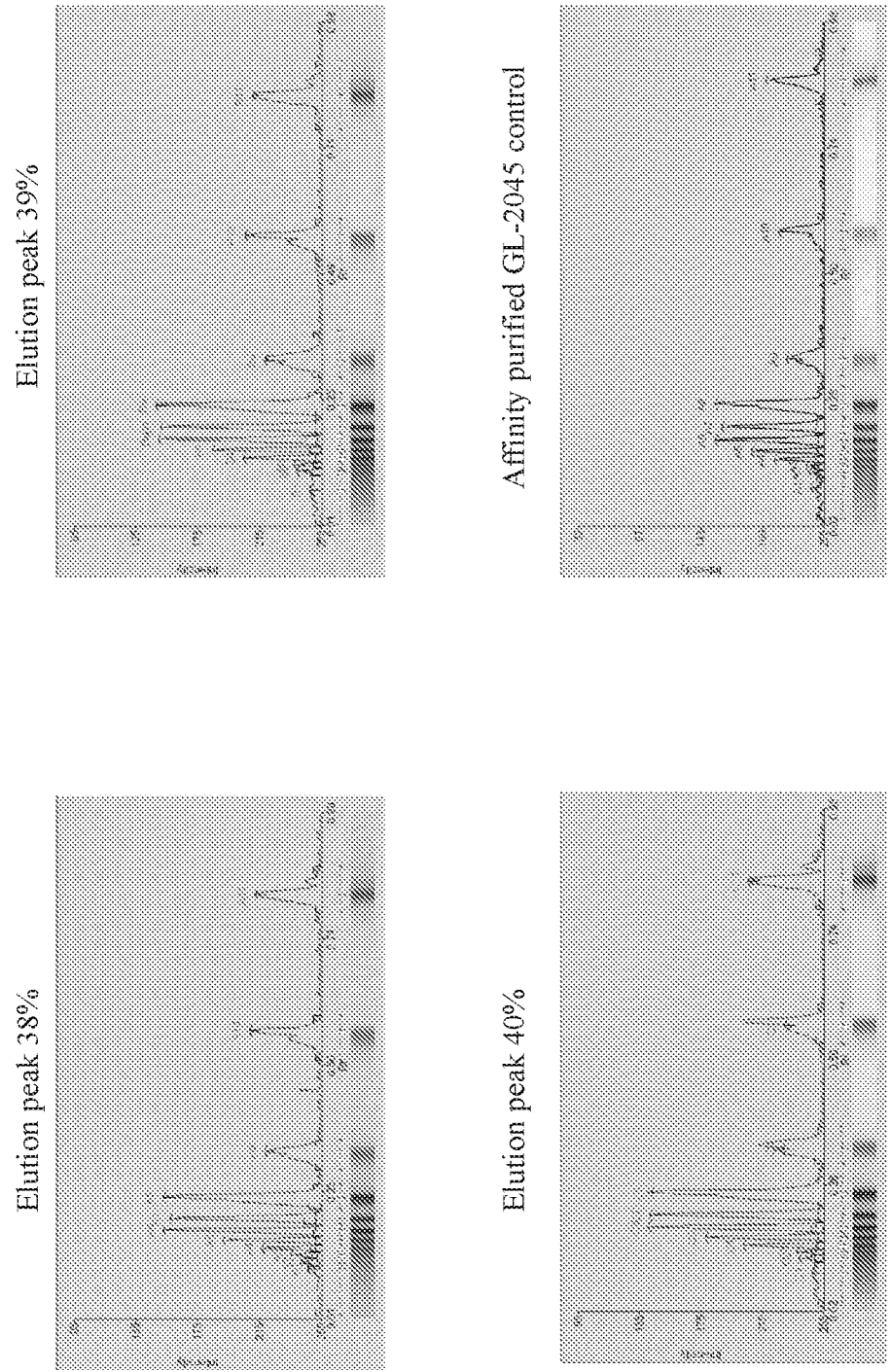
FIG. 28 illustrates densitometry analysis of ion chromatography purified GL-2045.
Figure 29A:
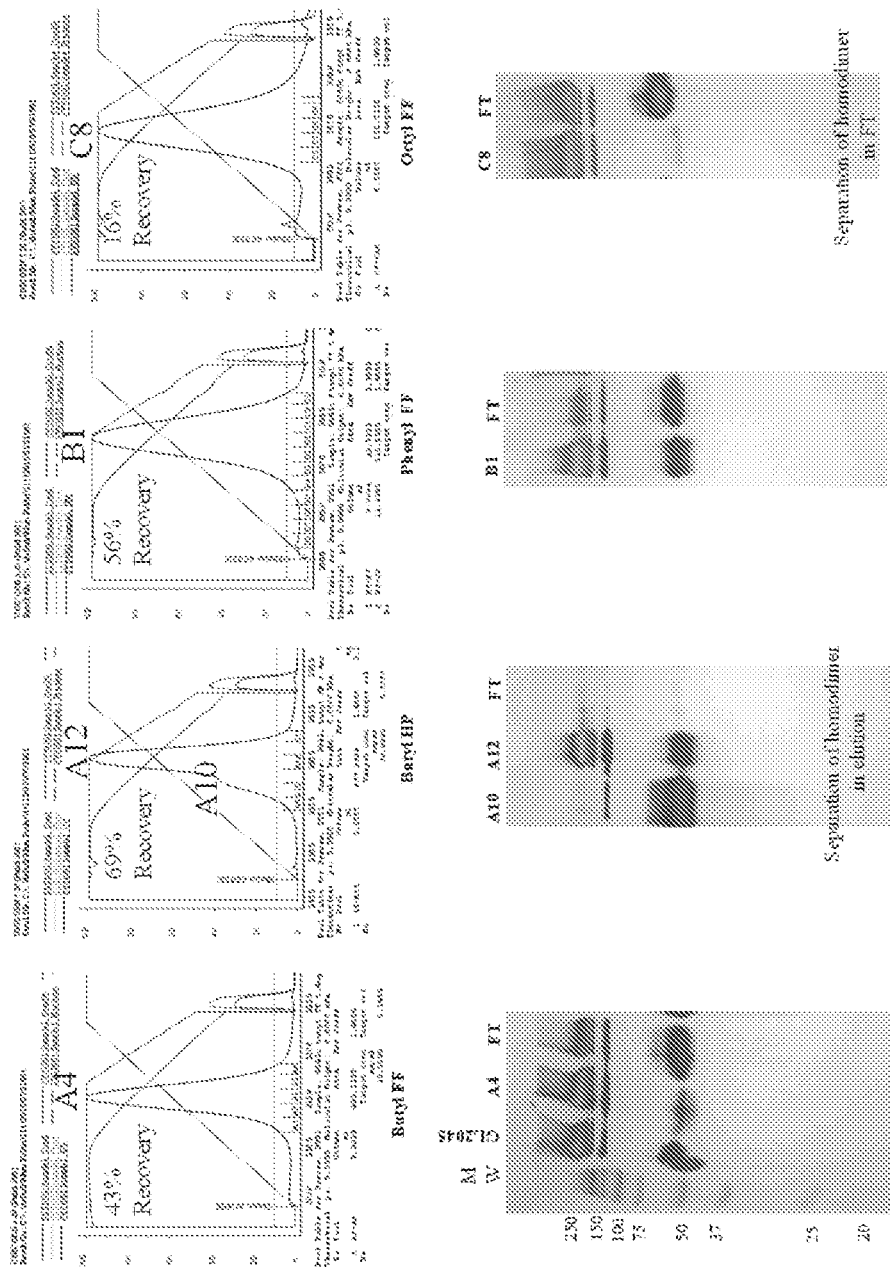
FIG. 29A-FIG. 29B illustrate elution profiles from HIC columns (upper panels) and SDS-PAGE analysis of elution and flow-through fractions (FT) (lower panels).
Figure 29B:
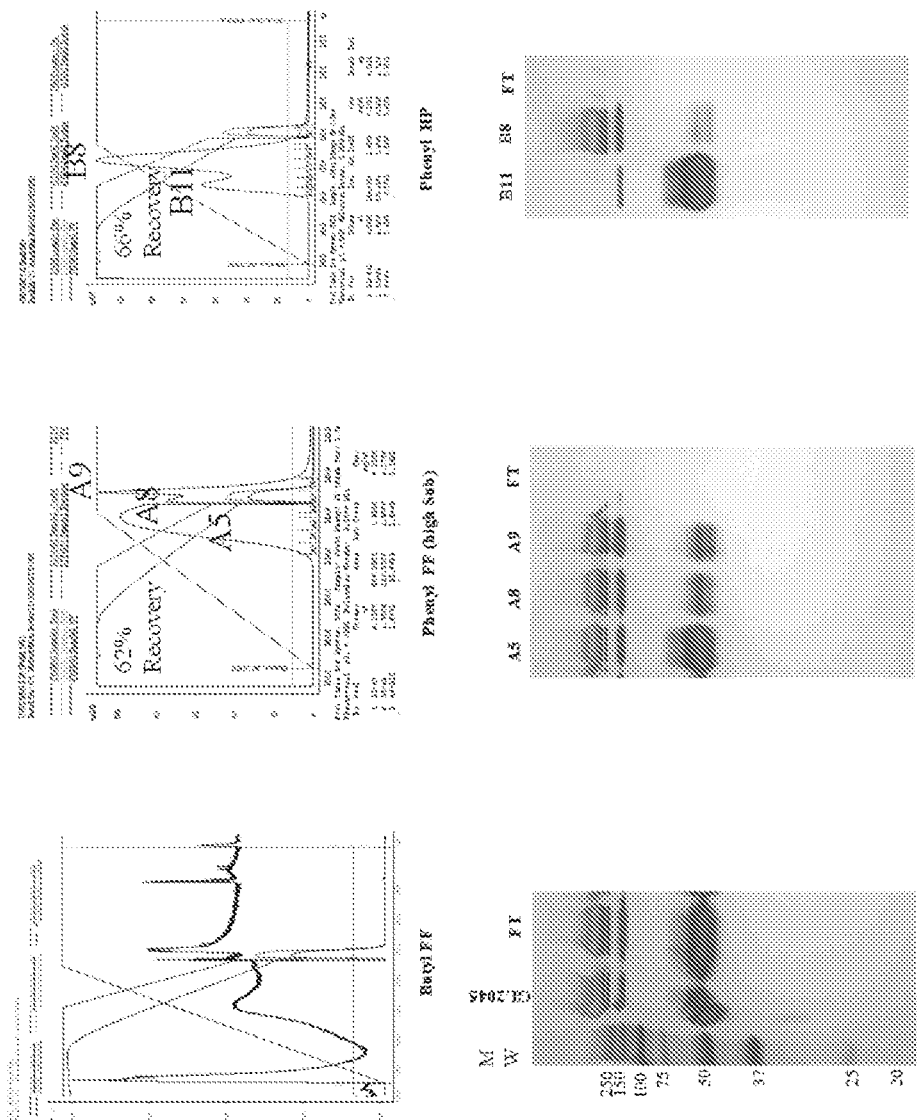

GL-2045 peaks were quantified by densitometry (FIG. 28, summarized in Table 15 as percent intensity in SDS-PAGE bands). Peak 11 represents the homodimer with the lowest molecular weight and peak 1 represents the material with the highest molecular weight material that is preferably eliminated.

TABLE 15

Summary of Densitometric Analysis

| Peak | AC/CIEX 38% (C1) | AC/CIEX 39% (C2) | AC/CIEX 40% (C3) | AC (control) |
|---|---|---|---|---|
| 1  | 2.87  | 2.64  | 2.7   | 4.93  |
| 2  | 1.73  | 0.83  | 0.62  | 0.8   |
| 3  | 1.55  | 1.11  | 0.58  | 1.09  |
| 4  | 3.34  | 3.43  | 3.39  | 3.29  |
| 5  | 5.08  | 4.9   | 5.34  | 5.16  |
| 6  | 10.04 | 9.55  | 10.05 | 9.86  |
| 7  | 11.27 | 11.1  | 11.55 | 10.13 |
| 8  | 20.22 | 19.52 | 20.89 | 17.35 |
| 9  | 10.12 | 12.1  | 11.6  | 9.2   |
| 10 | 11.47 | 12.4  | 11.43 | 9.29  |
| 11 | 13.68 | 16.36 | 14.75 | 14.67 |

These results demonstrate that a step elution protocol with an acetate elution buffer comprising 38% or 39% buffer B at pH 5 yielded approximately 85% of the preferred fractions of GL-2045 and reduced the higher molecular weight fraction above 600 kD. Although visual inspection of SDS-PAGE indicated that the high molecular weight material was lowest in the fraction eluted an elution buffer comprising 38% buffer b, densitometric analysis indicated the lowest percentage of the highest molecular weight fraction was obtained with an elution buffer comprising 39% buffer b. However, densitometric analysis demonstrated that all of the CIEX purified protein compositions contained smaller amounts in high molecular weight fraction (band 1), compared to material purified by affinity chromatography alone. Overall, analysis of the eluate suggests that the amount of large aggregates and highest order multimers can be controlled by applying controlled elution conditions with the Poros CIEX column. Thus, it is clear that the elution buffer selected for the ion exchange can be used to modify the large aggregate and largest highly ordered multimer composition of GL-2045, a novel use of this technology. A similar example using a different column is in Example 4.

Example 14—Modification of GL-2045 Multimer Composition with Hydrophobic Interaction Chromatography Columns GL-2045 was produced from a stable HEK 293F cell line and was grown in 293 Freestyle Media (Gibco #12338-018) with Glutamax (Gibco #35050-061) and Geneticin (Gibco #10131-027). Supernatants were harvested twice a week and were filtrated at 0.2 µm into 1 L filter system, (Corning #431098). GL-2045 supernatant was then purified with protein A HiTrap MabSelect SuRe (GE #11-0034-95) with a binding buffer of 20 mM sodium phosphate, 0.15M NaCl, pH 7.2 and eluted with 0.1 M sodium citrate elution buffer with a pH of 3.0-3.6. AC-purified GL-2045 was stored in 1×PBS, pH 7.0 (Quality Biological, Inc. #119-069-101).

GL-2045 was then purified on 7 different Hydrophobic Interaction Columns (HIC) using HiTrap HIC Selection Kit (GE #28-4110-07). Columns included in this kit are described in Table 16.

TABLE 16

Hydrophobic Interaction Columns

| | Columns | CV |
|---|---|---|
| 1 | HiTrap Octyl FE | 1 mL |
| 2 | HiTrap Butyl HP | 1 mL |
| 3 | HiTrap Phenyl FF (low Sub) | 1 mL |
| 4 | HiTrap Butyl FF | 1 mL |
| 5 | HiTrap Butyl-S FF | 1 mL |
| 6 | HiTrap Phenyl FF (high Sub) | 1 mL |
| 7 | Hi Trap Phenyl FF | 1 mL |

HIC columns were equilibrated with 50 mM Sodium Phosphate, 1.0 M ammonium sulfate, pH 7.0 (Start Buffer) and 3.5 mg of AC-purified GL-2045 (diluted in 4 volumes of start buffer) was loaded into each column. After washing with the start buffer, a gradient elution was performed using 0% to 100% 50 mM Sodium Phosphate, pH 7.0. All fractionated peaks and flow through were tested by SDS page. The non-reduced samples were loaded into 15% Tris HCl (Bio-Rad #161-115). The staining was done using Silver Stain kit form Invitrogen #LC6100.

The seven different HIC columns demonstrated different multimer profiles of GL-2045. As an example, the butyl HP column separated the homodimer fraction (fraction A10) from the multimeric molecular weight species found in A12. The same effect was seen with the phenyl HP column (fraction B11 compared to fraction B5). Only 16% of loaded material was recovered in the elution fractions with the Octyl FF column, indicating that it may be well suited for a flow-through mode polishing method for GL-2045. Further, the eluted fractions from the Octyl FF column contained the higher molecular weight species, indicating that the column may also be well suited for removal of very high molecular weight homodimer aggregate species that have lower potency.

Figure 30:
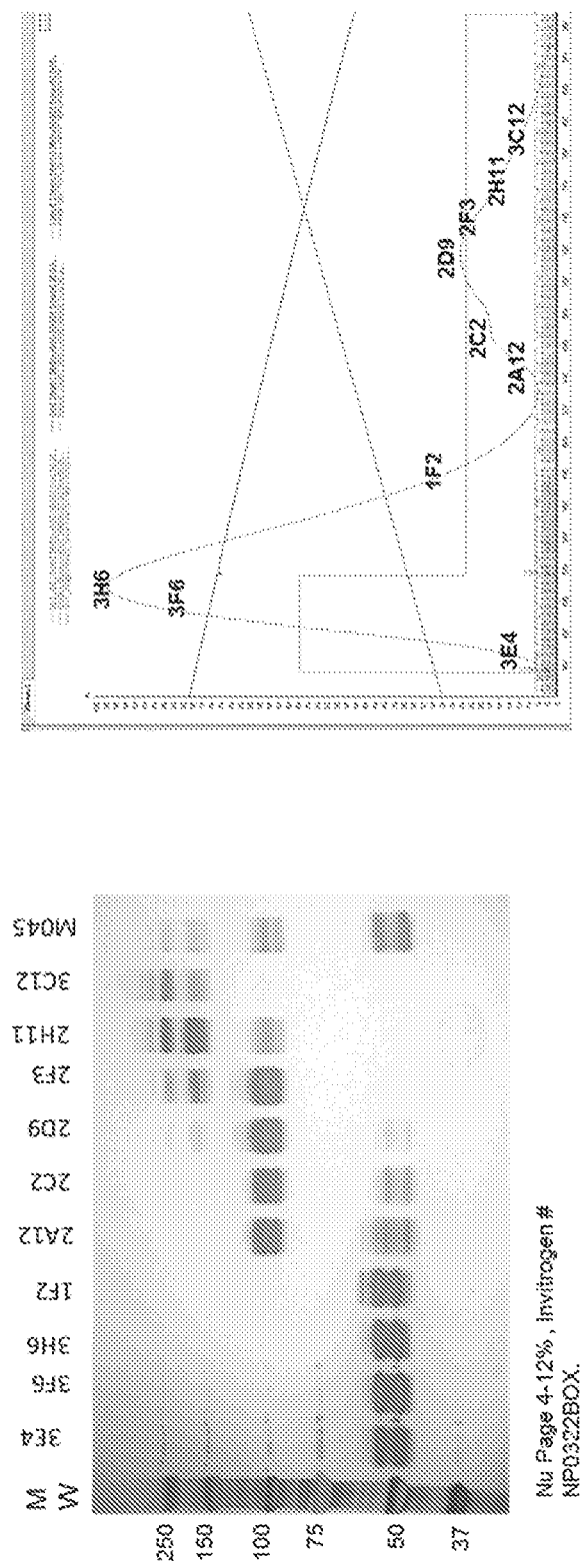
FIG. 30 illustrates an elution profile from HIC column polishing of M045 (right panel) and Nu-PAGE analysis (right panel).
Figure 31:
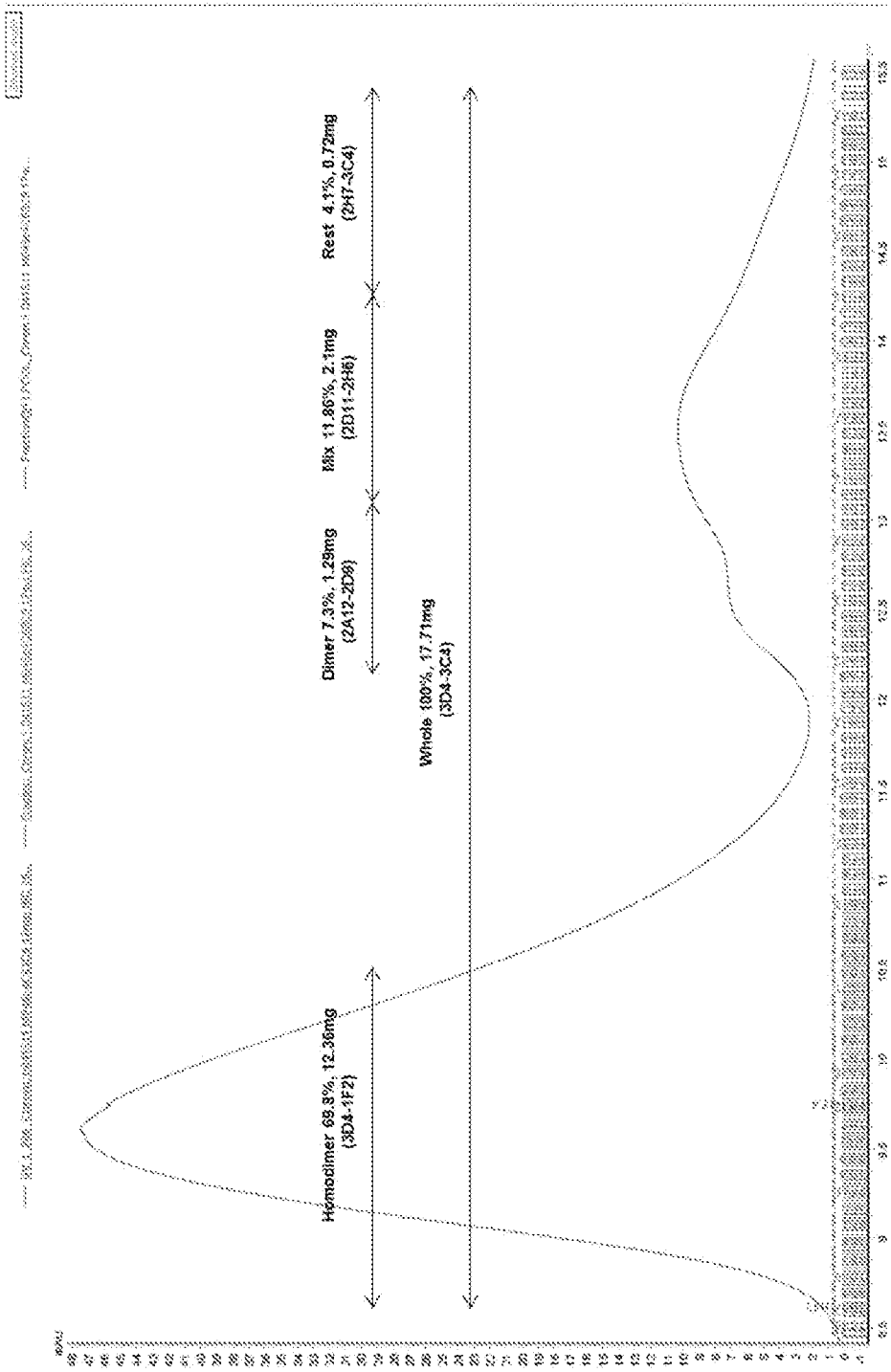
FIG. 31 illustrates an elution profile from HIC column polishing of M045.

A similar experiment was performed on the murine version of GL-2045, known as M045, M045 was purified by protein A affinity chromatography and then further purified on the AKTA Avant (GE) by HIC with Hiload 26/10 Phenyl Sepharose High Performance (GE 17-1086-01). The HIC column was equilibrated with 0.1 M sodium phosphate, 1 M ammonium sulfate pH 7.0 (Start buffer) and M045 was loaded onto the column followed by a wash step with the Start buffer to remove all unbound materials. M045 was then eluted with 0.1 M sodium phosphate pH 7.0 elution buffer with a gradient elution (FIG. 30-31).

Figure 32:
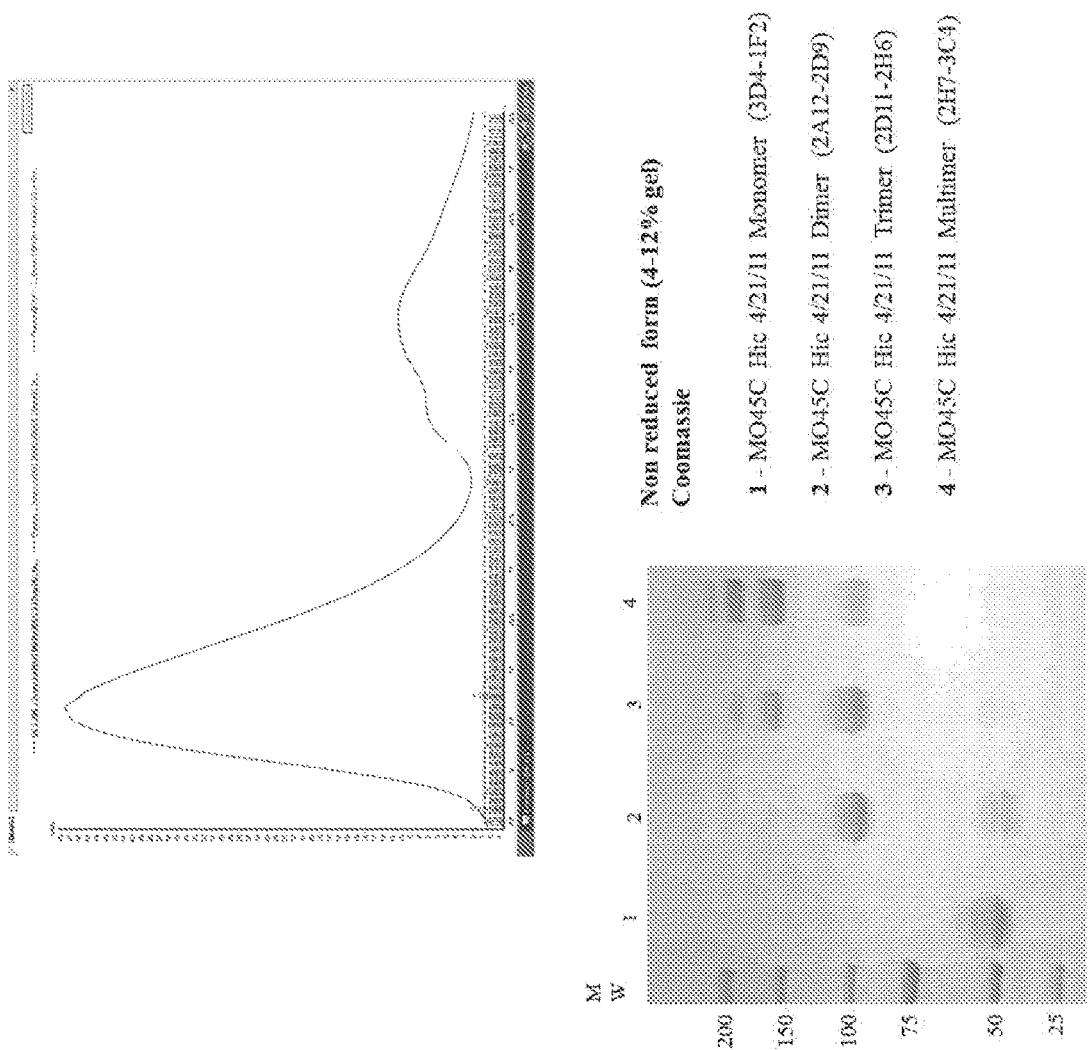
FIG. 32 illustrates an elution profile from HIC column polishing of M045 and SDS-PAGE analysis.

HIC-purified fractions of M045 were analyzed by SDS-PAGE to determine the effect of the HIC column polishing on the M045 multimer profile. These results further demonstrated that hydrophobic interaction columns can be used to modify the multimer composition of M045, noted by the clear separation of the homodimer, dimer, trimer, and multimer fractions (FIG. 32).

Example 15—Exemplary Protocol for Optimally Produced GL-2045

The data described herein demonstrate the optimal conditions for several variables of the upstream and downstream manufacturing process for GL-2045 that result in optimization of (1) protein titer, (2) cell viability throughout culture, and (3) multimerization of GL-2045 and (4) maintenance of the multimer profile in the final GL-2045 drug substance. Importantly, the level of multimerization of GL-2045 is critical to the clinical efficacy of the stradomer (See Examples 1-4). Current culture methods are not necessarily aimed at the optimized production of a specific fraction or enhancement of a particular multimerization pattern. As such, the upstream culture reagents and conditions and the downstream purification media and conditions that affect multimerization are all unknown and cannot be predicted based on the current state of the art.

The data described herein resulted in the discovery of the following protocol elements for generating optimally manufactured GL-2045:

(1) The Optimal Based Media for Generating Optimally Manufactured GL-2045 is ActiCHO P.

Data described herein demonstrate that the optimal base media was ActiCHO P. CHO cells cultured in a bioreactor in ActiCHO P base media resulted in a high cell density and cell viability, while optimizing for an increase in protein titer compared to other base media tested. Surprisingly, ActiCHO P media resulted in an increase in the percentage of higher order multimers of GL-2045 present at the end of the culture protocol.

(2) The Optimal Feeds for Generating Optimally Manufactured GL-2045 is ActiCHO P are ActiCHO Feed a and Feed B.

Data described herein further demonstrate that the optimal feed was ActiCHO P Feed A and Feed B, added to the culture every day or every other day. ActiCHO P Feed A and Feed B maintained high cell density and high cell viability, while resulting in a protein titer that was 4-fold greater than other media/feed combinations tested. Importantly and unexpectedly, ActiCHO P media with Feed A and Feed B resulted in a high level of highly ordered multimers and, importantly, a reduction in the percentage of high-molecular weight, unordered aggregates of GL-2045 compared to other media/feed combinations tested. These data indicate that this particular media/feed combination results in the production of a greater percentage of GL-2045 multimers with enhanced clinical efficacy (e.g., a greater percentage of highly ordered GL-2045 multimers). The present inventors surprisingly found similar results for addition of Feed A and Feed B every other day, indicating that this particular media/feed combination can be used to reduce costs and mitigate the risk of contamination associated with daily culture manipulation.

Further, ActiCHO P media with Feed A and Feed B resulted in the production of a substantial percentage of GL-2045 existing as higher-order multimers, while minimizing the percentage of un-ordered, high molecular weight aggregates of GL-2045. As such, this particular media/feed combination surprisingly optimized specifically for the biologically functional and clinically efficacious fractions of highly ordered multimerized GL-2045, therefore optimizing retention of the GL-2045 multimer profile while reducing the need to eliminate high order aggregates in further downstream purification steps.

(3) The Optimal Temperature Shift for Generating Optimally Manufactured GL-2045 is a Shift from 37° C. to 32.5° C. Based on Cell Density.

Data described herein additionally demonstrate that a temperature shift from 37° C. to 32.5° C. based on cell density results in optimal cell density, viability, and protein titer. This temperature shift protocol is a deviation from established protocols (Ouguchi et al, Cytotechnology, 52(3), pp. 199-207, (2006); Masterson and Smales, Pharmaceutical Bioprocessing, 2(1), pp. 49-61, (2014)), which describe a temperature shift from 37° C. to 31° C. based simply on day of culture. The present inventors unexpectedly found shifting the temperature to 32.5° C. after the cells had reached a density of ~10-15×$10^6$ cells/mL resulted in not only the maintenance of a high cell density and cell viability, but also in a substantial increase in protein titer compared to previously established protocols.

Data demonstrated herein indicate that specific downstream purification protocols result in GL-2045 compositions with an optimized multimerization profile. In carrying out these purification methods, strict attention must be paid to maintaining the desired multimer profile of GL-2045 by controlling column conditions and buffers. This stands in stark contrast to a monoclonal antibody, Fc fusion protein, or similar CHO-derived protein where purity and retention of yield are the primary goals.

(4) Optimized Protein a Purification of GL-2045 Requires Frequent and Stringent CIP Methods GL-2045 avidly binds protein A. This avid binding resulted in GL-2045 remaining bound to the protein A media in the column when CIP procedures normally employed for mAb purification were used. As a result, with repeat cycles of use of the protein A column, the homodimer fractions of GL-2045 were unable to bind to protein A and flowed through the column. This resulted in a substantial and functionally important change in the multimer profile of the final protein A-purified GL-2045 product. The avid binding of GL-2045 therefore resulted in a requirement for more frequent and more stringent (e.g., using a 0.5 M NaOH wash buffer) CIP procedures than are commonly used in the art (e.g., during mAb or Fc-fusion protein purification). These results were unexpected, as most commonly used protein A columns are unable to withstand the stringent NaOH washes required to remove GL-2045 multimers and to fully regenerate the protein A column. Therefore, only some protein A columns, especially MabSelect SuRe, are capable of being used for GL-2045 purification and will require frequent CIP procedures with approximately 0.5 M NaOH to maintain the desired GL-2045 multimer profile.

(5). A pH Elution Gradient or Step Elution Facilitates the Separation of the Highest Molecular Weight Fractions of GL-2045 from the Lower and Higher Order Multimers.

Using pH elution gradient with protein A purification resulted highest molecular weight components being eluted in the first and last elution fractions. These data indicate that a pH gradient can be utilized to separate the biologically active fractions of GL-2045 (e.g., the homodimer, dimer, and higher order multimers) from fractions comprised of the un-ordered high molecular weight aggregates, which have been previously shown to have decreased biological activity.

(6) The Optimal Elution Buffer for the Polishing of GL-2045 by Ion Exchange Chromatography is an Acetate Buffer+30-40% Buffer b. Especially 37.5%-39%+/0.5%.

Ion exchange chromatography is commonly used to polish the drug of impurites during mAb production. However, the present inventors utilized ion exchange chromatography to eliminate specific fractions of GL-2045 (e.g., the highest order multimers and high molecular weight unordered aggregates of the homodimer) such that an optimal multimerization profile was achieved. In particular, the present inventors found that an elution buffer of 30-40% buffer b decreased the amount of high molecular weight unordered aggregates of GL-2045. Even more specifically, an elution buffer of 38-39% buffer b specifically maintained the amount of the homodimer present in the final GL-2045 product, while also optimizing for reduced amounts of the unordered aggregates.

(7) Hydrophobic Interaction Columns (HIC) can be Utilized to Achieve Specific GL-2045 Multimerization Profiles.

Data herein demonstrate that multiple HICs can be used in the polishing steps of purifying GL-2045. For example, flow through from the Octyl FF column contained mainly high molecular weight species, indicating that this column can be used specifically for the removal of high molecular weight aggregates of GL-2045. Alternatively, the butyl HP columns can be used to separate the homodimer fraction from the multimeric fractions for application wherein one of the fractions may achieve more desirable outcomes. Alternatively, HIC columns can be used in binding mode.

Optimized Manufacturing Protocol for GL-2045

Taken together, incorporating all of the parameters discussed above, the following protocol resulted in the highest protein yield of GL-2045 while maintaining the highest percentage of the overall population as multimers.

CHO cells were transfected with two vectors using a proprietary transfection system by ExcellGene SA (Monthey, Switzerland), one a GL-2045 expression vector comprising a GL-2045 expression cassette flanked by piggyBac transposase targeting sequences, and the second vector comprising a piggyBac transpoase. PiggyBac transposon has preferential insertion into highly transcribed regions of the genome and additionally contains inverted terminal repeats that provide insulation from gene silencing. The transfection resulted in the integration of the expression cassette into highly transcribed genomic regions thereby establishing a bank of stably transfected CHO cells with fewer than 20 genome insertions of the transgene. The stably transfected CHO cells were then cultured in a bioreactor with ActiCHO P media at a growth temperature of 37° C. During this culture, cells were fed daily with ActiCHO Feed A and Feed B at a growth temperature of 37° C., until the cultures reach a cell density of about 10 million to about 15 million cells/mL. After such densities were reached, the growth temperature was shifted from 37° C.±1° C. to 32.5° C.±1° C., and optimally manufactured GL-2045 from culture media was harvested from the media on the final day of culture.

This protocol resulted in a cell viability of greater than 95% at day 18 of culture and greater than 80% at day 21, and a final total protein titer of greater than 9,000 mg/mL, wherein greater than 70% of GL-2045 was present as non-homodimers and greater than 30% was present as higher-order multimers above the fifth multimer.

GL-2045 was harvested from the culture supernatant with a tangential flow filtration system that does not obstruct passage of the largest highly ordered multimers, thereby retaining the homodimer and multimer profile of the supernatant. Downstream manufacturing methods were then employed to isolate GL-2045, to remove impurities, and to isolate a particular fraction in order to control the multimer profile of GL-2045 (e.g., removal of un-ordered, high molecular weight aggregates). GL-2045 was purified by protein A affinity chromatography, wherein protein A media was selected for the ability to withstand high alkalinity regeneration. Further, more than one wash buffer was used to enable further control over the purification process. Additionally, CIP procedures were performed more frequently than normally done and with a 0.5 M NaOH buffer to remove GL-2045 multimers that had avidly bound to the column in order to fully regenerate the binding capacity of the protein A column as required to retain the homodimer in the final GL-2045 composition. GL-2045 was eluted from the protein A column with or without a pH elution gradient. After purification by protein A column affinity chromatography, additional polishing steps were employed. Cation exchange chromatography was used to remove high molecular weight, unordered aggregates of GL-2045 with an elution buffer comprising 37-39%+/−0.5% buffer b, preferably with a CIEX POROS XS resin. In some embodiments, HIC columns were used to further purify GL-2045. To remove high molecular weight, unordered aggregates of GL-2045, the Octyl FF resin was used as an additional polishing step. Alternatively, the butyl HP-containing columns were used to isolate specific GL-2045 fractions (e.g., isolation of the higher order multimers). Additionally, anion exchange columns, specifically Q Sepharose Fast Flow columns were used as an additional polishing step, particularly in flow through mode.

While these additional purification steps may be used individually, it was preferable that purification of GL-2045 by protein A affinity chromatography was used in combination with all three of anion exchange, cation exchange, and hydrophobic interaction chromatography to arrive at a final GL-2045 drug substance, wherein the final protein titer is >4 g/L, of which >70% of GL-2045 is present as a multimer, wherein >30% of the multimers are pentameric multimers or higher.

Example 16—Analysis of Optimally Produced GL-2045

To further characterize the optimally produced GL-2045 made by the methods described herein, GL-2045 was produced in a bioreactor according to the upstream methods described herein using the ActiPRO basal media, feeds, temperature shifts described herein. The resulting GL-2045 supernatant was then passed through a Millipore X0HC depth filter followed by filtration through a 0.2 µm filter and processed using multiple downstream processing methods. The multimerization profile of the GL-2045 composition was assessed after each processing step and is shown in FIG. 33. The multimerization profile of the filtered GL-2045 preparation is shown by the red dots in FIG. 33. The filtered GL-2045 preparation was then subjected to affinity chromatography with protein A MabSelect Sure (GE. #11-0034-95) (multimerization profile shown by blue dots in FIG. 33), and then purified with AIEX in flow through mode using the Q Sepharose Fast Flow column. The resulting GL-2045 was then pH adjusted to pH 5.0±0.10 and filtered through a 0.2 µm filter (multimerization profile shown by green dots in FIG. 33). The GL-2045 was then purified with cation exchange chromatography using the Poros XS column in binding mode by step elution using an elution buffer comprising 50 mM NaAcetate+375 mM NaCl, pH 5.0 (multimerization profile shown by yellow dots in FIG. 33) before hydrophobic interaction chromatography (multimerization profile shown by orange dots in FIG. 33), and filtration (multimerization profile shown by purple dots in FIG. 33) to arrive at the final drug substance (multimerization profile shown by black dots FIG. 33). Raw data for FIG. 33 is shown in Table 17 below.

TABLE 17

Multimer percentages determined by analytical HPLC

| Run | Step | 7+ mer | 6 mer | 5 mer | 4 mer | 3 mer | 2 mer | Homo-dimer | Vessel |
|---|---|---|---|---|---|---|---|---|---|
| HH RegTox Run 1 | 1 MabSelect Load | 35.4 | 13.3 | 7.4 | 13.6 | 7.7 | 8.4 | 13.0 | SUB |

TABLE 17-continued

| | Multimer percentages determined by analytical HPLC | | | | | | | | |
|---|---|---|---|---|---|---|---|---|---|
| Run | Step | 7+ mer | 6 mer | 5 mer | 4 mer | 3 mer | 2 mer | Homo-dimer | Vessel |
| HH RegTox Run 1 | 2 MabSelect Pool | 35.7 | 12.7 | 7.4 | 13.9 | 7.4 | 9.6 | 13.4 | SUB |
| HH RegTox Run 1 | 3 AEX Pool | 36.4 | 12.5 | 7.2 | 13.8 | 7.3 | 9.4 | 13.1 | SUB |
| HH RegTox Run 1 | 4 CEX Pool | 32.1 | 12.3 | 7.5 | 14.4 | 7.8 | 10.6 | 15.3 | SUB |
| HH RegTox Run 1 | 5 HIC Pool | 31.7 | 12.4 | 7.4 | 13.7 | 7.4 | 10.8 | 16.6 | SUB |
| HH RegTox Run 1 | 6 UFDF Pool | 32.1 | 12.6 | 7.5 | 14.0 | 7.6 | 10.8 | 15.4 | SUB |
| HH RegTox Run 1 | 7 DS | 32.1 | 12.6 | 7.5 | 14.0 | 7.6 | 10.8 | 15.4 | SUB |
| HH RegTox Run 2 | 1 MabSelect Load | 35.8 | 13.0 | 7.3 | 13.2 | 7.7 | 8.4 | 13.6 | SUB |
| HH RegTox Run 2 | 2 MabSelect Pool | 35.2 | 12.7 | 7.5 | 13.8 | 7.5 | 9.7 | 13.7 | SUB |
| HH RegTox Run 2 | 3 AEX Pool | 35.9 | 12.5 | 7.4 | 13.7 | 7.3 | 9.5 | 13.6 | SUB |
| HH RegTox Run 2 | 4 CEX Pool | 30.8 | 12.3 | 7.7 | 14.4 | 8.1 | 10.9 | 15.8 | SUB |
| HH RegTox Run 2 | 5 HIC Pool | 30.3 | 12.4 | 7.7 | 13.9 | 7.9 | 11.0 | 16.9 | SUB |
| HH RegTox Run 2 | 6 UFDF Pool | 31.8 | 12.3 | 7.7 | 14.0 | 7.9 | 10.9 | 15.4 | SUB |
| HH RegTox Run 2 | 7 DS | 31.1 | 12.4 | 7.8 | 14.2 | 8.0 | 11.0 | 15.6 | SUB |
| HH 100L Run 1 | 1 MabSelect Load | 39.2 | 12.4 | 7.2 | 12.8 | 7.2 | 7.5 | 13.4 | SS |
| HH 100L Run 1 | 2 MabSelect Pool | 38.8 | 12.3 | 7.3 | 13.1 | 7.0 | 8.1 | 13.5 | SS |
| HH 100l Run 1 | 3 AEX Pool | 37.7 | 12.4 | 7.3 | 13.3 | 7.1 | 8.3 | 13.9 | SS |
| HH 100L Run 1 | 4 CEX Pool | 33.0 | 12.7 | 7.7 | 14.2 | 7.8 | 9.2 | 15.5 | SS |
| HH 100L Run 1 | 5 HIC Pool | 33.2 | 12.8 | 7.2 | 12.6 | 6.7 | 9.5 | 18.0 | SS |
| HH 100L Run 1 | 6 UFDF Pool | 33.9 | 12.9 | 7.5 | 12.9 | 6.8 | 9.5 | 16.6 | SS |
| HH 100L Run 1 | 7 DS | | | | | | | | SS |
| HH 100L Run 2 | 1 MabSelect Load | | | | | | | | SS |
| HH 100L Run 2 | 2 MabSelect Pool | 35.6 | 12.0 | 7.6 | 13.2 | 7.5 | 9.3 | 14.7 | SS |
| HH 100L Run 2 | 3 AEX Pool | 35.4 | 11.9 | 7.6 | 13.4 | 7.6 | 9.4 | 14.7 | SS |
| HE 100L Run 2 | 4 CEX Pool | 30.6 | 12.0 | 8.0 | 14.0 | 8.2 | 10.5 | 16.6 | SS |
| HH 100L Run 2 | 5 HIC Pool | 30.0 | 12.1 | 7.7 | 13.0 | 7.5 | 10.9 | 18.8 | SS |
| HH 100L Run 2 | 6 UFDF Pool | 30.6 | 12.3 | 7.9 | 13.2 | 7.7 | 10.9 | 17.5 | SS |
| HH 100L Run 2 | 7 DS | | | | | | | | SS |
| HR 100L Run 3 | 1 MabSelect Load | 34.5 | 12.7 | 8.0 | 13.6 | 7.6 | 9.2 | 14.4 | SS |
| HH 100L Run 3 | 2 MabSelect Pool | 36.1 | 12.4 | 7.8 | 13.2 | 7.4 | 9.2 | 13.9 | SS |
| HH 100L Run 3 | 3 AEX Pool | 36.0 | 12.4 | 7.7 | 13.3 | 7.4 | 9.3 | 14.0 | SS |
| HH 100L Run 3 | 4 CEX Pool | 29.5 | 12.3 | 8.1 | 14.2 | 8.3 | 10.8 | 16.7 | SS |
| HH 100L Run 3 | 5 HIC Pool | 29.6 | 12.3 | 7.9 | 13.2 | 7.7 | 11.0 | 18.2 | SS |
| HH 100L Run 3 | 6 UFDF Pool | 29.8 | 12.6 | 8.0 | 13.5 | 7.9 | 11.1 | 17.2 | SS |
| HH 100L Run 3 | 7 DS | | | | | | | | SS |
| HH 250L Run | 1 MabSelect Load | | | | | | | | SUB |
| HH 250L Run | 2 MabSelect Pool | 34.8 | 12.9 | 7.6 | 14.1 | 7.3 | 9.6 | 13.8 | SUB |
| HH 250L Run | 3 AEX Pool | 34.7 | 12.8 | 7.5 | 14.2 | 7.3 | 9.7 | 13.7 | SUB |

TABLE 17-continued

Multimer percentages determined by analytical HPLC

| Run | Step | 7+ mer | 6 mer | 5 mer | 4 mer | 3 mer | 2 mer | Homo-dimer | Vessel |
|---|---|---|---|---|---|---|---|---|---|
| HH 250L Run | 4 CEX Pool | 29.5 | 12.7 | 7.8 | 15.0 | 8.0 | 11.0 | 15.9 | SUB |
| HH 250L Run | 5 HIC Pool | 29.5 | 12.7 | 7.6 | 13.8 | 7.4 | 11.3 | 17.6 | SUB |
| HH 250L Run | 6 UFDF Pool | 30.1 | 12.9 | 7.8 | 14.1 | 7.6 | 11.3 | 16.2 | SUB |
| HH 250L Run | 7 DS | | | | | | | | SUB |
| JJ GMP 1 | 1 MabSelect Load | | | | | | | | SS |
| JJ GMP 1 | 2 MabSelect Pool | 33.6 | 13.17 | 7.54 | 14.66 | 7.22 | 9.49 | 13.88 | SS |
| JJ GMP 1 | 3 AEX Pool | 34.80 | 12.70 | 7.50 | 14.60 | 7.20 | 9.30 | 14.00 | SS |
| JJ GMP 1 | 4 CEX Pool | 33.00 | 12.40 | 7.40 | 14.80 | 7.40 | 10.00 | 14.80 | SS |
| JJ GMP 1 | 5 HIC Pool | 31.80 | 12.90 | 7.40 | 14.10 | 7.00 | 10.30 | 16.50 | SS |
| JJ GMP 1 | 6 UFDF Pool | 31.40 | 12.80 | 7.30 | 14.20 | 7.10 | 10.40 | 16.80 | SS |
| JJ GMP 1 | 7 DS | 32.90 | 12.60 | 7.30 | 14.10 | 7.20 | 10.40 | 15.50 | SS |
| JJ GMP 2 | 1 MabSelect Load | | | | | | | | SS |
| JJ GMP 2 | 2 MabSelect Pool | 34.95 | 13.13 | 7.48 | 14.72 | 7.04 | 9.35 | 13.23 | SS |
| JJ GMP 2 | 3 AEX Pool | 34.40 | 12.80 | 7.40 | 14.90 | 7.20 | 9.50 | 13.80 | SS |
| JJ GMP 2 | 4 CEX Pool | 32.10 | 12.60 | 7.60 | 15.20 | 7.50 | 10.30 | 14.70 | SS |
| JJ GMP 2 | 5 HIC Pool | 31.00 | 13.00 | 7.40 | 14.50 | 7.10 | 10.60 | 16.50 | SS |
| JJ GMP 2 | 6 UFDF Pool | 30.60 | 13.00 | 7.50 | 14.50 | 7.10 | 10.70 | 16.60 | SS |
| JJ GMP 2 | 7 DS | 31.60 | 12.60 | 7.40 | 14.30 | 7.10 | 10.60 | 16.40 | SS |
| JJ GMP 3 | 1 MabSelect Load | | | | | | | | SS |
| JJ GMP 3 | 2 MabSelect Pool | 34.23 | 13.17 | 7.54 | 14.49 | 7.18 | 9.50 | 13.86 | SS |
| JJ GMP 3 | 3 AEX Pool | 34.20 | 13.00 | 7.50 | 14.50 | 7.20 | 9.60 | 14.00 | SS |
| JJ GMP 3 | 4 CEX Pool | 32.30 | 12.70 | 7.50 | 14.90 | 7.50 | 10.20 | 14.80 | SS |
| JJ GMP 3 | 5 HIC Pool | 30.00 | 12.80 | 7.80 | 14.50 | 7.50 | 10.80 | 16.60 | SS |
| JJ GMP 3 | 6 UFDF Pool | 29.90 | 12.90 | 7.70 | 14.60 | 7.50 | 10.70 | 16.70 | SS |
| JJ GMP 3 | 7 DS | 31.30 | 12.60 | 7.70 | 14.40 | 7.50 | 10.70 | 15.90 | SS |

The percentages of the homodimer, dimer, trimer, tetramer, pentamer, hexamer and 7+mer fractions were assessed after each step by analytical HPLC. Briefly, supernatant from GL-2045 stably transfected CHO was generated according to the upstream methods described herein. GL-2045 was next purified according to the downstream methods described herein. Samples were obtained at the following successive stages of purification: Protein A MabSelect SuRe load, Protein A MabSelect SuRe pool, Anion exchange pool, Cation exchange pool, HIC pool, UFDF pool, and Drug Substance. The samples were compared by analytical SEC-HPLC. Briefly, isocratic separation was performed by HPLC using two SEC columns (Agilent Bio SEC (300 Å)) in series with UV detection at 280 nm on a High Performance Liquid Chromatography System (Agilent 1100 HPLC system). Chromatography is performed with a run time of 60 minutes, and a flow rate of 0.5 mL/min. The relative area percent of each peak is calculated.

The results are shown in FIG. 33. As apparent in FIG. 33, the downstream processing of the GL-2045 altered the levels of the smallest fractions, the homodimer and the dimer of the homodimer, as well as the largest fraction, the 7-mer+, while fractions 3-6 remained quite stable. With respect to the smaller multimers, the progressive downstream manufacturing steps, from the protein A column loading through to the final drug substance, resulted in an increased recovery of the homodimer and the dimer of the homodimer. However, the progressive downstream processing steps had the opposite effect on the highest order multimers resulted in a decrease in their relative percentages.

The resulting GL-2045 drug product had a defined multimer pattern which comprised, as a percentage of the total composition, less than about 20% homodimer, and more than about 28% of the 7-mer and above. The composition also comprised about 7-12% dimers of the homodimer, about 6-11% trimers of the homodimer, about 10-16% of the tetramer of the homodimer, about 6-9% of the pentamer of the homodimer, and about 10-14% of the hexamer of the homodimer.

The invention claimed is:

1. A method for producing a composition comprising a homodimer and/or a multimer of the homodimer, wherein the homodimer comprises two monomers each comprising amino acids 21-264 of SEQ ID NO:4, the method comprising:
    (a) culturing Chinese Hamster Ovary (CHO) cells that have been stably transfected with an expression vector comprising a nucleic acid sequence encoding SEQ ID NO: 4 at a growth temperature of 37° C.±1° C. for 5 days;
    (b) shifting the growth temperature from 37° C.±1° C. to 32.5° C.±1° C.; and
    (c) harvesting the homodimer and/or the multimer of the homodimer from the culture media.

2. The method of claim 1, wherein the cells are grown to a density of about 10 to about 25 million cells/mL, to a density of about 10 to about 15 million cells/mL, or to a density of about 15 to about 20 million cells/mL prior to shifting the growth temperature.

3. The method of claim 1, wherein the culturing is done in ActiCHO P base culture media comprising glutamine and wherein the CHO cells are fed during culture with ActiCHO feed A and ActiCHO feed B.

4. The method of claim 1, wherein the expression vector comprising the nucleic acid sequence encoding SEQ ID NO: 4 comprises a nucleic acid sequence encoding the leader peptide of SEQ ID NO: 1.

5. The method of claim 1, wherein the expression vector comprising a nucleic acid sequence encoding SEQ ID NO: 4 further comprises a piggyBac transposase recognition sequence and is transfected with a vector encoding a piggyBac transposase.

6. The method of claim 1, wherein the expression vector results in less than 20 genomic insertions.

7. A method for producing a composition comprising a homodimer and/or a multimer of the homodimer, wherein the homodimer comprises two monomers each comprising amino acids 21-264 of SEQ ID NO:4, the method comprising:
    (a) transfecting Chinese Hamster Ovary (CHO) cells with an expression vector comprising a nucleic acid encoding SEQ ID NO: 4;
    (b) culturing the CHO cells from (a) in a bioreactor with ActiCHO P media at a growth temperature of 37° C.±1;
    (c) feeding the cultures of (b) with Acti CHO Feed A and Acti CHO Feed B daily at a growth temperature of 37° C.±1° C. for 5 days;
    (d) shifting the growth temperature from 37° C.±1° C. to 32.5° C.±1° C.; and
    (e) harvesting the homodimer and/or multimer of the homodimer from the culture media,
    wherein >70% of the composition is present as the multimer of the homodimer, and wherein >30% of the multimers are higher order multimers.

8. The method of claim 7, wherein cell viability exceeds 85% at day 18 of culture.

9. The method of claim 7, wherein greater than 80% of the composition comprises the multimer of the homodimer.

10. A method of purifying the homodimer and/or multimer of the homodimer produced by the method of claim 1 comprising:
    (a) purifying the homodimer and/or multimer of the homodimer from the culture supernatant by affinity chromatography; and
    (b) polishing the homodimer and/or multimer of the homodimer by one or more of cation exchange chromatography, anion exchange chromatography, and hydrophobic interaction chromatography.

11. The method of claim 10, wherein the affinity chromatography uses a Mab Select SuRe protein A column.

12. The method of claim 10, wherein purification by affinity chromatography comprises eluting the homodimer and/or multimer of the homodimer from the affinity chromatography column using an elution buffer comprising sodium acetate and NaCl.

13. The method of claim 11, wherein the protein A column is regenerated with an NaOH buffer of at least 0.5 M.

14. The method of claim 10, wherein polishing the homodimer and/or multimer of the homodimer comprises anion exchange flow through chromatography.

15. The method of claim 14, wherein anion exchange flow through chromatography comprises using a Q Sepharose Fast Flow column.

16. The method of claim 10, wherein polishing the homodimer and/or multimer of the homodimer comprises cation exchange chromatography.

17. The method of claim 16, wherein cation exchange chromatography comprises using a POROS XS column.

18. The method of claim 16, wherein cation exchange chromatography comprises using a sodium acetate elution buffer.

19. The method of claim 18, wherein the elution buffer further comprises 36.5-38.5% of a 1 M NaCl buffer.

20. The method of claim 10, wherein polishing the homodimer and/or multimer of the homodimer comprises hydrophobic interaction chromatography.

21. The method of claim 20, wherein hydrophobic interaction chromatography comprises using a Phenyl Sepharose 6 Fast Flow High Sub Resin.

22. A method for purifying and polishing a composition comprising a homodimer and/or a multimer of the homodimer, wherein the homodimer comprises two monomers each comprising amino acids 21-264 of SEQ ID NO:4 comprising:
    (a) purifying the homodimer and/or multimer of the homodimer from a culture supernatant by protein A affinity chromatography, wherein the protein A chromatography uses an alkaline-resistant medium such as the MabSelect SuRe medium, wherein purifying is performed with at least two wash cycles;
(b) polishing the homodimer and/or multimer of the homodimer by cation exchange chromatography, wherein the cation exchange chromatography uses a high-capacity, high-resolution resin such as POROS XS, and wherein the elution buffer is a sodium acetate buffer comprised of 36.5-38.5% of a 1 M NaCl buffer;
(c) polishing the homodimer and/or multimer of the homodimer by anion exchange chromatography, wherein the anion exchange chromatography uses an anion exchange medium such as the Q Sepharose Fast Flow medium; and
(d) polishing the homodimer and/or multimer of the homodimer by hydrophobic interaction chromatography (HIC), wherein the HIC medium is Phenyl Sepharose 6 Fast Flow High Sub Resin and is selected to isolate or remove a particular fraction of the multimer of the homodimer in addition to polishing.

23. The method of claim 22, wherein the final protein titer of the composition is >4 g/L.

24. The method of claim 22, wherein the composition comprises >70% multimers.

25. The method of claim 1, further comprising shifting the pH from 7.1 to 7.0 at day 5.

26. The method of claim 7, further comprising shifting the pH from 7.1 to 7.0 at day 5.

27. The method of claim 7, wherein the final protein titer is at least 7.2 g/L.

28. A method for producing a composition comprising a homodimer and/or a multimer of the homodimer, wherein the homodimer comprises two monomers each comprising amino acids 21-264 of SEQ ID NO:4, the method comprising:
(a) culturing Chinese Hamster Ovary (CHO) cells, that have been stably transfected with an expression vector comprising a nucleic acid sequence encoding SEQ ID NO: 4, at a growth temperature of 37° C.±1° C. until the CHO cells reach a cell density of about 5 to about 30 million cells/mL;
(b) shifting the growth temperature from 37° C.±1° C. to 32.5° C.±1° C.; and
(c) harvesting the homodimer and/or the multimer of the homodimer from the culture media.

* * * * *

UNITED STATES PATENT AND TRADEMARK OFFICE
CERTIFICATE OF CORRECTION

Page 1 of 5

PATENT NO. : 11,155,574 B2
APPLICATION NO. : 16/467868
DATED : October 26, 2021
INVENTOR(S) : David S. Block et al.

It is certified that error appears in the above-identified patent and that said Letters Patent is hereby corrected as shown below:

On the Title Page

Please delete the Title Page and insert attached Title Page showing the corrected number of Claims.

In the Claims

Replace Column 69, Line 13-Column 72, Line 22, (approx.) with the following Claims:

1. A method for producing a composition comprising a homodimer and/or a multimer of the homodimer, wherein the homodimer comprises two monomers each comprising amino acids 21-264 of SEQ ID NO:4, the method comprising:
    (a) culturing Chinese Hamster Ovary (CHO) cells that have been stably transfected with an expression vector comprising a nucleic acid sequence encoding SEQ ID NO: 4 at a growth temperature of 37° C.±1° C. for 5 days;
    (b) shifting the growth temperature from 37° C.±1° C. to 32.5° C.±1° C.; and
    (c) harvesting the homodimer and/or the multimer of the homodimer from the culture media.

2. The method of claim 1, wherein the cells are grown to a density of about 10 to about 25 million cells/mL, to a density of about 10 to about 15 million cells/mL, or to a density of about 15 to about 20 million cells/mL prior to shifting the growth temperature.

3. The method of claim 1, wherein the culturing is done in ActiCHO P base culture media comprising glutamine and wherein the CHO cells are fed during culture with ActiCHO feed A and ActiCHO feed B.

4. The method of claim 1, wherein the expression vector comprising the nucleic acid sequence encoding SEQ ID NO: 4 comprises a nucleic acid sequence encoding the leader peptide of SEQ ID NO: 1.

5. The method of claim 1, wherein the expression vector results in less than 20 genomic insertions.

Signed and Sealed this
Twenty-fifth Day of June, 2024

Katherine Kelly Vidal
*Director of the United States Patent and Trademark Office*

6. A method for producing a composition comprising a homodimer and/or a multimer of the homodimer, wherein the homodimer comprises two monomers each comprising amino acids 21-264 of SEQ ID NO:4, the method comprising:

(a) transfecting Chinese Hamster Ovary (CHO) cells with an expression vector comprising a nucleic acid encoding SEQ ID NO: 4;

(b) culturing the CHO cells from (a) in a bioreactor with ActiCHO P media at a growth temperature of 37° C.±1;

(c) feeding the cultures of (b) with Acti CHO Feed A and Acti CHO Feed B daily at a growth temperature of 37° C.±1° C. for 5 days;

(d) shifting the growth temperature from 37° C.±1° C. to 32.5° C.±1° C.; and (e) harvesting the homodimer and/or multimer of the homodimer from the culture media, wherein >70% of the composition is present as the multimer of the homodimer, and wherein >30% of the multimers are higher order multimers.

7. The method of claim 6, wherein cell viability exceeds 85% at day 18 of culture.

8. The method of claim 6, wherein greater than 80% of the composition comprises the multimer of the homodimer.

9. A method of purifying the homodimer and/or multimer of the homodimer produced by the method of claim 1 comprising:

(a) purifying the homodimer and/or multimer of the homodimer from the culture supernatant by affinity chromatography; and (b) polishing the homodimer and/or multimer of the homodimer by one or more of cation exchange chromatography, anion exchange chromatography, and hydrophobic interaction chromatography.

10. The method of claim 9, wherein the affinity chromatography uses a Mab Select SuRe protein A column.

11. The method of claim 9, wherein purification by affinity chromatography comprises eluting the homodimer and/or multimer of the homodimer from the affinity chromatography column using an elution buffer comprising sodium acetate and NaCl.

12. The method of claim 10, wherein the protein A column is regenerated with an NaOH buffer of at least 0.5 M.

13. The method of claim 9, wherein polishing the homodimer and/or multimer of the homodimer comprises anion exchange flow through chromatography.

14. The method of claim 13, wherein anion exchange flow through chromatography comprises using a Q Sepharose Fast Flow column.

15. The method of claim 9, wherein polishing the homodimer and/or multimer of the homodimer comprises cation exchange chromatography.

16. The method of claim 15, wherein cation exchange chromatography comprises using a POROS XS column.

17. The method of claim 15, wherein cation exchange chromatography comprises using a sodium acetate elution buffer.

18. The method of claim 17, wherein the elution buffer further comprises 36.5-38.5% of a 1 M NaCl buffer.

19. The method of claim 9, wherein polishing the homodimer and/or multimer of the homodimer comprises hydrophobic interaction chromatography.

20. The method of claim 19, wherein hydrophobic interaction chromatography comprises using a Phenyl Sepharose 6 Fast Flow High Sub Resin.

21. A method for purifying and polishing a composition comprising a homodimer and/or a multimer of the homodimer, wherein the homodimer comprises two monomers each comprising amino acids 21-264 of SEQ ID NO:4 comprising:
    (a) purifying the homodimer and/or multimer of the homodimer from a culture supernatant by protein A affinity chromatography, wherein the protein A chromatography uses an alkaline-resistant medium such as the MabSelect SuRe medium, wherein purifying is performed with at least two wash cycles;
    (b) polishing the homodimer and/or multimer of the homodimer by cation exchange chromatography, wherein the cation exchange chromatography uses a high-capacity, high-resolution resin such as POROS XS, and wherein the elution buffer is a sodium acetate buffer comprised of 36.5-38.5% of a 1 M NaCl buffer;
    (c) polishing the homodimer and/or multimer of the homodimer by anion exchange chromatography, wherein the anion exchange chromatography uses an anion exchange medium such as the Q Sepharose Fast Flow medium; and
    (d) polishing the homodimer and/or multimer of the homodimer by hydrophobic interaction chromatography (HIC), wherein the HIC medium is Phenyl Sepharose 6 Fast Flow High Sub Resin and is selected to isolate or remove a particular fraction of the multimer of the homodimer in addition to polishing.

22. The method of claim 21, wherein the final protein titer of the composition is >4 g/L.

23. The method of claim 21, wherein the composition comprises >70% multimers.

24. The method of claim 1, further comprising shifting the pH from 7.1 to 7.0 at day 5.

25. The method of claim 6, further comprising shifting the pH from 7.1 to 7.0 at day 5.

26. The method of claim 6, wherein the final protein titer is at least 7.2 g/L.

27. A method for producing a composition comprising a homodimer and/or a multimer of the homodimer, wherein the homodimer comprises two monomers each comprising amino acids 21-264 of SEQ ID NO:4, the method comprising:

(a) culturing Chinese Hamster Ovary (CHO) cells, that have been stably transfected with an expression vector comprising a nucleic acid sequence encoding SEQ ID NO: 4, at a growth temperature of 37° C.±1° C. until the CHO cells reach a cell density of about 5 to about 30 million cells/mL;

(b) shifting the growth temperature from 37° C.±1° C. to 32.5° C.±1° C.; and (c) harvesting the homodimer and/or the multimer of the homodimer from the culture media.

(12) United States Patent
Block et al.

(10) Patent No.: US 11,155,574 B2
(45) Date of Patent: Oct. 26, 2021

(54) MANUFACTURING OPTIMIZATION OF GL-2045, A MULTIMERIZING STRADOMER

(71) Applicant: Gliknik Inc., Baltimore, MD (US)

(72) Inventors: David S. Block, Baltimore, MD (US); Emmanuel Y. Mérigeon, Baltimore, MD (US); Henrik Olsen, Baltimore, MD (US)

(73) Assignee: GLIKNIK INC., Baltimore, MD (US)

( * ) Notice: Subject to any disclaimer, the term of this patent is extended or adjusted under 35 U.S.C. 154(b) by 75 days.

(21) Appl. No.: 16/467,868

(22) PCT Filed: Dec. 8, 2017

(86) PCT No.: PCT/US2017/065397
§ 371 (c)(1),
(2) Date: Jun. 7, 2019

(87) PCT Pub. No.: WO2018/107079
PCT Pub. Date: Jun. 14, 2018

(65) Prior Publication Data
US 2020/0239518 A1    Jul. 30, 2020

Related U.S. Application Data

(60) Provisional application No. 62/432,402, filed on Dec. 9, 2016.

(51) Int. Cl.
*C07K 14/435* (2006.01)
*C07K 14/47* (2006.01)
*A61K 38/00* (2006.01)
*C07K 16/00* (2006.01)
*A61K 39/00* (2006.01)
*C07K 1/22* (2006.01)
*C07K 1/18* (2006.01)
*C07K 16/18* (2006.01)

(52) U.S. Cl.
CPC ............... *C07K 1/22* (2013.01); *C07K 1/18* (2013.01); *C07K 16/18* (2013.01); *C07K 2317/734* (2013.01)

(58) Field of Classification Search
CPC ......... A61K 38/00; C07K 14/47; A61P 43/00; A61P 35/00; A61P 29/00
See application file for complete search history.

(56) References Cited

U.S. PATENT DOCUMENTS

| | | | |
|---|---|---|---|
| 5,629,001 A | 5/1997 | Michael et al. | |
| 7,148,321 B2 | 12/2006 | Gillies et al. | |
| 7,511,121 B2 | 3/2009 | Arnason et al. | |
| 8,680,237 B2 | 3/2014 | Strome et al. | |
| 9,512,208 B2 | 12/2016 | Strome et al. | |
| 9,512,210 B2 | 12/2016 | Strome et al. | |
| 9,926,362 B2 | 3/2018 | Strome et al. | |
| 10,208,105 B2 | 2/2019 | Strome et al. | |
| 10,851,154 B2 | 12/2020 | Strome et al. | |
| 10,941,191 B2 | 3/2021 | Strome et al. | |
| 2002/0115157 A1 | 8/2002 | Davis et al. | |
| 2002/0142374 A1 | 10/2002 | Gallo et al. | |
| 2002/0147326 A1 | 10/2002 | Chaikin et al. | |
| 2003/0044423 A1 | 3/2003 | Gillies et al. | |
| 2003/0118592 A1 | 6/2003 | Ledbetter et al. | |
| 2003/0216546 A1 | 11/2003 | Tykocinski et al. | |
| 2004/0110226 A1 | 6/2004 | Lazar et al. | |
| 2004/0147731 A1 | 7/2004 | Parkos | |
| 2004/0151725 A1 | 8/2004 | Gray et al. | |
| 2005/0033029 A1 | 2/2005 | Lu | |
| 2006/0263856 A1 | 11/2006 | Gillies et al. | |
| 2008/0260738 A1 | 10/2008 | Moore et al. | |
| 2008/0267980 A1 | 10/2008 | Tomlinson et al. | |
| 2009/0117133 A1 | 5/2009 | Arnason et al. | |
| 2009/0136485 A1 | 5/2009 | Chu et al. | |
| 2009/0217401 A1 | 8/2009 | Korman et al. | |
| 2009/0304715 A1 | 12/2009 | Masuho et al. | |
| 2010/0048877 A1 | 2/2010 | Ruker et al. | |
| 2010/0093979 A1 | 4/2010 | Lazar | |
| 2010/0135987 A1 | 6/2010 | Hickman et al. | |
| 2010/0227805 A1 | 9/2010 | Karin et al. | |
| 2010/0239633 A1 | 9/2010 | Strome et al. | |
| 2010/0311116 A1 | 12/2010 | Wurm et al. | |
| 2011/0243966 A1 | 10/2011 | Farrington et al. | |
| 2011/0305697 A1 | 12/2011 | Walczak | |
| 2012/0283417 A1 | 11/2012 | Mosser et al. | |
| 2012/0309941 A1 | 12/2012 | Strome et al. | |
| 2013/0156765 A1* | 6/2013 | Block | A61P 37/00 424/134.1 |
| 2014/0072582 A1 | 3/2014 | Block et al. | |
| 2014/0105913 A1 | 4/2014 | Strome et al. | |
| 2014/0335075 A1 | 11/2014 | Strome et al. | |
| 2015/0056185 A1 | 2/2015 | Strome et al. | |
| 2015/0152406 A1 | 6/2015 | Grawunder | |
| 2015/0218236 A1 | 8/2015 | Pleass | |
| 2016/0280768 A1 | 9/2016 | Strome et al. | |
| 2016/0355570 A1 | 12/2016 | Strome et al. | |
| 2018/0002388 A1 | 1/2018 | Block et al. | |
| 2018/0186862 A1 | 7/2018 | Strome et al. | |
| 2018/0244772 A1 | 8/2018 | Block et al. | |
| 2019/0218275 A1 | 7/2019 | Strome et al. | |
| 2019/0389941 A1 | 12/2019 | Block et al. | |

FOREIGN PATENT DOCUMENTS

330 B2    2/2015
540 A1    7/1994
(Continued)

OTHER PUBLICATIONS

De Taeye, et al., "The Ligands for Human IgG and Their Effector Functions". Antibodies (2019); 8(2): 30, 18 pages.
(Continued)

*Primary Examiner* — Barry A Chestnut
(74) *Attorney, Agent, or Firm* — Cooley LLP

(57) ABSTRACT

The present disclosure involves optimized methods for production of biologically active proteins termed optimally manufactured stradomers. The present disclosure further provides compositions and methods useful in the treatment of diseases and conditions including autoimmune diseases, inflammatory diseases, or infectious diseases.

27 Claims, 37 Drawing Sheets

Specification includes a Sequence Listing.

SEQUENCE LISTING

```
<160> NUMBER OF SEQ ID NOS: 6

<210> SEQ ID NO 1
<211> LENGTH: 20
<212> TYPE: PRT
<213> ORGANISM: Artificial Sequence
```

<220> FEATURE:
<223> OTHER INFORMATION: Synthesized leader sequence

<400> SEQUENCE: 1

Met Glu Thr Asp Thr Leu Leu Leu Trp Val Leu Leu Leu Trp Val Pro
1               5                   10                  15

Gly Ser Thr Gly
            20

<210> SEQ ID NO 2
<211> LENGTH: 232
<212> TYPE: PRT
<213> ORGANISM: Homo sapiens

<400> SEQUENCE: 2

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 3
<211> LENGTH: 232
<212> TYPE: PRT
<213> ORGANISM: Homo sapiens

<400> SEQUENCE: 3

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

```
Lys Asp Thr Leu Met Ile Ser Arg Thr Pro Glu Val Thr Cys Val Val
             35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
65                   70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 4
<211> LENGTH: 264
<212> TYPE: PRT
<213> ORGANISM: Homo sapiens

<400> SEQUENCE: 4

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175
```

```
Phe Tyr Pro Ser Asp Ile Ala Val Glu Trp Glu Ser Asn Gly Gln Pro
            180                 185                 190
Glu Asn Asn Tyr Lys Thr Thr Pro Pro Val Leu Asp Ser Asp Gly Ser
        195                 200                 205
Phe Phe Leu Tyr Ser Lys Leu Thr Val Asp Lys Ser Arg Trp Gln Gln
    210                 215                 220
Gly Asn Val Phe Ser Cys Ser Val Met His Glu Ala Leu His Asn His
225                 230                 235                 240
Tyr Thr Gln Lys Ser Leu Ser Leu Ser Pro Gly Lys Glu Arg Lys Cys
                245                 250                 255
Cys Val Glu Cys Pro Pro Cys Pro
            260

<210> SEQ ID NO 5
<211> LENGTH: 264
<212> TYPE: PRT
<213> ORGANISM: Homo sapiens

<400> SEQUENCE: 5

Met Glu Thr Asp Thr Leu Leu Leu Trp Val Leu Leu Leu Trp Val Pro
1               5                   10                  15
Gly Ser Thr Gly Glu Pro Lys Ser Cys Asp Lys Thr His Thr Cys Pro
            20                  25                  30
Pro Cys Pro Ala Pro Glu Leu Leu Gly Gly Pro Ser Val Phe Leu Phe
        35                  40                  45
Pro Pro Lys Pro Lys Asp Thr Leu Met Ile Ser Arg Thr Pro Glu Val
    50                  55                  60
Thr Cys Val Val Val Asp Val Ser His Glu Asp Pro Glu Val Lys Phe
65                  70                  75                  80
Asn Trp Tyr Val Asp Gly Val Glu Val His Asn Ala Lys Thr Lys Pro
                85                  90                  95
Arg Glu Glu Gln Tyr Asn Ser Thr Tyr Arg Val Val Ser Val Leu Thr
            100                 105                 110
Val Leu His Gln Asp Trp Leu Asn Gly Lys Glu Tyr Lys Cys Lys Val
        115                 120                 125
Ser Asn Lys Ala Leu Pro Ala Pro Ile Glu Lys Thr Ile Ser Lys Ala
    130                 135                 140
Lys Gly Gln Pro Arg Glu Pro Gln Val Tyr Thr Leu Pro Pro Ser Arg
145                 150                 155                 160
Asp Glu Leu Thr Lys Asn Gln Val Ser Leu Thr Cys Leu Val Lys Gly
                165                 170                 175
Phe Tyr Pro Ser Asp Ile Ala Val Glu Trp Glu Ser Asn Gly Gln Pro
            180                 185                 190
Glu Asn Asn Tyr Lys Thr Thr Pro Pro Val Leu Asp Ser Asp Gly Ser
        195                 200                 205
Phe Phe Leu Tyr Ser Lys Leu Thr Val Asp Lys Ser Arg Trp Gln Gln
    210                 215                 220
Gly Asn Val Phe Ser Cys Ser Val Met His Glu Ala Leu His Asn His
225                 230                 235                 240
Tyr Thr Gln Lys Ser Leu Ser Leu Ser Pro Gly Lys Glu Arg Lys Cys
                245                 250                 255
Cys Val Glu Cys Pro Pro Cys Pro
            260
```

```
<210> SEQ ID NO 6
<211> LENGTH: 12
<212> TYPE: PRT
<213> ORGANISM: Homo sapiens

<400> SEQUENCE: 6

Glu Arg Lys Cys Cys Val Glu Cys Pro Pro Cys Pro
1               5                   10
```